US012577592B2

(12) United States Patent
Isobe et al.

(10) Patent No.: US 12,577,592 B2
(45) Date of Patent: Mar. 17, 2026

(54) GENETICALLY MODIFIED MICROORGANISM FOR PRODUCING 3-HYDROXYHEXANEDIOIC ACID AND/OR (E)-HEX-2-ENEDIOIC ACID AND PRODUCTION METHOD FOR SAID CHEMICALS

(71) Applicant: TORAY INDUSTRIES, INC., Tokyo (JP)

(72) Inventors: Kyohei Isobe, Kamakura (JP); Kenji Kawamura, Kamakura (JP); Katsushige Yamada, Kamakura (JP)

(73) Assignee: TORAY INDUSTRIES, INC., Tokyo (JP)

(*) Notice: Subject to any disclaimer, the term of this patent is extended or adjusted under 35 U.S.C. 154(b) by 781 days.

(21) Appl. No.: 17/908,059

(22) PCT Filed: Mar. 17, 2021

(86) PCT No.: PCT/JP2021/010871
§ 371 (c)(1),
(2) Date: Aug. 30, 2022

(87) PCT Pub. No.: WO2021/187533
PCT Pub. Date: Sep. 23, 2021

(65) Prior Publication Data

US 2023/0101086 A1 Mar. 30, 2023

(30) Foreign Application Priority Data

Mar. 18, 2020 (JP) ................................ 2020-047328

(51) Int. Cl.

| | |
|---|---|
| ***C12P 7/42*** | (2006.01) |
| ***C12N 1/21*** | (2006.01) |
| ***C12N 9/04*** | (2006.01) |
| ***C12N 15/01*** | (2006.01) |
| ***C12N 15/63*** | (2006.01) |
| ***C12R 1/185*** | (2006.01) |
| ***C12R 1/425*** | (2006.01) |

(52) U.S. Cl.
CPC .............. *C12P 7/42* (2013.01); *C12N 9/0006* (2013.01); *C12N 15/01* (2013.01); *C12N 15/63* (2013.01); *C12R 2001/185* (2021.05); *C12R 2001/425* (2021.05)

(58) Field of Classification Search
None
See application file for complete search history.

(56) References Cited

U.S. PATENT DOCUMENTS

| | | | | |
|---|---|---|---|---|
| 2016/0130618 | A1* | 5/2016 | Hara | C12P 13/001 435/141 |
| 2018/0142271 | A1* | 5/2018 | Isobe | C12P 7/42 |
| 2020/0291435 | A1 | 9/2020 | Isobe et al. | |

FOREIGN PATENT DOCUMENTS

| | | | | |
|---|---|---|---|---|
| WO | WO 2015/005406 A1 | 1/2015 | | |
| WO | WO-2019107516 A1 * | 6/2019 | | C12N 15/70 |

OTHER PUBLICATIONS

Babu et al., Engineering *Escherichia coli* for the production of adipic acid through the reversed beta-oxidation pathway, Process Biochem. 59, 2015, 2066-71. (Year: 2015).*
Fukui et al., *Escherichia coli* yjjPB genes encode a succinate transporter important for succinate production, Biosci, Biotechnol. Biochem. 81, 2017, 1837-44. (Year: 2017).*
Vuoristo et al., Metabolic Engineering of TCA Cycle for Production of Chemicals, Trends Biotechnol. 34, 2016, 191-97. (Year: 2016).*
International Search Report, issued in PCT/JP2021/010871, PCT/ISA/210, dated May 18, 2021.
Written Opinion of the International Searching Authority, issued in PCT/JP2021/010871, PCT/ISA/237, dated May 18, 2021.

* cited by examiner

*Primary Examiner* — Todd M Epstein
(74) *Attorney, Agent, or Firm* — Birch, Stewart, Kolasch & Birch, LLP

(57) ABSTRACT

A genetically modified microorganism that can produce 3-hydroxyadipic acid and/or α-hydromuconic acid with a high yield; and a method of producing 3-hydroxyadipic acid and/or α-hydromuconic acid using the genetically modified microorganism, are disclosed. The genetically modified microorganism has an ability to produce 3-hydroxyadipic acid and/or α-hydromuconic acid, and has an enhanced enzymatic activity to catalyze a reaction to reduce 3-oxoadipyl-CoA to 3-hydroxyadipyl-CoA, wherein, in the genetically modified microorganism, a dicarboxylic acid excretion carrier function is deleted or decreased.

8 Claims, No Drawings

Specification includes a Sequence Listing.

```
                         SEQUENCE LISTING

<160> NUMBER OF SEQ ID NOS: 93

<210> SEQ ID NO 1
<211> LENGTH: 771
<212> TYPE: DNA
<213> ORGANISM: Escherichia coli str. K-12 substr. MG1655
<220> FEATURE:
<221> NAME/KEY: CDS
<222> LOCATION: (1)..(771)

<400> SEQUENCE: 1

atg caa act gag caa cag cga gcc gta aca cgg ctt tgt atc cag tgt       48
Met Gln Thr Glu Gln Gln Arg Ala Val Thr Arg Leu Cys Ile Gln Cys
1               5                   10                  15

gga tta ttt ctt ttg caa cat ggt gcg gaa agc gcg ttg gtt gat gag       96
Gly Leu Phe Leu Leu Gln His Gly Ala Glu Ser Ala Leu Val Asp Glu
            20                  25                  30

ctt tcc tca cga ctg ggt cgg gca ctg gga atg gac agc gtc gaa agt      144
Leu Ser Ser Arg Leu Gly Arg Ala Leu Gly Met Asp Ser Val Glu Ser
        35                  40                  45

tct atc tct tcg aac gcc ata gtg ctg aca act att aaa gat ggg caa      192
Ser Ile Ser Ser Asn Ala Ile Val Leu Thr Thr Ile Lys Asp Gly Gln
    50                  55                  60

tgc ctg aca tcg aca cgt aaa aat cac gat cgc ggc att aat atg cat      240
Cys Leu Thr Ser Thr Arg Lys Asn His Asp Arg Gly Ile Asn Met His
65                  70                  75                  80

gtg gtg act gaa gtc cag cac att gtg att ctt gcg gag cat cat ctg      288
Val Val Thr Glu Val Gln His Ile Val Ile Leu Ala Glu His His Leu
                85                  90                  95

ctg gat tac aaa ggc gta gag aaa cga ttt agc caa att cag cca tta      336
Leu Asp Tyr Lys Gly Val Glu Lys Arg Phe Ser Gln Ile Gln Pro Leu
            100                 105                 110

cgt tac cca aga tgg ctg gta gcc tta atg gtt ggc ctt tct tgc gcc      384
Arg Tyr Pro Arg Trp Leu Val Ala Leu Met Val Gly Leu Ser Cys Ala
        115                 120                 125

tgt ttc tgt aaa ctc aat aac ggt ggc tgg gat ggt gcc gtc atc acc      432
```

-continued

Cys Phe Cys Lys Leu Asn Asn Gly Gly Trp Asp Gly Ala Val Ile Thr
130 135 140 ttc ttt gcc agt acg acc gcg atg tat atc cgc cag ctg ctg gca caa 480
Phe Phe Ala Ser Thr Thr Ala Met Tyr Ile Arg Gln Leu Leu Ala Gln
145 150 155 160 cgt cat ctt cat cca cag atc aac ttt tgc ctt acc gct ttc gcc gcc 528
Arg His Leu His Pro Gln Ile Asn Phe Cys Leu Thr Ala Phe Ala Ala
165 170 175 acc acc att tcc gga ttg ctt ttg caa ctc ccc act ttc agc aat acc 576
Thr Thr Ile Ser Gly Leu Leu Leu Gln Leu Pro Thr Phe Ser Asn Thr
180 185 190 ccc acc att gcg atg gcc gcc agc gtt ctg ctg cta gtg ccg ggc ttt 624
Pro Thr Ile Ala Met Ala Ala Ser Val Leu Leu Leu Val Pro Gly Phe
195 200 205 ccg ttg att aat gcc gtc gcc gat atg ttt aaa ggc cac atc aat acc 672
Pro Leu Ile Asn Ala Val Ala Asp Met Phe Lys Gly His Ile Asn Thr
210 215 220 gga ctg gca cgc tgg gcg atc gcc agt ctg ctg aca ctg gct acc tgc 720
Gly Leu Ala Arg Trp Ala Ile Ala Ser Leu Leu Thr Leu Ala Thr Cys
225 230 235 240 gtc ggc gta gtg atg gca ctg acg att tgg ggg cta cgc gga tgg gtg 768
Val Gly Val Val Met Ala Leu Thr Ile Trp Gly Leu Arg Gly Trp Val
245 250 255 tga 771

<210> SEQ ID NO 2
<211> LENGTH: 256
<212> TYPE: PRT
<213> ORGANISM: Escherichia coli str. K-12 substr. MG1655

<400> SEQUENCE: 2

Met Gln Thr Glu Gln Gln Arg Ala Val Thr Arg Leu Cys Ile Gln Cys
1 5 10 15

Gly Leu Phe Leu Leu Gln His Gly Ala Glu Ser Ala Leu Val Asp Glu
20 25 30

Leu Ser Ser Arg Leu Gly Arg Ala Leu Gly Met Asp Ser Val Glu Ser
35 40 45

Ser Ile Ser Ser Asn Ala Ile Val Leu Thr Thr Ile Lys Asp Gly Gln
50 55 60

Cys Leu Thr Ser Thr Arg Lys Asn His Asp Arg Gly Ile Asn Met His
65 70 75 80

Val Val Thr Glu Val Gln His Ile Val Ile Leu Ala Glu His His Leu
85 90 95

Leu Asp Tyr Lys Gly Val Glu Lys Arg Phe Ser Gln Ile Gln Pro Leu
100 105 110

Arg Tyr Pro Arg Trp Leu Val Ala Leu Met Val Gly Leu Ser Cys Ala
115 120 125

Cys Phe Cys Lys Leu Asn Asn Gly Gly Trp Asp Gly Ala Val Ile Thr
130 135 140

Phe Phe Ala Ser Thr Thr Ala Met Tyr Ile Arg Gln Leu Leu Ala Gln
145 150 155 160

Arg His Leu His Pro Gln Ile Asn Phe Cys Leu Thr Ala Phe Ala Ala
165 170 175

Thr Thr Ile Ser Gly Leu Leu Leu Gln Leu Pro Thr Phe Ser Asn Thr
180 185 190

Pro Thr Ile Ala Met Ala Ala Ser Val Leu Leu Leu Val Pro Gly Phe
195 200 205

-continued

```
Pro Leu Ile Asn Ala Val Ala Asp Met Phe Lys Gly His Ile Asn Thr
    210                 215                 220

Gly Leu Ala Arg Trp Ala Ile Ala Ser Leu Leu Thr Leu Ala Thr Cys
225                 230                 235                 240

Val Gly Val Val Met Ala Leu Thr Ile Trp Gly Leu Arg Gly Trp Val
                245                 250                 255


<210> SEQ ID NO 3
<211> LENGTH: 474
<212> TYPE: DNA
<213> ORGANISM: Escherichia coli str. K-12 substr. MG1655
<220> FEATURE:
<221> NAME/KEY: CDS
<222> LOCATION: (1)..(474)

<400> SEQUENCE: 3

atg ggt gtg atc gaa ttt ctg tta gcg ttg gcg cag gat atg atc ctc       48
Met Gly Val Ile Glu Phe Leu Leu Ala Leu Ala Gln Asp Met Ile Leu
1               5                   10                  15

gcc gcc att cct gcg gtc ggc ttt gcg atg gtg ttc aac gtt ccc gtg       96
Ala Ala Ile Pro Ala Val Gly Phe Ala Met Val Phe Asn Val Pro Val
            20                  25                  30

cgg gcg tta cgc tgg tgt gcg ctg ctt ggc tcg ata ggt cat ggt tcc      144
Arg Ala Leu Arg Trp Cys Ala Leu Leu Gly Ser Ile Gly His Gly Ser
        35                  40                  45

cga atg atc ttg atg acc agc ggg ttg aat att gag tgg tca acc ttt      192
Arg Met Ile Leu Met Thr Ser Gly Leu Asn Ile Glu Trp Ser Thr Phe
    50                  55                  60

atg gct tct atg ctg gtc ggt acc att ggt att caa tgg tcg cgc tgg      240
Met Ala Ser Met Leu Val Gly Thr Ile Gly Ile Gln Trp Ser Arg Trp
65                  70                  75                  80

tat ctg gcg cat ccg aaa gtg ttt acc gtg gcg gcc gtt atc cct atg      288
Tyr Leu Ala His Pro Lys Val Phe Thr Val Ala Ala Val Ile Pro Met
                85                  90                  95

ttc ccg ggc ata tcg gct tat acc gca atg att tcg gcg gta aaa atc      336
Phe Pro Gly Ile Ser Ala Tyr Thr Ala Met Ile Ser Ala Val Lys Ile
            100                 105                 110

agc cag tta ggt tac agc gaa ccg ttg atg att acc ctg tta acc aac      384
Ser Gln Leu Gly Tyr Ser Glu Pro Leu Met Ile Thr Leu Leu Thr Asn
        115                 120                 125

ttt ctt aca gct tca tcg att gtt ggt gcg tta tcc atc ggt ctt tcc      432
Phe Leu Thr Ala Ser Ser Ile Val Gly Ala Leu Ser Ile Gly Leu Ser
    130                 135                 140

att cct gga tta tgg ttg tac cgc aag cgc cct cgc gta taa              474
Ile Pro Gly Leu Trp Leu Tyr Arg Lys Arg Pro Arg Val
145                 150                 155


<210> SEQ ID NO 4
<211> LENGTH: 157
<212> TYPE: PRT
<213> ORGANISM: Escherichia coli str. K-12 substr. MG1655

<400> SEQUENCE: 4

Met Gly Val Ile Glu Phe Leu Leu Ala Leu Ala Gln Asp Met Ile Leu
1               5                   10                  15

Ala Ala Ile Pro Ala Val Gly Phe Ala Met Val Phe Asn Val Pro Val
            20                  25                  30

Arg Ala Leu Arg Trp Cys Ala Leu Leu Gly Ser Ile Gly His Gly Ser
        35                  40                  45

Arg Met Ile Leu Met Thr Ser Gly Leu Asn Ile Glu Trp Ser Thr Phe
```

-continued 50 55 60

Met Ala Ser Met Leu Val Gly Thr Ile Gly Ile Gln Trp Ser Arg Trp
65 70 75 80

Tyr Leu Ala His Pro Lys Val Phe Thr Val Ala Ala Val Ile Pro Met
85 90 95

Phe Pro Gly Ile Ser Ala Tyr Thr Ala Met Ile Ser Ala Val Lys Ile
100 105 110

Ser Gln Leu Gly Tyr Ser Glu Pro Leu Met Ile Thr Leu Leu Thr Asn
115 120 125

Phe Leu Thr Ala Ser Ser Ile Val Gly Ala Leu Ser Ile Gly Leu Ser
130 135 140

Ile Pro Gly Leu Trp Leu Tyr Arg Lys Arg Pro Arg Val
145 150 155

<210> SEQ ID NO 5
<211> LENGTH: 801
<212> TYPE: DNA
<213> ORGANISM: Serratia grimesii NBRC13537
<220> FEATURE:
<221> NAME/KEY: CDS
<222> LOCATION: (1)..(801)

<400> SEQUENCE: 5 atg cag cag ccg acc acc acc gac acc ccg ccg ccg cag cgg caa cag 48
Met Gln Gln Pro Thr Thr Thr Asp Thr Pro Pro Pro Gln Arg Gln Gln
1 5 10 15 cgt gaa atc acc cgt ctg tgt att caa tgc gcc ttg ctg ttg tta cag 96
Arg Glu Ile Thr Arg Leu Cys Ile Gln Cys Ala Leu Leu Leu Leu Gln
20 25 30 cat ggg gcg gaa agt atg gtg gtg gag cag ttg tcg acg cgt ttg ggg 144
His Gly Ala Glu Ser Met Val Val Glu Gln Leu Ser Thr Arg Leu Gly
35 40 45 ttg gca ttg ggc atg gac agc gta gaa agt tcg ata tcg gcc aac gcg 192
Leu Ala Leu Gly Met Asp Ser Val Glu Ser Ser Ile Ser Ala Asn Ala
50 55 60 gtg gtg ttg acg acc ctc agt cac ggt gaa tgc tta acc acg aca cgc 240
Val Val Leu Thr Thr Leu Ser His Gly Glu Cys Leu Thr Thr Thr Arg
65 70 75 80 aag aac gtc gat cgc ggc atc aat atg cag atg gtg acc gag gtg caa 288
Lys Asn Val Asp Arg Gly Ile Asn Met Gln Met Val Thr Glu Val Gln
85 90 95 cat atc gtt att ttg gca gaa cac cgg ctg gcg gat gca cac gac gtg 336
His Ile Val Ile Leu Ala Glu His Arg Leu Ala Asp Ala His Asp Val
100 105 110 gcc cgc cgt ctc cag aaa att cgc ccg ctt cgc tat cca cgc tgg ctg 384
Ala Arg Arg Leu Gln Lys Ile Arg Pro Leu Arg Tyr Pro Arg Trp Leu
115 120 125 gtg gtg ttg atg gtg gcg tta tct tgc ggt tgc ttc agc atg ctc aac 432
Val Val Leu Met Val Ala Leu Ser Cys Gly Cys Phe Ser Met Leu Asn
130 135 140 ggt ggc gat caa aaa gcg ttt gcc gtg acc ttt atc gcc agt ggt ctg 480
Gly Gly Asp Gln Lys Ala Phe Ala Val Thr Phe Ile Ala Ser Gly Leu
145 150 155 160 gcc atg tcg gtg cgc caa atg ctg acc gcc cgc cac atg aat ccg ttg 528
Ala Met Ser Val Arg Gln Met Leu Thr Ala Arg His Met Asn Pro Leu
165 170 175 atc aat ttt tgt ctg acg gcc ttt gtc gcc act tcg gtt tcc ggc ttg 576
Ile Asn Phe Cys Leu Thr Ala Phe Val Ala Thr Ser Val Ser Gly Leu
180 185 190

```
ctg ctg cga ttg ccg gta ttc agc caa acc tcc acg gtg gcg atg gct      624
Leu Leu Arg Leu Pro Val Phe Ser Gln Thr Ser Thr Val Ala Met Ala
        195                 200                 205

gcc agc gtg ctg ctg ctg gta ccc ggg ttc cca ctg att aac gcg gtc      672
Ala Ser Val Leu Leu Leu Val Pro Gly Phe Pro Leu Ile Asn Ala Val
    210                 215                 220

gcc gat atg ttt aag ggg cac att aat acc ggc ttg gcg cgt tgg gcg      720
Ala Asp Met Phe Lys Gly His Ile Asn Thr Gly Leu Ala Arg Trp Ala
225                 230                 235                 240

atg gcg agt ttg ctg acg ctg gcc act tgt atc ggt gta gtg atg gcg      768
Met Ala Ser Leu Leu Thr Leu Ala Thr Cys Ile Gly Val Val Met Ala
                245                 250                 255

atg tcg ctg tgg gat ctg cgg ggg tgg tca tga                          801
Met Ser Leu Trp Asp Leu Arg Gly Trp Ser
            260                 265


<210> SEQ ID NO 6
<211> LENGTH: 266
<212> TYPE: PRT
<213> ORGANISM: Serratia grimesii NBRC13537

<400> SEQUENCE: 6

Met Gln Gln Pro Thr Thr Thr Asp Thr Pro Pro Pro Gln Arg Gln Gln
1               5                   10                  15

Arg Glu Ile Thr Arg Leu Cys Ile Gln Cys Ala Leu Leu Leu Leu Gln
            20                  25                  30

His Gly Ala Glu Ser Met Val Val Glu Gln Leu Ser Thr Arg Leu Gly
        35                  40                  45

Leu Ala Leu Gly Met Asp Ser Val Glu Ser Ser Ile Ser Ala Asn Ala
    50                  55                  60

Val Val Leu Thr Thr Leu Ser His Gly Glu Cys Leu Thr Thr Thr Arg
65                  70                  75                  80

Lys Asn Val Asp Arg Gly Ile Asn Met Gln Met Val Thr Glu Val Gln
                85                  90                  95

His Ile Val Ile Leu Ala Glu His Arg Leu Ala Asp Ala His Asp Val
            100                 105                 110

Ala Arg Arg Leu Gln Lys Ile Arg Pro Leu Arg Tyr Pro Arg Trp Leu
        115                 120                 125

Val Val Leu Met Val Ala Leu Ser Cys Gly Cys Phe Ser Met Leu Asn
    130                 135                 140

Gly Gly Asp Gln Lys Ala Phe Ala Val Thr Phe Ile Ala Ser Gly Leu
145                 150                 155                 160

Ala Met Ser Val Arg Gln Met Leu Thr Ala Arg His Met Asn Pro Leu
                165                 170                 175

Ile Asn Phe Cys Leu Thr Ala Phe Val Ala Thr Ser Val Ser Gly Leu
            180                 185                 190

Leu Leu Arg Leu Pro Val Phe Ser Gln Thr Ser Thr Val Ala Met Ala
        195                 200                 205

Ala Ser Val Leu Leu Leu Val Pro Gly Phe Pro Leu Ile Asn Ala Val
    210                 215                 220

Ala Asp Met Phe Lys Gly His Ile Asn Thr Gly Leu Ala Arg Trp Ala
225                 230                 235                 240

Met Ala Ser Leu Leu Thr Leu Ala Thr Cys Ile Gly Val Val Met Ala
                245                 250                 255

Met Ser Leu Trp Asp Leu Arg Gly Trp Ser
            260                 265
```

-continued

<210> SEQ ID NO 7
<211> LENGTH: 486
<212> TYPE: DNA
<213> ORGANISM: Serratia grimesii NBRC13537
<220> FEATURE:
<221> NAME/KEY: CDS
<222> LOCATION: (1)..(486)

<400> SEQUENCE: 7 gtg gga tct gcg ggg gtg gtc atg agt ttg ctt tgg gcc tta ctg cag 48
Val Gly Ser Ala Gly Val Val Met Ser Leu Leu Trp Ala Leu Leu Gln
1 5 10 15 gac atg ttg ctg gcg gcg gta ccg gcg ctg ggt ttt gcc atg gta ttt 96
Asp Met Leu Leu Ala Ala Val Pro Ala Leu Gly Phe Ala Met Val Phe
20 25 30 aac gtg ccg gtg cgc gcg ctg cgt tat tgt gca ctg ctt ggc gca gta 144
Asn Val Pro Val Arg Ala Leu Arg Tyr Cys Ala Leu Leu Gly Ala Val
35 40 45 ggc cac ggt tca cgc atg ctg atg atg cac gca gga atg aac atc gaa 192
Gly His Gly Ser Arg Met Leu Met Met His Ala Gly Met Asn Ile Glu
50 55 60 tgg gcc acg ttt ttg gca tcg att ttg atc ggt atg atc ggt att tac 240
Trp Ala Thr Phe Leu Ala Ser Ile Leu Ile Gly Met Ile Gly Ile Tyr
65 70 75 80 tgg tcg cgc tgg ctg ttg gca cac ccg aag gtg ttt acc gtg gcg gca 288
Trp Ser Arg Trp Leu Leu Ala His Pro Lys Val Phe Thr Val Ala Ala
85 90 95 gtg att ccg atg ttc cca ggg ata ccg gct tat act gcg atg atc tcg 336
Val Ile Pro Met Phe Pro Gly Ile Pro Ala Tyr Thr Ala Met Ile Ser
100 105 110 gtg gtg gaa att tcg cat ctg ggt tat agc gag gcg ctg atg gcc acc 384
Val Val Glu Ile Ser His Leu Gly Tyr Ser Glu Ala Leu Met Ala Thr
115 120 125 ctg atg agt aac ttc ctc aag gcc tgt ttt atc gtc ggc gcg tta tcg 432
Leu Met Ser Asn Phe Leu Lys Ala Cys Phe Ile Val Gly Ala Leu Ser
130 135 140 atc ggg ctg tca tta ccc ggg ctg tgg cta tat cgg aaa cgc ccg gga 480
Ile Gly Leu Ser Leu Pro Gly Leu Trp Leu Tyr Arg Lys Arg Pro Gly
145 150 155 160 gtc taa 486
Val

<210> SEQ ID NO 8
<211> LENGTH: 161
<212> TYPE: PRT
<213> ORGANISM: Serratia grimesii NBRC13537

<400> SEQUENCE: 8

Val Gly Ser Ala Gly Val Val Met Ser Leu Leu Trp Ala Leu Leu Gln
1 5 10 15

Asp Met Leu Leu Ala Ala Val Pro Ala Leu Gly Phe Ala Met Val Phe
20 25 30

Asn Val Pro Val Arg Ala Leu Arg Tyr Cys Ala Leu Leu Gly Ala Val
35 40 45

Gly His Gly Ser Arg Met Leu Met Met His Ala Gly Met Asn Ile Glu
50 55 60

Trp Ala Thr Phe Leu Ala Ser Ile Leu Ile Gly Met Ile Gly Ile Tyr
65 70 75 80

Trp Ser Arg Trp Leu Leu Ala His Pro Lys Val Phe Thr Val Ala Ala
85 90 95

```
Val Ile Pro Met Phe Pro Gly Ile Pro Ala Tyr Thr Ala Met Ile Ser
            100                 105                 110

Val Val Glu Ile Ser His Leu Gly Tyr Ser Glu Ala Leu Met Ala Thr
        115                 120                 125

Leu Met Ser Asn Phe Leu Lys Ala Cys Phe Ile Val Gly Ala Leu Ser
    130                 135                 140

Ile Gly Leu Ser Leu Pro Gly Leu Trp Leu Tyr Arg Lys Arg Pro Gly
145                 150                 155                 160

Val


<210> SEQ ID NO 9
<211> LENGTH: 1530
<212> TYPE: DNA
<213> ORGANISM: Serratia marcescens ATCC13880
<220> FEATURE:
<221> NAME/KEY: CDS
<222> LOCATION: (1)..(1530)

<400> SEQUENCE: 9

atg gca gaa agt aat gcg gca att caa tcg gct gcg att atc ggc gcg       48
Met Ala Glu Ser Asn Ala Ala Ile Gln Ser Ala Ala Ile Ile Gly Ala
1               5                   10                  15

gga acg atg ggc aga ggc atc gct tat ctt ttc gcg caa aaa ggc att       96
Gly Thr Met Gly Arg Gly Ile Ala Tyr Leu Phe Ala Gln Lys Gly Ile
            20                  25                  30

cgc acg gtg ctt tat aat cgc aac ggc aat acc ctc aat cag gct cgc      144
Arg Thr Val Leu Tyr Asn Arg Asn Gly Asn Thr Leu Asn Gln Ala Arg
        35                  40                  45

gaa tat atc gcg caa gac ctg aac aag aaa gtc gaa cag ggc aag atc      192
Glu Tyr Ile Ala Gln Asp Leu Asn Lys Lys Val Glu Gln Gly Lys Ile
    50                  55                  60

gcg ctg cag gat aaa ggc gcg gtg ctg gcc aat cta atg ttc act tca      240
Ala Leu Gln Asp Lys Gly Ala Val Leu Ala Asn Leu Met Phe Thr Ser
65                  70                  75                  80

gtg ttt gag gcc atc gcc gac agc gag ctg gtg ata gaa acc atc gcc      288
Val Phe Glu Ala Ile Ala Asp Ser Glu Leu Val Ile Glu Thr Ile Ala
                85                  90                  95

gag caa gaa caa acc aaa ctt gag gtg ctg gcg gcc atc gcc gcg gtg      336
Glu Gln Glu Gln Thr Lys Leu Glu Val Leu Ala Ala Ile Ala Ala Val
            100                 105                 110

gtc aag ccc gac acg ctg atc gcc acc aat acc tcc tca ctg tcg ctt      384
Val Lys Pro Asp Thr Leu Ile Ala Thr Asn Thr Ser Ser Leu Ser Leu
        115                 120                 125

aac aag ctg gct act gcg gtg acg cac agc gaa cgc ttt atc ggt ttg      432
Asn Lys Leu Ala Thr Ala Val Thr His Ser Glu Arg Phe Ile Gly Leu
    130                 135                 140

cat ttt ttc aac ccc gcg ccg ctg atg aag ctg att gaa atc att ccg      480
His Phe Phe Asn Pro Ala Pro Leu Met Lys Leu Ile Glu Ile Ile Pro
145                 150                 155                 160

gcc tac ttt acc gcg cac gcc acc acc gaa cgc tgc cgc caa ctg gtg      528
Ala Tyr Phe Thr Ala His Ala Thr Thr Glu Arg Cys Arg Gln Leu Val
                165                 170                 175

gcg gcg ttg ggg aaa cac gat gtc gtc tgc cag gcc acg ccg ggg ttc      576
Ala Ala Leu Gly Lys His Asp Val Val Cys Gln Ala Thr Pro Gly Phe
            180                 185                 190

atc gtc aat cgc atg gcc cgc ccc tac tac ctg gaa ggg ttc cgc ctg      624
Ile Val Asn Arg Met Ala Arg Pro Tyr Tyr Leu Glu Gly Phe Arg Leu
        195                 200                 205

ttg gaa gaa cac gtg gcg cgc gcg gct cag atc gac cgc gcc ctc aag      672
```

-continued

```
Leu Glu Glu His Val Ala Arg Ala Ala Gln Ile Asp Arg Ala Leu Lys
    210                 215                 220

gcc ggc ggg cgc ttc cgc atg ggg ccg ctc gag ctg acc gat ttt atc      720
Ala Gly Gly Arg Phe Arg Met Gly Pro Leu Glu Leu Thr Asp Phe Ile
225                 230                 235                 240

ggc caa gac atc aac tat cag gtc agt cgg caa atc tgg cag gat atg      768
Gly Gln Asp Ile Asn Tyr Gln Val Ser Arg Gln Ile Trp Gln Asp Met
                245                 250                 255

caa tac gac ccg cgc tat acc ccc ggt cat ctg cag cgt tca ctg gtc      816
Gln Tyr Asp Pro Arg Tyr Thr Pro Gly His Leu Gln Arg Ser Leu Val
            260                 265                 270

gat gcc ggt ctg ttg ggg aaa aag aac ggc cgc tcc tat ttt gcc gcc      864
Asp Ala Gly Leu Leu Gly Lys Lys Asn Gly Arg Ser Tyr Phe Ala Ala
        275                 280                 285

gaa gaa acc gcc ccg ccg gtg acg gcc gcc agc aat gca gac gtc gag      912
Glu Glu Thr Ala Pro Pro Val Thr Ala Ala Ser Asn Ala Asp Val Glu
    290                 295                 300

acg ctg cgc gtt tac ggc gag cac cct ttt ttt acc ctg tta cag cag      960
Thr Leu Arg Val Tyr Gly Glu His Pro Phe Phe Thr Leu Leu Gln Gln
305                 310                 315                 320

cga gcc gcg ctt cag tgg cca cag ctg cgc gtg gaa caa cgg ccg gca     1008
Arg Ala Ala Leu Gln Trp Pro Gln Leu Arg Val Glu Gln Arg Pro Ala
                325                 330                 335

tta ccg ggg ctg ggg tcg gcc gtc cag atc aat gac gct ttc acc gtc     1056
Leu Pro Gly Leu Gly Ser Ala Val Gln Ile Asn Asp Ala Phe Thr Val
            340                 345                 350

agc atc acc gat ggc cgc acg gcg agc caa ctg gcc gag cag acg gca     1104
Ser Ile Thr Asp Gly Arg Thr Ala Ser Gln Leu Ala Glu Gln Thr Ala
        355                 360                 365

gcg gat gcc ttt gtg gtc gat gtc gcc ctg aac tac gcc gac acg acg     1152
Ala Asp Ala Phe Val Val Asp Val Ala Leu Asn Tyr Ala Asp Thr Thr
    370                 375                 380

tat ctg gcg gcg gcg cac agc cgc cac gcc tct gcg gcc aat aag gcg     1200
Tyr Leu Ala Ala Ala His Ser Arg His Ala Ser Ala Ala Asn Lys Ala
385                 390                 395                 400

ctg ttt tta cgc ctg ctg cac acg gca atc ccg cag gtt gaa ttt atc     1248
Leu Phe Leu Arg Leu Leu His Thr Ala Ile Pro Gln Val Glu Phe Ile
                405                 410                 415

aag gac tct ccg gcg ctt atc gtc gcc cgc gtc ctc agc agc ctg atc     1296
Lys Asp Ser Pro Ala Leu Ile Val Ala Arg Val Leu Ser Ser Leu Ile
            420                 425                 430

aat gag tcg gtg atc atg gtg gaa agc ggc gtc tgc agc cgg gaa gac     1344
Asn Glu Ser Val Ile Met Val Glu Ser Gly Val Cys Ser Arg Glu Asp
        435                 440                 445

atc gat gtc gcc gcc gtc gcg ggc gtt aac tac gcc ggc ggc att ttc     1392
Ile Asp Val Ala Ala Val Ala Gly Val Asn Tyr Ala Gly Gly Ile Phe
    450                 455                 460

gac tgg ctc ggc aaa ctg ggg gag aaa aac gtc agg aca acg ctg agc     1440
Asp Trp Leu Gly Lys Leu Gly Glu Lys Asn Val Arg Thr Thr Leu Ser
465                 470                 475                 480

aat ctg gct cag ctg ctg cac gcg gcg cgc tat gcg ccg cat tac acc     1488
Asn Leu Ala Gln Leu Leu His Ala Ala Arg Tyr Ala Pro His Tyr Thr
                485                 490                 495

ctt ctg cac gcc gcg caa ccg gcg ctg acg acc acg cct taa             1530
Leu Leu His Ala Ala Gln Pro Ala Leu Thr Thr Thr Pro
            500                 505
```

<210> SEQ ID NO 10
<211> LENGTH: 509
<212> TYPE: PRT

-continued

<213> ORGANISM: Serratia marcescens ATCC13880

<400> SEQUENCE: 10

```
Met Ala Glu Ser Asn Ala Ala Ile Gln Ser Ala Ala Ile Ile Gly Ala
1               5                   10                  15

Gly Thr Met Gly Arg Gly Ile Ala Tyr Leu Phe Ala Gln Lys Gly Ile
            20                  25                  30

Arg Thr Val Leu Tyr Asn Arg Asn Gly Asn Thr Leu Asn Gln Ala Arg
        35                  40                  45

Glu Tyr Ile Ala Gln Asp Leu Asn Lys Lys Val Glu Gln Gly Lys Ile
    50                  55                  60

Ala Leu Gln Asp Lys Gly Ala Val Leu Ala Asn Leu Met Phe Thr Ser
65                  70                  75                  80

Val Phe Glu Ala Ile Ala Asp Ser Glu Leu Val Ile Glu Thr Ile Ala
                85                  90                  95

Glu Gln Glu Gln Thr Lys Leu Glu Val Leu Ala Ala Ile Ala Ala Val
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
    130                 135                 140

His Phe Phe Asn Pro Ala Pro Leu Met Lys Leu Ile Glu Ile Ile Pro
145                 150                 155                 160

Ala Tyr Phe Thr Ala His Ala Thr Thr Glu Arg Cys Arg Gln Leu Val
                165                 170                 175

Ala Ala Leu Gly Lys His Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Ala Gln Ile Asp Arg Ala Leu Lys
    210                 215                 220

Ala Gly Gly Arg Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Tyr Phe Ala Ala
        275                 280                 285

Glu Glu Thr Ala Pro Pro Val Thr Ala Ala Ser Asn Ala Asp Val Glu
    290                 295                 300

Thr Leu Arg Val Tyr Gly Glu His Pro Phe Phe Thr Leu Leu Gln Gln
305                 310                 315                 320

Arg Ala Ala Leu Gln Trp Pro Gln Leu Arg Val Glu Gln Arg Pro Ala
                325                 330                 335

Leu Pro Gly Leu Gly Ser Ala Val Gln Ile Asn Asp Ala Phe Thr Val
            340                 345                 350

Ser Ile Thr Asp Gly Arg Thr Ala Ser Gln Leu Ala Glu Gln Thr Ala
        355                 360                 365

Ala Asp Ala Phe Val Val Asp Val Ala Leu Asn Tyr Ala Asp Thr Thr
    370                 375                 380

Tyr Leu Ala Ala Ala His Ser Arg His Ala Ser Ala Ala Asn Lys Ala
385                 390                 395                 400
```

-continued

```
Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Gly Gly Ile Phe
    450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505


<210> SEQ ID NO 11
<211> LENGTH: 1530
<212> TYPE: DNA
<213> ORGANISM: Serratia nematodiphila DSM21420
<220> FEATURE:
<221> NAME/KEY: CDS
<222> LOCATION: (1)..(1530)

<400> SEQUENCE: 11

atg gca gaa agt aat gcg gca att caa tcg gct gcg att atc ggc gcg       48
Met Ala Glu Ser Asn Ala Ala Ile Gln Ser Ala Ala Ile Ile Gly Ala
1               5                   10                  15

gga acg atg ggc aga ggc atc gct tat ctt ttc gcg caa aaa ggc att       96
Gly Thr Met Gly Arg Gly Ile Ala Tyr Leu Phe Ala Gln Lys Gly Ile
            20                  25                  30

ccc acg atg ctt tat aat cgc aac ggc aat acc ctc aat caa gct cgc      144
Pro Thr Met Leu Tyr Asn Arg Asn Gly Asn Thr Leu Asn Gln Ala Arg
        35                  40                  45

gaa tat atc gcg caa gac ctg aat aag aaa gtc gaa cag ggc aag atc      192
Glu Tyr Ile Ala Gln Asp Leu Asn Lys Lys Val Glu Gln Gly Lys Ile
    50                  55                  60

gcg ctg cgg gat aaa gac gcg gtg ctg gcc aat ctg atg ttc act tcc      240
Ala Leu Arg Asp Lys Asp Ala Val Leu Ala Asn Leu Met Phe Thr Ser
65                  70                  75                  80

gtg ttt gag gcc atc gcc gac agc gag ctg gtg ata gaa acc atc gcc      288
Val Phe Glu Ala Ile Ala Asp Ser Glu Leu Val Ile Glu Thr Ile Ala
                85                  90                  95

gag caa gaa caa acc aaa ctt gag gtg ctg gcg gcc atc gcc gca gtg      336
Glu Gln Glu Gln Thr Lys Leu Glu Val Leu Ala Ala Ile Ala Ala Val
            100                 105                 110

gtc aag ccc gac acg ctg atc gcc acc aat acc tcc tca ctg tcg ctc      384
Val Lys Pro Asp Thr Leu Ile Ala Thr Asn Thr Ser Ser Leu Ser Leu
        115                 120                 125

aac aag ctg gca acg gcg gta acg cac agc gaa cgc ttt atc ggt ttg      432
Asn Lys Leu Ala Thr Ala Val Thr His Ser Glu Arg Phe Ile Gly Leu
    130                 135                 140

cat ttt ttc aac ccc gcg ccg ctg atg aag ctg att gaa atc att ccg      480
His Phe Phe Asn Pro Ala Pro Leu Met Lys Leu Ile Glu Ile Ile Pro
145                 150                 155                 160

gcc tac ttt acc gcg cac gcc acc acg gaa cgc tgc cgc caa ctg gtg      528
Ala Tyr Phe Thr Ala His Ala Thr Thr Glu Arg Cys Arg Gln Leu Val
                165                 170                 175

gcg gcg ttg ggg aaa cgc gat gtc gtc tgc cag gcc acg ccg ggg ttc      576
Ala Ala Leu Gly Lys Arg Asp Val Val Cys Gln Ala Thr Pro Gly Phe
            180                 185                 190
```

-continued

```
atc gtc aat cgc atg gcc cgc ccc tac tac ctg gaa ggg ttc cgc ctg      624
Ile Val Asn Arg Met Ala Arg Pro Tyr Tyr Leu Glu Gly Phe Arg Leu
        195                 200                 205

ttg gaa gaa cat gtg gcg cgc gcg gcg cag atc gac cgc gcc ctc aaa      672
Leu Glu Glu His Val Ala Arg Ala Ala Gln Ile Asp Arg Ala Leu Lys
    210                 215                 220

gcc ggc ggg cgc ttc cgc atg ggg ccg ctc gag ctg acc gat ttt atc      720
Ala Gly Gly Arg Phe Arg Met Gly Pro Leu Glu Leu Thr Asp Phe Ile
225                 230                 235                 240

ggc caa gac atc aac tat cag gtc agc cgg caa atc tgg cag gac atg      768
Gly Gln Asp Ile Asn Tyr Gln Val Ser Arg Gln Ile Trp Gln Asp Met
                245                 250                 255

caa tac gac ccg cgc tat acc cct ggt cat ctg cag cgt tca ctg gtc      816
Gln Tyr Asp Pro Arg Tyr Thr Pro Gly His Leu Gln Arg Ser Leu Val
            260                 265                 270

gat gcc ggt ctg ttg ggg aaa aag aac ggc cgc tcc tat ttt gcc gcc      864
Asp Ala Gly Leu Leu Gly Lys Lys Asn Gly Arg Ser Tyr Phe Ala Ala
        275                 280                 285

gaa gaa acc gcc ccg ccg gtg acg gcc gcc aac aat gca gac gtc gag      912
Glu Glu Thr Ala Pro Pro Val Thr Ala Ala Asn Asn Ala Asp Val Glu
    290                 295                 300

acg ctg cgc gtt tac ggc gag cat cct ttt ttt acc ctg ttg cag cag      960
Thr Leu Arg Val Tyr Gly Glu His Pro Phe Phe Thr Leu Leu Gln Gln
305                 310                 315                 320

cga gcc gcg ctt cag tgg cca cag ctg cgc gtg gaa caa cgg ccg gca     1008
Arg Ala Ala Leu Gln Trp Pro Gln Leu Arg Val Glu Gln Arg Pro Ala
                325                 330                 335

tta ccg ggg ctg gga gcg gcc gtc cag atc aat gac gct ttc acc gtc     1056
Leu Pro Gly Leu Gly Ala Ala Val Gln Ile Asn Asp Ala Phe Thr Val
            340                 345                 350

agc atc acc gat ggc cgc acg gcg agc caa ctg gcc gag cag acg gca     1104
Ser Ile Thr Asp Gly Arg Thr Ala Ser Gln Leu Ala Glu Gln Thr Ala
        355                 360                 365

gcg gat gcc ttt gtg gtc gat ctc gcc ctg aac tac gcc gac acc acg     1152
Ala Asp Ala Phe Val Val Asp Leu Ala Leu Asn Tyr Ala Asp Thr Thr
    370                 375                 380

tat ctg gtg gcg gcg cac agc cgc cac gct tct gcg gcc aat aag gcg     1200
Tyr Leu Val Ala Ala His Ser Arg His Ala Ser Ala Ala Asn Lys Ala
385                 390                 395                 400

ctg ttt tta cgc ctg ctg cac acg gca atc cct cag gtt gaa ttt atc     1248
Leu Phe Leu Arg Leu Leu His Thr Ala Ile Pro Gln Val Glu Phe Ile
                405                 410                 415

aag gac tct ccg gcg ctt atc gtc gcc cgc gtc ctc agc agc ctg atc     1296
Lys Asp Ser Pro Ala Leu Ile Val Ala Arg Val Leu Ser Ser Leu Ile
            420                 425                 430

aat gag tcg gtg atc atg gtg gaa agc ggc gtc tgc agc cgg gaa gac     1344
Asn Glu Ser Val Ile Met Val Glu Ser Gly Val Cys Ser Arg Glu Asp
        435                 440                 445

atc gat gtc gcc gcc gtc gcg ggc gtt aac tac gcc ggc ggc att ttc     1392
Ile Asp Val Ala Ala Val Ala Gly Val Asn Tyr Ala Gly Gly Ile Phe
    450                 455                 460

gac tgg ctc ggc aaa ctg ggg gag aaa aac gtc agg acg acg ctg agc     1440
Asp Trp Leu Gly Lys Leu Gly Glu Lys Asn Val Arg Thr Thr Leu Ser
465                 470                 475                 480

aat ctg gcg cag ctg ctg cac gcg gcg cgc tat gcg ccg cat tac acc     1488
Asn Leu Ala Gln Leu Leu His Ala Ala Arg Tyr Ala Pro His Tyr Thr
                485                 490                 495

ctt ctg cac gcc gcg caa ccg gcg ctg acg acc acg cct taa             1530
Leu Leu His Ala Ala Gln Pro Ala Leu Thr Thr Thr Pro
```

-continued 500 505

<210> SEQ ID NO 12
<211> LENGTH: 509
<212> TYPE: PRT
<213> ORGANISM: Serratia nematodiphila DSM21420

<400> SEQUENCE: 12

Met Ala Glu Ser Asn Ala Ala Ile Gln Ser Ala Ala Ile Ile Gly Ala
1 5 10 15

Gly Thr Met Gly Arg Gly Ile Ala Tyr Leu Phe Ala Gln Lys Gly Ile
20 25 30

Pro Thr Met Leu Tyr Asn Arg Asn Gly Asn Thr Leu Asn Gln Ala Arg
35 40 45

Glu Tyr Ile Ala Gln Asp Leu Asn Lys Lys Val Glu Gln Gly Lys Ile
50 55 60

Ala Leu Arg Asp Lys Asp Ala Val Leu Ala Asn Leu Met Phe Thr Ser
65 70 75 80

Val Phe Glu Ala Ile Ala Asp Ser Glu Leu Val Ile Glu Thr Ile Ala
85 90 95

Glu Gln Glu Gln Thr Lys Leu Glu Val Leu Ala Ala Ile Ala Ala Val
100 105 110

Val Lys Pro Asp Thr Leu Ile Ala Thr Asn Thr Ser Ser Leu Ser Leu
115 120 125

Asn Lys Leu Ala Thr Ala Val Thr His Ser Glu Arg Phe Ile Gly Leu
130 135 140

His Phe Phe Asn Pro Ala Pro Leu Met Lys Leu Ile Glu Ile Ile Pro
145 150 155 160

Ala Tyr Phe Thr Ala His Ala Thr Thr Glu Arg Cys Arg Gln Leu Val
165 170 175

Ala Ala Leu Gly Lys Arg Asp Val Val Cys Gln Ala Thr Pro Gly Phe
180 185 190

Ile Val Asn Arg Met Ala Arg Pro Tyr Tyr Leu Glu Gly Phe Arg Leu
195 200 205

Leu Glu Glu His Val Ala Arg Ala Ala Gln Ile Asp Arg Ala Leu Lys
210 215 220

Ala Gly Gly Arg Phe Arg Met Gly Pro Leu Glu Leu Thr Asp Phe Ile
225 230 235 240

Gly Gln Asp Ile Asn Tyr Gln Val Ser Arg Gln Ile Trp Gln Asp Met
245 250 255

Gln Tyr Asp Pro Arg Tyr Thr Pro Gly His Leu Gln Arg Ser Leu Val
260 265 270

Asp Ala Gly Leu Leu Gly Lys Lys Asn Gly Arg Ser Tyr Phe Ala Ala
275 280 285

Glu Glu Thr Ala Pro Pro Val Thr Ala Ala Asn Asn Ala Asp Val Glu
290 295 300

Thr Leu Arg Val Tyr Gly Glu His Pro Phe Phe Thr Leu Leu Gln Gln
305 310 315 320

Arg Ala Ala Leu Gln Trp Pro Gln Leu Arg Val Glu Gln Arg Pro Ala
325 330 335

Leu Pro Gly Leu Gly Ala Ala Val Gln Ile Asn Asp Ala Phe Thr Val
340 345 350

Ser Ile Thr Asp Gly Arg Thr Ala Ser Gln Leu Ala Glu Gln Thr Ala
355 360 365

-continued

```
Ala Asp Ala Phe Val Val Asp Leu Ala Leu Asn Tyr Ala Asp Thr Thr
    370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Gly Gly Ile Phe
    450                 455                 460

Asp Trp Leu Gly Lys Leu Gly Glu Lys Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505


<210> SEQ ID NO 13
<211> LENGTH: 1530
<212> TYPE: DNA
<213> ORGANISM: Serratia plymuthica NBRC102599
<220> FEATURE:
<221> NAME/KEY: CDS
<222> LOCATION: (1)..(1530)

<400> SEQUENCE: 13

atg gca gag aat aat tcg gca atc cgt tca gcc gcc gtt att ggt gcg       48
Met Ala Glu Asn Asn Ser Ala Ile Arg Ser Ala Ala Val Ile Gly Ala
1               5                   10                  15

ggg acc atg ggc aga ggc atc gcc tat ctc ctg gcg ctg aac ggc ata       96
Gly Thr Met Gly Arg Gly Ile Ala Tyr Leu Leu Ala Leu Asn Gly Ile
            20                  25                  30

cga acc gta ctt tat aat cgc aat ggt aat aat ctc aat cag gcc cgt      144
Arg Thr Val Leu Tyr Asn Arg Asn Gly Asn Asn Leu Asn Gln Ala Arg
        35                  40                  45

gac tat att gtc agc gac ctg gac aga aaa ata gat aac gga aaa ata      192
Asp Tyr Ile Val Ser Asp Leu Asp Arg Lys Ile Asp Asn Gly Lys Ile
    50                  55                  60

acc ctg cag aaa aaa ggc cag ata tta gcc aat att att ttc tcg gac      240
Thr Leu Gln Lys Lys Gly Gln Ile Leu Ala Asn Ile Ile Phe Ser Asp
65                  70                  75                  80

gtc ttt gac gcc ata acc gac agc gat ctg gtg att gaa acc att gcg      288
Val Phe Asp Ala Ile Thr Asp Ser Asp Leu Val Ile Glu Thr Ile Ala
                85                  90                  95

gaa gat gag caa acc aag cat gaa atc ctg gca gcc att gcg gcg acg      336
Glu Asp Glu Gln Thr Lys His Glu Ile Leu Ala Ala Ile Ala Ala Thr
            100                 105                 110

gta aaa ccg gag gcg atc att gcg acc aat act tcc tct ctg tcg ctg      384
Val Lys Pro Glu Ala Ile Ile Ala Thr Asn Thr Ser Ser Leu Ser Leu
        115                 120                 125

aac aaa ctg gcg gcg ggg gtg gaa aac aac ccg cgc ttt atc ggc ctg      432
Asn Lys Leu Ala Ala Gly Val Glu Asn Asn Pro Arg Phe Ile Gly Leu
    130                 135                 140

cat ttt ttc aat ccg gcg ccg ctg atg aag ttg atc gaa att att ccc      480
His Phe Phe Asn Pro Ala Pro Leu Met Lys Leu Ile Glu Ile Ile Pro
145                 150                 155                 160

tct tat ttc acc tct cgc gcc acc agt cta cgc tgc cag cag ttg gta      528
```

-continued

```
Ser Tyr Phe Thr Ser Arg Ala Thr Ser Leu Arg Cys Gln Gln Leu Val
                165                 170                 175

aca gcg ttg ggt aaa cag ttt gtg gtc tgc aaa gcc acg ccg ggc ttt      576
Thr Ala Leu Gly Lys Gln Phe Val Val Cys Lys Ala Thr Pro Gly Phe
            180                 185                 190

att gtt aac cgc atg gcg cgg cct ttc tat ctg gaa ggg ttc cgg ctg      624
Ile Val Asn Arg Met Ala Arg Pro Phe Tyr Leu Glu Gly Phe Arg Leu
        195                 200                 205

ctg gag gaa aac gtg gcg ctg gcg cca cag atc gac cgc gcc ctc aag      672
Leu Glu Glu Asn Val Ala Leu Ala Pro Gln Ile Asp Arg Ala Leu Lys
    210                 215                 220

gcc ggc ggg cat ttt cgc atg ggg cct tta gaa ctg act gat ttt atc      720
Ala Gly Gly His Phe Arg Met Gly Pro Leu Glu Leu Thr Asp Phe Ile
225                 230                 235                 240

ggc cag gat atc aac tat cag gtc agc aag cag att tgg cag gat atg      768
Gly Gln Asp Ile Asn Tyr Gln Val Ser Lys Gln Ile Trp Gln Asp Met
                245                 250                 255

cag ttc gat ccc cgc tat acc ccc ggc cat ttg caa cgc tcg ctg gtg      816
Gln Phe Asp Pro Arg Tyr Thr Pro Gly His Leu Gln Arg Ser Leu Val
            260                 265                 270

gat gcc ggg ctg ctg ggg agg aaa aac ggg cgc tct ttt ttt gct tcc      864
Asp Ala Gly Leu Leu Gly Arg Lys Asn Gly Arg Ser Phe Phe Ala Ser
        275                 280                 285

caa cct gct aca cca ccc aac cca acc aca gag ggc gac acg cca act      912
Gln Pro Ala Thr Pro Pro Asn Pro Thr Thr Glu Gly Asp Thr Pro Thr
    290                 295                 300

tca ctg cat ttt tat ggt gaa cac gct tta ttc gat cac ctg caa cag      960
Ser Leu His Phe Tyr Gly Glu His Ala Leu Phe Asp His Leu Gln Gln
305                 310                 315                 320

cgc gct ttg gcc acc tgg cct gcg ctg cgc gtt cag cgg ttg ccg gaa     1008
Arg Ala Leu Ala Thr Trp Pro Ala Leu Arg Val Gln Arg Leu Pro Glu
                325                 330                 335

cgg ccg gaa ctg ggg cgt ttt atc ctg gtg aat aac agg ctg gcg atc     1056
Arg Pro Glu Leu Gly Arg Phe Ile Leu Val Asn Asn Arg Leu Ala Ile
            340                 345                 350

aaa atc act gat ggc aga acg gcg aac ctg ctc gcc ggc tta acc gct     1104
Lys Ile Thr Asp Gly Arg Thr Ala Asn Leu Leu Ala Gly Leu Thr Ala
        355                 360                 365

ctc gac acc ttc gtg att gac gcc gcg ctg aac tac gcc gac acc gcc     1152
Leu Asp Thr Phe Val Ile Asp Ala Ala Leu Asn Tyr Ala Asp Thr Ala
    370                 375                 380

tat ctg gtg gcc gcc cac aat caa cat gcc aca gag acg aat aaa gcg     1200
Tyr Leu Val Ala Ala His Asn Gln His Ala Thr Glu Thr Asn Lys Ala
385                 390                 395                 400

ctg ttt ctg acg ctg ctg caa acc ctc atc gct cag gtg gag ttt att     1248
Leu Phe Leu Thr Leu Leu Gln Thr Leu Ile Ala Gln Val Glu Phe Ile
                405                 410                 415

aaa gat tcc cct gcc ctg atc gtt gcc cgc gta ctg agc agc ctg atc     1296
Lys Asp Ser Pro Ala Leu Ile Val Ala Arg Val Leu Ser Ser Leu Ile
            420                 425                 430

aat gaa tcg gtg atc atg gtg gag agc ggc gtt tgc agc cgg gca gat     1344
Asn Glu Ser Val Ile Met Val Glu Ser Gly Val Cys Ser Arg Ala Asp
        435                 440                 445

atc gat atc gcc gcc gtg gcc ggc gtg aac tat gcc gac ggc att ttt     1392
Ile Asp Ile Ala Ala Val Ala Gly Val Asn Tyr Ala Asp Gly Ile Phe
    450                 455                 460

gcc tgg ttg gcg cag ctc ggg cag aaa aac gtg aaa tcg acg ctg gat     1440
Ala Trp Leu Ala Gln Leu Gly Gln Lys Asn Val Lys Ser Thr Leu Asp
465                 470                 475                 480
```

-continued

```
aac atg gcg caa ttg ctg cac tcc acg cgc tat tac ccg cat tac tca      1488
Asn Met Ala Gln Leu Leu His Ser Thr Arg Tyr Tyr Pro His Tyr Ser
                485                 490                 495

ttg ctg aac gcg gcc cgg cct gag ctg gct gta gcg ccc taa              1530
Leu Leu Asn Ala Ala Arg Pro Glu Leu Ala Val Ala Pro
            500                 505


<210> SEQ ID NO 14
<211> LENGTH: 509
<212> TYPE: PRT
<213> ORGANISM: Serratia plymuthica NBRC102599

<400> SEQUENCE: 14

Met Ala Glu Asn Asn Ser Ala Ile Arg Ser Ala Ala Val Ile Gly Ala
1               5                   10                  15

Gly Thr Met Gly Arg Gly Ile Ala Tyr Leu Leu Ala Leu Asn Gly Ile
            20                  25                  30

Arg Thr Val Leu Tyr Asn Arg Asn Gly Asn Asn Leu Asn Gln Ala Arg
        35                  40                  45

Asp Tyr Ile Val Ser Asp Leu Asp Arg Lys Ile Asp Asn Gly Lys Ile
    50                  55                  60

Thr Leu Gln Lys Lys Gly Gln Ile Leu Ala Asn Ile Ile Phe Ser Asp
65                  70                  75                  80

Val Phe Asp Ala Ile Thr Asp Ser Asp Leu Val Ile Glu Thr Ile Ala
                85                  90                  95

Glu Asp Glu Gln Thr Lys His Glu Ile Leu Ala Ala Ile Ala Ala Thr
            100                 105                 110

Val Lys Pro Glu Ala Ile Ile Ala Thr Asn Thr Ser Ser Leu Ser Leu
        115                 120                 125

Asn Lys Leu Ala Ala Gly Val Glu Asn Asn Pro Arg Phe Ile Gly Leu
    130                 135                 140

His Phe Phe Asn Pro Ala Pro Leu Met Lys Leu Ile Glu Ile Ile Pro
145                 150                 155                 160

Ser Tyr Phe Thr Ser Arg Ala Thr Ser Leu Arg Cys Gln Gln Leu Val
                165                 170                 175

Thr Ala Leu Gly Lys Gln Phe Val Val Cys Lys Ala Thr Pro Gly Phe
            180                 185                 190

Ile Val Asn Arg Met Ala Arg Pro Phe Tyr Leu Glu Gly Phe Arg Leu
        195                 200                 205

Leu Glu Glu Asn Val Ala Leu Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Lys Gln Ile Trp Gln Asp Met
                245                 250                 255

Gln Phe Asp Pro Arg Tyr Thr Pro Gly His Leu Gln Arg Ser Leu Val
            260                 265                 270

Asp Ala Gly Leu Leu Gly Arg Lys Asn Gly Arg Ser Phe Phe Ala Ser
        275                 280                 285

Gln Pro Ala Thr Pro Pro Asn Pro Thr Thr Glu Gly Asp Thr Pro Thr
    290                 295                 300

Ser Leu His Phe Tyr Gly Glu His Ala Leu Phe Asp His Leu Gln Gln
305                 310                 315                 320

Arg Ala Leu Ala Thr Trp Pro Ala Leu Arg Val Gln Arg Leu Pro Glu
                325                 330                 335
```

```
Arg Pro Glu Leu Gly Arg Phe Ile Leu Val Asn Asn Arg Leu Ala Ile
            340                 345                 350

Lys Ile Thr Asp Gly Arg Thr Ala Asn Leu Leu Ala Gly Leu Thr Ala
        355                 360                 365

Leu Asp Thr Phe Val Ile Asp Ala Ala Leu Asn Tyr Ala Asp Thr Ala
    370                 375                 380

Tyr Leu Val Ala Ala His Asn Gln His Ala Thr Glu Thr Asn Lys Ala
385                 390                 395                 400

Leu Phe Leu Thr Leu Leu Gln Thr Leu Ile Ala Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Ala Asp
        435                 440                 445

Ile Asp Ile Ala Ala Val Ala Gly Val Asn Tyr Ala Asp Gly Ile Phe
    450                 455                 460

Ala Trp Leu Ala Gln Leu Gly Gln Lys Asn Val Lys Ser Thr Leu Asp
465                 470                 475                 480

Asn Met Ala Gln Leu Leu His Ser Thr Arg Tyr Tyr Pro His Tyr Ser
                485                 490                 495

Leu Leu Asn Ala Ala Arg Pro Glu Leu Ala Val Ala Pro
            500                 505


<210> SEQ ID NO 15
<211> LENGTH: 1530
<212> TYPE: DNA
<213> ORGANISM: Serratia proteamaculans 568
<220> FEATURE:
<221> NAME/KEY: CDS
<222> LOCATION: (1)..(1530)

<400> SEQUENCE: 15

atg gca gag aat aat tcg gca atc cat tcg gtc gct gtt att ggt gcc       48
Met Ala Glu Asn Asn Ser Ala Ile His Ser Val Ala Val Ile Gly Ala
1               5                   10                  15

ggg acc atg ggc aga ggt att gcc tat ctt ctg gcg caa aac ggc ata       96
Gly Thr Met Gly Arg Gly Ile Ala Tyr Leu Leu Ala Gln Asn Gly Ile
            20                  25                  30

cga acc ctg ctt tat aat cgt agc ggt aat aat ctg aat cag gcc agg      144
Arg Thr Leu Leu Tyr Asn Arg Ser Gly Asn Asn Leu Asn Gln Ala Arg
        35                  40                  45

gac tat att att cgt gac ctg gat aag aaa ata gat ggc gga aaa ata      192
Asp Tyr Ile Ile Arg Asp Leu Asp Lys Lys Ile Asp Gly Gly Lys Ile
    50                  55                  60

agc ccg cag aaa aaa ggc gag ata ttg gcc aat ctg gtt ttc tct ccc      240
Ser Pro Gln Lys Lys Gly Glu Ile Leu Ala Asn Leu Val Phe Ser Pro
65                  70                  75                  80

att ttc gag gct att gcc gac agc gat ctg gtg att gaa acc atc gcg      288
Ile Phe Glu Ala Ile Ala Asp Ser Asp Leu Val Ile Glu Thr Ile Ala
                85                  90                  95

gaa cat gag gca acc aag cat gag atc ctc gcg gcg att gcg gcc acg      336
Glu His Glu Ala Thr Lys His Glu Ile Leu Ala Ala Ile Ala Ala Thr
            100                 105                 110

gtg aaa aaa gag gcg att atc gcc acc aat acc tcc tcg ctg tca ttg      384
Val Lys Lys Glu Ala Ile Ile Ala Thr Asn Thr Ser Ser Leu Ser Leu
        115                 120                 125

aat aag ctg gcc gca ggc gtc gaa aat aac gcc cgg ttt atc ggc ctg      432
Asn Lys Leu Ala Ala Gly Val Glu Asn Asn Ala Arg Phe Ile Gly Leu
    130                 135                 140
```

-continued

```
cac ttc ttc aat ccg gcc ccg ctg atg aaa ctg atc gaa att att ccg      480
His Phe Phe Asn Pro Ala Pro Leu Met Lys Leu Ile Glu Ile Ile Pro
145                 150                 155                 160

tct tac ttt acc agc cgg gcc acc agc ctg cgt tgc cag cag ttg gtg      528
Ser Tyr Phe Thr Ser Arg Ala Thr Ser Leu Arg Cys Gln Gln Leu Val
                165                 170                 175

acg gcg ata ggc aaa cag ttt gtg gtc tgc aaa gcc acg ccg ggc ttt      576
Thr Ala Ile Gly Lys Gln Phe Val Val Cys Lys Ala Thr Pro Gly Phe
            180                 185                 190

atc gtc aac cgg atg gcg cga cct ttt tat ctg gaa ggg ttc cgg ctg      624
Ile Val Asn Arg Met Ala Arg Pro Phe Tyr Leu Glu Gly Phe Arg Leu
        195                 200                 205

ttg gaa gag aac gtg gcg ctg gcg ccg cag atc gac cgc gca ctc aag      672
Leu Glu Glu Asn Val Ala Leu Ala Pro Gln Ile Asp Arg Ala Leu Lys
    210                 215                 220

gcc ggt ggc cac ttt cgc atg gga cct tta gag ctg acc gat ttt atc      720
Ala Gly Gly His Phe Arg Met Gly Pro Leu Glu Leu Thr Asp Phe Ile
225                 230                 235                 240

ggc cag gat att aac tat cag gtc agc agc cag att tgg cag gac atg      768
Gly Gln Asp Ile Asn Tyr Gln Val Ser Ser Gln Ile Trp Gln Asp Met
                245                 250                 255

cag tac gat ccc cgc tat acc ccc ggc cat ttg caa cgt tcg ctg gtg      816
Gln Tyr Asp Pro Arg Tyr Thr Pro Gly His Leu Gln Arg Ser Leu Val
            260                 265                 270

gat gcc ggg ctg ctg ggg aag aaa aac ggc cga tcc ttt ttt acc ccc      864
Asp Ala Gly Leu Leu Gly Lys Lys Asn Gly Arg Ser Phe Phe Thr Pro
        275                 280                 285

tct tcc gcc gaa ccc agc tcc gcc gat gca ggt agc ggc acg ccg acc      912
Ser Ser Ala Glu Pro Ser Ser Ala Asp Ala Gly Ser Gly Thr Pro Thr
    290                 295                 300

tca ctg aat ttt tat ggt gaa cat ccc ctg ttc gac ctg ttg caa cag      960
Ser Leu Asn Phe Tyr Gly Glu His Pro Leu Phe Asp Leu Leu Gln Gln
305                 310                 315                 320

cgc gct ttg gcg ctc tgg cca agg gtg cag att aat cgc caa tcg gaa     1008
Arg Ala Leu Ala Leu Trp Pro Arg Val Gln Ile Asn Arg Gln Ser Glu
                325                 330                 335

cag cca acg ctg ggc cgc ttt atc cgg gtg aat gac gca atg gcc atc     1056
Gln Pro Thr Leu Gly Arg Phe Ile Arg Val Asn Asp Ala Met Ala Ile
            340                 345                 350

aaa atc acc gat ggc cgc acc gcc aat ctg ctg gct gaa ttg acc gaa     1104
Lys Ile Thr Asp Gly Arg Thr Ala Asn Leu Leu Ala Glu Leu Thr Glu
        355                 360                 365

ctc gat acc ttc gtg atc gac gcc gcg ctc aac tac gcc gat acc gcc     1152
Leu Asp Thr Phe Val Ile Asp Ala Ala Leu Asn Tyr Ala Asp Thr Ala
    370                 375                 380

tat ctg gcg gct gcc cac agc cag gat gcc agc gcg gcc aat aaa gcg     1200
Tyr Leu Ala Ala Ala His Ser Gln Asp Ala Ser Ala Ala Asn Lys Ala
385                 390                 395                 400

ctg ttt ctg acg ctg ctg caa acg ttg atc ccg cag gtg gag ttt att     1248
Leu Phe Leu Thr Leu Leu Gln Thr Leu Ile Pro Gln Val Glu Phe Ile
                405                 410                 415

aaa gac tcc ccg ggc ctg att gtc gcc cgc gtc ctg agc agc ctg atc     1296
Lys Asp Ser Pro Gly Leu Ile Val Ala Arg Val Leu Ser Ser Leu Ile
            420                 425                 430

aat gag tcg gtg att atg gtg gag agc ggg gtt tgc agc cgg gcg gac     1344
Asn Glu Ser Val Ile Met Val Glu Ser Gly Val Cys Ser Arg Ala Asp
        435                 440                 445

atc gat atc gcc gcg gtg gcc ggc gtt aac tat gcc gat ggc atc ttt     1392
Ile Asp Ile Ala Ala Val Ala Gly Val Asn Tyr Ala Asp Gly Ile Phe
```

```
    450                 455                 460

agc tgg ctg gcg cag ctt ggg caa aaa aac gtg aag tcg acg ctg gac      1440
Ser Trp Leu Ala Gln Leu Gly Gln Lys Asn Val Lys Ser Thr Leu Asp
465                 470                 475                 480

aat atg gcg caa ctg ctg cat tcc gcc cgc tat tac ccg cat tac tct      1488
Asn Met Ala Gln Leu Leu His Ser Ala Arg Tyr Tyr Pro His Tyr Ser
                485                 490                 495

ttg ctc aat acc ccc cgg cca gag ctg gcc gtc gcg ccc taa              1530
Leu Leu Asn Thr Pro Arg Pro Glu Leu Ala Val Ala Pro
            500                 505


<210> SEQ ID NO 16
<211> LENGTH: 509
<212> TYPE: PRT
<213> ORGANISM: Serratia proteamaculans 568

<400> SEQUENCE: 16

Met Ala Glu Asn Asn Ser Ala Ile His Ser Val Ala Val Ile Gly Ala
1               5                   10                  15

Gly Thr Met Gly Arg Gly Ile Ala Tyr Leu Leu Ala Gln Asn Gly Ile
            20                  25                  30

Arg Thr Leu Leu Tyr Asn Arg Ser Gly Asn Asn Leu Asn Gln Ala Arg
        35                  40                  45

Asp Tyr Ile Ile Arg Asp Leu Asp Lys Lys Ile Asp Gly Gly Lys Ile
    50                  55                  60

Ser Pro Gln Lys Lys Gly Glu Ile Leu Ala Asn Leu Val Phe Ser Pro
65                  70                  75                  80

Ile Phe Glu Ala Ile Ala Asp Ser Asp Leu Val Ile Glu Thr Ile Ala
                85                  90                  95

Glu His Glu Ala Thr Lys His Glu Ile Leu Ala Ala Ile Ala Ala Thr
            100                 105                 110

Val Lys Lys Glu Ala Ile Ile Ala Thr Asn Thr Ser Ser Leu Ser Leu
        115                 120                 125

Asn Lys Leu Ala Ala Gly Val Glu Asn Asn Ala Arg Phe Ile Gly Leu
    130                 135                 140

His Phe Phe Asn Pro Ala Pro Leu Met Lys Leu Ile Glu Ile Ile Pro
145                 150                 155                 160

Ser Tyr Phe Thr Ser Arg Ala Thr Ser Leu Arg Cys Gln Gln Leu Val
                165                 170                 175

Thr Ala Ile Gly Lys Gln Phe Val Val Cys Lys Ala Thr Pro Gly Phe
            180                 185                 190

Ile Val Asn Arg Met Ala Arg Pro Phe Tyr Leu Glu Gly Phe Arg Leu
        195                 200                 205

Leu Glu Glu Asn Val Ala Leu Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Ser Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Phe Phe Thr Pro
        275                 280                 285

Ser Ser Ala Glu Pro Ser Ser Ala Asp Ala Gly Ser Gly Thr Pro Thr
    290                 295                 300
```

```
Ser Leu Asn Phe Tyr Gly Glu His Pro Leu Phe Asp Leu Leu Gln Gln
305                 310                 315                 320

Arg Ala Leu Ala Leu Trp Pro Arg Val Gln Ile Asn Arg Gln Ser Glu
                325                 330                 335

Gln Pro Thr Leu Gly Arg Phe Ile Arg Val Asn Asp Ala Met Ala Ile
            340                 345                 350

Lys Ile Thr Asp Gly Arg Thr Ala Asn Leu Leu Ala Glu Leu Thr Glu
        355                 360                 365

Leu Asp Thr Phe Val Ile Asp Ala Ala Leu Asn Tyr Ala Asp Thr Ala
    370                 375                 380

Tyr Leu Ala Ala Ala His Ser Gln Asp Ala Ser Ala Ala Asn Lys Ala
385                 390                 395                 400

Leu Phe Leu Thr Leu Leu Gln Thr Leu Ile Pro Gln Val Glu Phe Ile
                405                 410                 415

Lys Asp Ser Pro Gly Leu Ile Val Ala Arg Val Leu Ser Ser Leu Ile
            420                 425                 430

Asn Glu Ser Val Ile Met Val Glu Ser Gly Val Cys Ser Arg Ala Asp
        435                 440                 445

Ile Asp Ile Ala Ala Val Ala Gly Val Asn Tyr Ala Asp Gly Ile Phe
    450                 455                 460

Ser Trp Leu Ala Gln Leu Gly Gln Lys Asn Val Lys Ser Thr Leu Asp
465                 470                 475                 480

Asn Met Ala Gln Leu Leu His Ser Ala Arg Tyr Tyr Pro His Tyr Ser
                485                 490                 495

Leu Leu Asn Thr Pro Arg Pro Glu Leu Ala Val Ala Pro
            500                 505


<210> SEQ ID NO 17
<211> LENGTH: 1530
<212> TYPE: DNA
<213> ORGANISM: Serratia ureilytica Lr5/4
<220> FEATURE:
<221> NAME/KEY: CDS
<222> LOCATION: (1)..(1530)

<400> SEQUENCE: 17

atg gca gaa agt aat gcg gca att caa tcg gct gcg att atc ggc gcg      48
Met Ala Glu Ser Asn Ala Ala Ile Gln Ser Ala Ala Ile Ile Gly Ala
1               5                   10                  15

gga acg atg ggc aga ggc atc gct tat ctt ttg gcg caa aaa agc att      96
Gly Thr Met Gly Arg Gly Ile Ala Tyr Leu Leu Ala Gln Lys Ser Ile
            20                  25                  30

cgt acg gtg ctt tat aat cgc aac ggc aat acc ctc aat caa gct cgc     144
Arg Thr Val Leu Tyr Asn Arg Asn Gly Asn Thr Leu Asn Gln Ala Arg
        35                  40                  45

gac gct atc gtg caa gac ctg aac aaa aag gtg gaa cag ggc aag ctc     192
Asp Ala Ile Val Gln Asp Leu Asn Lys Lys Val Glu Gln Gly Lys Leu
    50                  55                  60

gcg ctg cag gac aaa gac gcg gtg ctg gct aat ctg acg ttc tcc gcg     240
Ala Leu Gln Asp Lys Asp Ala Val Leu Ala Asn Leu Thr Phe Ser Ala
65                  70                  75                  80

gaa ttt ggg gcc atc gcc gac agc gat ctg gtg atc gaa acc atc gca     288
Glu Phe Gly Ala Ile Ala Asp Ser Asp Leu Val Ile Glu Thr Ile Ala
                85                  90                  95

gag cat gag caa gcc aaa ctc gag gtg ctg gcg gcc atc gcc gcg acg     336
Glu His Glu Gln Ala Lys Leu Glu Val Leu Ala Ala Ile Ala Ala Thr
            100                 105                 110

gtc aag ccc gac acg ctg atc gcc acc aat acc tcc tca ctg tcg ctt     384
```

-continued

```
Val Lys Pro Asp Thr Leu Ile Ala Thr Asn Thr Ser Ser Leu Ser Leu
        115                 120                 125

aat aag ctg gcg acg gcg gtg acg cac agc gaa cgc ttt atc ggt ttg      432
Asn Lys Leu Ala Thr Ala Val Thr His Ser Glu Arg Phe Ile Gly Leu
    130                 135                 140

cac ttt ttc aac ccc gcg ccg ctg atg aag ctg att gaa atc att ccg      480
His Phe Phe Asn Pro Ala Pro Leu Met Lys Leu Ile Glu Ile Ile Pro
145                 150                 155                 160

gcc tat ttt acc gca cag gtc acc acc gaa cgt tgc cgt caa ctg gtg      528
Ala Tyr Phe Thr Ala Gln Val Thr Thr Glu Arg Cys Arg Gln Leu Val
                165                 170                 175

gcg gcg ttg ggg aaa cgc gat gtc gtc tgt cag gcc acg ccg gga ttt      576
Ala Ala Leu Gly Lys Arg Asp Val Val Cys Gln Ala Thr Pro Gly Phe
            180                 185                 190

atc gtc aac cgt atg gcc cgc ccc tac tat ctg gaa ggg ttc cgc ctg      624
Ile Val Asn Arg Met Ala Arg Pro Tyr Tyr Leu Glu Gly Phe Arg Leu
        195                 200                 205

ttg gaa gaa cac gtg gcg cgt gcg ccg cag atc gac cgc gcc ctc aaa      672
Leu Glu Glu His Val Ala Arg Ala Pro Gln Ile Asp Arg Ala Leu Lys
    210                 215                 220

gcc ggc gga cac ttt cgc atg ggg ccg ctc gaa ctg acc gat ttt atc      720
Ala Gly Gly His Phe Arg Met Gly Pro Leu Glu Leu Thr Asp Phe Ile
225                 230                 235                 240

ggt cag gac atc aac tat cag gtc agc cgg caa att tgg cag gac atg      768
Gly Gln Asp Ile Asn Tyr Gln Val Ser Arg Gln Ile Trp Gln Asp Met
                245                 250                 255

cag tac gat ccg cgc tat acc ccg ggc cat ctg cag cgc tcg ctg gtc      816
Gln Tyr Asp Pro Arg Tyr Thr Pro Gly His Leu Gln Arg Ser Leu Val
            260                 265                 270

gat gcc ggt ctg ttg ggc aaa aag aac ggc cgc tcc tat ttt tcc gcc      864
Asp Ala Gly Leu Leu Gly Lys Lys Asn Gly Arg Ser Tyr Phe Ser Ala
        275                 280                 285

gaa gaa tct cct ccg ccg ctt gcg gcc gcc gtc gat gcg gag gtc gag      912
Glu Glu Ser Pro Pro Pro Leu Ala Ala Ala Val Asp Ala Glu Val Glu
    290                 295                 300

acg cta cgc att tac ggt gaa cat cct ctc ttt act ctg cta cag cag      960
Thr Leu Arg Ile Tyr Gly Glu His Pro Leu Phe Thr Leu Leu Gln Gln
305                 310                 315                 320

cgg gcc acc ctg caa tgg ccg cgg ctg cgc gtg gaa caa cgg ccg aca     1008
Arg Ala Thr Leu Gln Trp Pro Arg Leu Arg Val Glu Gln Arg Pro Thr
                325                 330                 335

tta ccg ggc ctg ggc gcc gcc att cag gtt aat gac gct ttc acc gtc     1056
Leu Pro Gly Leu Gly Ala Ala Ile Gln Val Asn Asp Ala Phe Thr Val
            340                 345                 350

agc gtt acc gat ggc cgc acg gca aac cag ctt gcc gaa cag acc gcg     1104
Ser Val Thr Asp Gly Arg Thr Ala Asn Gln Leu Ala Glu Gln Thr Ala
        355                 360                 365

gcg gac gcc ttt gtc gtc gat gtc gcc ctg aac tac ggc gat acg gcg     1152
Ala Asp Ala Phe Val Val Asp Val Ala Leu Asn Tyr Gly Asp Thr Ala
    370                 375                 380

tac ctg gtg gcg gcg cat agc cgc cac gcc tct gca gcc aat aag gcg     1200
Tyr Leu Val Ala Ala His Ser Arg His Ala Ser Ala Ala Asn Lys Ala
385                 390                 395                 400

ctg ttt tta cgc ctg ctg cac acc gcg atc ccg cag gtg gaa ttt atc     1248
Leu Phe Leu Arg Leu Leu His Thr Ala Ile Pro Gln Val Glu Phe Ile
                405                 410                 415

aag gat tcc ccg gcc ttg atc gtc gcc cgc gtg ctc agc agc ctg atc     1296
Lys Asp Ser Pro Ala Leu Ile Val Ala Arg Val Leu Ser Ser Leu Ile
            420                 425                 430
```

-continued

```
aac gag tcg gtg atc atg gtg gaa agc ggc gtc tgc agc cgg gaa gac      1344
Asn Glu Ser Val Ile Met Val Glu Ser Gly Val Cys Ser Arg Glu Asp
        435                 440                 445

att gat gtc gcc gcc gtc gcc ggc gtg aac tac gcc gac ggt att ttc      1392
Ile Asp Val Ala Ala Val Ala Gly Val Asn Tyr Ala Asp Gly Ile Phe
    450                 455                 460

ggc tgg ctc act cgc ctc ggg gag gaa aat gtc agg acg acg ctg agc      1440
Gly Trp Leu Thr Arg Leu Gly Glu Glu Asn Val Arg Thr Thr Leu Ser
465                 470                 475                 480

aac ctg gcg caa ttg ctg cac gcg gcg cgc tat gcg ccg cat tac acc      1488
Asn Leu Ala Gln Leu Leu His Ala Ala Arg Tyr Ala Pro His Tyr Thr
                485                 490                 495

ctt ctg cac gcc gcc caa ccg gcg ctg acc acc acg cct taa              1530
Leu Leu His Ala Ala Gln Pro Ala Leu Thr Thr Thr Pro
            500                 505


<210> SEQ ID NO 18
<211> LENGTH: 509
<212> TYPE: PRT
<213> ORGANISM: Serratia ureilytica Lr5/4

<400> SEQUENCE: 18

Met Ala Glu Ser Asn Ala Ala Ile Gln Ser Ala Ala Ile Ile Gly Ala
1               5                   10                  15

Gly Thr Met Gly Arg Gly Ile Ala Tyr Leu Leu Ala Gln Lys Ser Ile
            20                  25                  30

Arg Thr Val Leu Tyr Asn Arg Asn Gly Asn Thr Leu Asn Gln Ala Arg
        35                  40                  45

Asp Ala Ile Val Gln Asp Leu Asn Lys Lys Val Glu Gln Gly Lys Leu
    50                  55                  60

Ala Leu Gln Asp Lys Asp Ala Val Leu Ala Asn Leu Thr Phe Ser Ala
65                  70                  75                  80

Glu Phe Gly Ala Ile Ala Asp Ser Asp Leu Val Ile Glu Thr Ile Ala
                85                  90                  95

Glu His Glu Gln Ala Lys Leu Glu Val Leu Ala Ala Ile Ala Ala Thr
            100                 105                 110

Val Lys Pro Asp Thr Leu Ile Ala Thr Asn Thr Ser Ser Leu Ser Leu
        115                 120                 125

Asn Lys Leu Ala Thr Ala Val Thr His Ser Glu Arg Phe Ile Gly Leu
    130                 135                 140

His Phe Phe Asn Pro Ala Pro Leu Met Lys Leu Ile Glu Ile Ile Pro
145                 150                 155                 160

Ala Tyr Phe Thr Ala Gln Val Thr Thr Glu Arg Cys Arg Gln Leu Val
                165                 170                 175

Ala Ala Leu Gly Lys Arg Asp Val Val Cys Gln Ala Thr Pro Gly Phe
            180                 185                 190

Ile Val Asn Arg Met Ala Arg Pro Tyr Tyr Leu Glu Gly Phe Arg Leu
        195                 200                 205

Leu Glu Glu His Val Ala Arg Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Arg Gln Ile Trp Gln Asp Met
                245                 250                 255

Gln Tyr Asp Pro Arg Tyr Thr Pro Gly His Leu Gln Arg Ser Leu Val
            260                 265                 270
```

-continued

```
Asp Ala Gly Leu Leu Gly Lys Lys Asn Gly Arg Ser Tyr Phe Ser Ala
        275                 280                 285

Glu Glu Ser Pro Pro Pro Leu Ala Ala Ala Val Asp Ala Glu Val Glu
    290                 295                 300

Thr Leu Arg Ile Tyr Gly Glu His Pro Leu Phe Thr Leu Leu Gln Gln
305                 310                 315                 320

Arg Ala Thr Leu Gln Trp Pro Arg Leu Arg Val Glu Gln Arg Pro Thr
                325                 330                 335

Leu Pro Gly Leu Gly Ala Ala Ile Gln Val Asn Asp Ala Phe Thr Val
            340                 345                 350

Ser Val Thr Asp Gly Arg Thr Ala Asn Gln Leu Ala Glu Gln Thr Ala
        355                 360                 365

Ala Asp Ala Phe Val Val Asp Val Ala Leu Asn Tyr Gly Asp Thr Ala
    370                 375                 380

Tyr Leu Val Ala Ala His Ser Arg His Ala Ser Ala Ala Asn Lys Ala
385                 390                 395                 400

Leu Phe Leu Arg Leu Leu His Thr Ala Ile Pro Gln Val Glu Phe Ile
                405                 410                 415

Lys Asp Ser Pro Ala Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Val Ala Ala Val Ala Gly Val Asn Tyr Ala Asp Gly Ile Phe
    450                 455                 460

Gly Trp Leu Thr Arg Leu Gly Glu Glu Asn Val Arg Thr Thr Leu Ser
465                 470                 475                 480

Asn Leu Ala Gln Leu Leu His Ala Ala Arg Tyr Ala Pro His Tyr Thr
                485                 490                 495

Leu Leu His Ala Ala Gln Pro Ala Leu Thr Thr Thr Pro
            500                 505


<210> SEQ ID NO 19
<211> LENGTH: 1530
<212> TYPE: DNA
<213> ORGANISM: Serratia sp. BW106
<220> FEATURE:
<221> NAME/KEY: CDS
<222> LOCATION: (1)..(1530)

<400> SEQUENCE: 19

atg gca gag aat aat tcg gca atc cat tcg gtc gct gtt att ggt gcc       48
Met Ala Glu Asn Asn Ser Ala Ile His Ser Val Ala Val Ile Gly Ala
1               5                   10                  15

gga acc atg ggc aga ggt att gcc tat ctt ctg gcg cag aac ggc ata       96
Gly Thr Met Gly Arg Gly Ile Ala Tyr Leu Leu Ala Gln Asn Gly Ile
            20                  25                  30

cga acc ctg ctt tat aat cgt agc ggt aat aat ctg gat cag gcc cgc      144
Arg Thr Leu Leu Tyr Asn Arg Ser Gly Asn Asn Leu Asp Gln Ala Arg
        35                  40                  45

gac tat att atc cgt gac ctg gat aag aaa ata gac aac ggg aaa ata      192
Asp Tyr Ile Ile Arg Asp Leu Asp Lys Lys Ile Asp Asn Gly Lys Ile
    50                  55                  60

agc caa cag aaa aaa ggc gaa gta ttg gcc aac ctg gtt ttc tct ccc      240
Ser Gln Gln Lys Lys Gly Glu Val Leu Ala Asn Leu Val Phe Ser Pro
65                  70                  75                  80

att ttc gac gct atc gcc gac agc gac ctg gtg att gaa acc atc gcg      288
Ile Phe Asp Ala Ile Ala Asp Ser Asp Leu Val Ile Glu Thr Ile Ala
                85                  90                  95
```

-continued

```
gag cat gag acc acc aag cat gaa atc ctc gcg gcg att gcg gcc acg      336
Glu His Glu Thr Thr Lys His Glu Ile Leu Ala Ala Ile Ala Ala Thr
            100                 105                 110

gtg aaa caa gag gcc att atc gcc acc aac acc tca tcg ctg tcg ttg      384
Val Lys Gln Glu Ala Ile Ile Ala Thr Asn Thr Ser Ser Leu Ser Leu
        115                 120                 125

aat aag ctg gcg gca ggc gtc gaa aac aac gcc cgt ttt atc ggc ctg      432
Asn Lys Leu Ala Ala Gly Val Glu Asn Asn Ala Arg Phe Ile Gly Leu
    130                 135                 140

cac ttc ttc aat ccg gcc ccg ctg atg aaa ctg atc gag att att ccg      480
His Phe Phe Asn Pro Ala Pro Leu Met Lys Leu Ile Glu Ile Ile Pro
145                 150                 155                 160

tcc tat ttt acc agc cgg gcc acc agc ctg cgc tgc cag cag ttg gtg      528
Ser Tyr Phe Thr Ser Arg Ala Thr Ser Leu Arg Cys Gln Gln Leu Val
                165                 170                 175

acg gcg cta ggc aaa cag ttt gtg gtc tgc aaa gcc acg ccg ggt ttt      576
Thr Ala Leu Gly Lys Gln Phe Val Val Cys Lys Ala Thr Pro Gly Phe
            180                 185                 190

atc gtc aac cgg atg gca cgg cct ttt tat ctg gaa gga ttc cgg ctg      624
Ile Val Asn Arg Met Ala Arg Pro Phe Tyr Leu Glu Gly Phe Arg Leu
        195                 200                 205

ttg gaa gaa aac gta gca ttg gca ccg cag atc gac cgc gcc ctc aag      672
Leu Glu Glu Asn Val Ala Leu Ala Pro Gln Ile Asp Arg Ala Leu Lys
    210                 215                 220

gcc ggt ggc cac ttt cgc atg ggc cct tta gag ctg acc gac ttt atc      720
Ala Gly Gly His Phe Arg Met Gly Pro Leu Glu Leu Thr Asp Phe Ile
225                 230                 235                 240

ggc cag gat att aac tat cag gtc agc agc cag att tgg cag gac atg      768
Gly Gln Asp Ile Asn Tyr Gln Val Ser Ser Gln Ile Trp Gln Asp Met
                245                 250                 255

cag tac gac cct cgc tat acc ccc ggc cat ttg caa cgt tcg ctg gtg      816
Gln Tyr Asp Pro Arg Tyr Thr Pro Gly His Leu Gln Arg Ser Leu Val
            260                 265                 270

gat gcc ggg ttg ttg ggg aag aaa aac ggc cga tcc ttt ttt gct gcc      864
Asp Ala Gly Leu Leu Gly Lys Lys Asn Gly Arg Ser Phe Phe Ala Ala
        275                 280                 285

cct tct tcc gaa tcg aac ccc ctc gac gca ggc aac ggc acg ctg act      912
Pro Ser Ser Glu Ser Asn Pro Leu Asp Ala Gly Asn Gly Thr Leu Thr
    290                 295                 300

tcc ctg cat ttt tat ggc gaa cat acc ctg ttt gac ctg ctg caa cag      960
Ser Leu His Phe Tyr Gly Glu His Thr Leu Phe Asp Leu Leu Gln Gln
305                 310                 315                 320

cgc gcc ttg gct atc tgg cca acg ctg cag att att cac cag ccg gaa     1008
Arg Ala Leu Ala Ile Trp Pro Thr Leu Gln Ile Ile His Gln Pro Glu
                325                 330                 335

cgg ccg acg ctg gga cgc ttt atc cgg gtg aat gac gca ttg gcc gtc     1056
Arg Pro Thr Leu Gly Arg Phe Ile Arg Val Asn Asp Ala Leu Ala Val
            340                 345                 350

aaa atc acc gat ggt cgc acc gcc aat ctg ctc gct gaa ttg acc gat     1104
Lys Ile Thr Asp Gly Arg Thr Ala Asn Leu Leu Ala Glu Leu Thr Asp
        355                 360                 365

ctc gac acc ttt gtg atc gac gcc gca ctg aat tac agc gat acc gcc     1152
Leu Asp Thr Phe Val Ile Asp Ala Ala Leu Asn Tyr Ser Asp Thr Ala
    370                 375                 380

tat ctg gtg gcc gcc cac aat cag gac gcc gcc gag gcc aat aaa gcg     1200
Tyr Leu Val Ala Ala His Asn Gln Asp Ala Ala Glu Ala Asn Lys Ala
385                 390                 395                 400

ctg ttt ctg tcg ctg ctg caa acg ttg atc ccg cag gtg gag ttt att     1248
Leu Phe Leu Ser Leu Leu Gln Thr Leu Ile Pro Gln Val Glu Phe Ile
```

-continued

```
                405                 410                 415

aaa gac tct cca ggc ctg atc gtc gcc cgg gtt ctg agc agt ctg atc     1296
Lys Asp Ser Pro Gly Leu Ile Val Ala Arg Val Leu Ser Ser Leu Ile
            420                 425                 430

aat gag tcg gtg atc atg gtg gag agc ggg gtt tgc agc cgg gca gat     1344
Asn Glu Ser Val Ile Met Val Glu Ser Gly Val Cys Ser Arg Ala Asp
        435                 440                 445

atc gat att gcc gcc gtg gcg ggc gtt aac tat gcc gat ggc atc ttt     1392
Ile Asp Ile Ala Ala Val Ala Gly Val Asn Tyr Ala Asp Gly Ile Phe
    450                 455                 460

gcc tgg ctg acg cag ctc ggg caa aaa aac gtg aaa tca acg ctg gat     1440
Ala Trp Leu Thr Gln Leu Gly Gln Lys Asn Val Lys Ser Thr Leu Asp
465                 470                 475                 480

aat atg gcg caa ctg ctg cat tcc gcc cgc tat tac ccg cat tac tca     1488
Asn Met Ala Gln Leu Leu His Ser Ala Arg Tyr Tyr Pro His Tyr Ser
                485                 490                 495

ttg ctg aat gcc ccc cgg ccc gaa ctg gcc gtc gcg ccg taa             1530
Leu Leu Asn Ala Pro Arg Pro Glu Leu Ala Val Ala Pro
            500                 505


<210> SEQ ID NO 20
<211> LENGTH: 509
<212> TYPE: PRT
<213> ORGANISM: Serratia sp. BW106

<400> SEQUENCE: 20

Met Ala Glu Asn Asn Ser Ala Ile His Ser Val Ala Val Ile Gly Ala
1               5                   10                  15

Gly Thr Met Gly Arg Gly Ile Ala Tyr Leu Leu Ala Gln Asn Gly Ile
            20                  25                  30

Arg Thr Leu Leu Tyr Asn Arg Ser Gly Asn Asn Leu Asp Gln Ala Arg
        35                  40                  45

Asp Tyr Ile Ile Arg Asp Leu Asp Lys Lys Ile Asp Asn Gly Lys Ile
    50                  55                  60

Ser Gln Gln Lys Lys Gly Glu Val Leu Ala Asn Leu Val Phe Ser Pro
65                  70                  75                  80

Ile Phe Asp Ala Ile Ala Asp Ser Asp Leu Val Ile Glu Thr Ile Ala
                85                  90                  95

Glu His Glu Thr Thr Lys His Glu Ile Leu Ala Ala Ile Ala Ala Thr
            100                 105                 110

Val Lys Gln Glu Ala Ile Ile Ala Thr Asn Thr Ser Ser Leu Ser Leu
        115                 120                 125

Asn Lys Leu Ala Ala Gly Val Glu Asn Asn Ala Arg Phe Ile Gly Leu
    130                 135                 140

His Phe Phe Asn Pro Ala Pro Leu Met Lys Leu Ile Glu Ile Ile Pro
145                 150                 155                 160

Ser Tyr Phe Thr Ser Arg Ala Thr Ser Leu Arg Cys Gln Gln Leu Val
                165                 170                 175

Thr Ala Leu Gly Lys Gln Phe Val Val Cys Lys Ala Thr Pro Gly Phe
            180                 185                 190

Ile Val Asn Arg Met Ala Arg Pro Phe Tyr Leu Glu Gly Phe Arg Leu
        195                 200                 205

Leu Glu Glu Asn Val Ala Leu Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240
```

-continued

```
Gly Gln Asp Ile Asn Tyr Gln Val Ser Ser Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Phe Phe Ala Ala
        275                 280                 285

Pro Ser Ser Glu Ser Asn Pro Leu Asp Ala Gly Asn Gly Thr Leu Thr
    290                 295                 300

Ser Leu His Phe Tyr Gly Glu His Thr Leu Phe Asp Leu Leu Gln Gln
305                 310                 315                 320

Arg Ala Leu Ala Ile Trp Pro Thr Leu Gln Ile Ile His Gln Pro Glu
                325                 330                 335

Arg Pro Thr Leu Gly Arg Phe Ile Arg Val Asn Asp Ala Leu Ala Val
            340                 345                 350

Lys Ile Thr Asp Gly Arg Thr Ala Asn Leu Leu Ala Glu Leu Thr Asp
        355                 360                 365

Leu Asp Thr Phe Val Ile Asp Ala Ala Leu Asn Tyr Ser Asp Thr Ala
    370                 375                 380

Tyr Leu Val Ala Ala His Asn Gln Asp Ala Ala Glu Ala Asn Lys Ala
385                 390                 395                 400

Leu Phe Leu Ser Leu Leu Gln Thr Leu Ile Pro Gln Val Glu Phe Ile
                405                 410                 415

Lys Asp Ser Pro Gly Leu Ile Val Ala Arg Val Leu Ser Ser Leu Ile
            420                 425                 430

Asn Glu Ser Val Ile Met Val Glu Ser Gly Val Cys Ser Arg Ala Asp
        435                 440                 445

Ile Asp Ile Ala Ala Val Ala Gly Val Asn Tyr Ala Asp Gly Ile Phe
    450                 455                 460

Ala Trp Leu Thr Gln Leu Gly Gln Lys Asn Val Lys Ser Thr Leu Asp
465                 470                 475                 480

Asn Met Ala Gln Leu Leu His Ser Ala Arg Tyr Tyr Pro His Tyr Ser
                485                 490                 495

Leu Leu Asn Ala Pro Arg Pro Glu Leu Ala Val Ala Pro
            500                 505


<210> SEQ ID NO 21
<211> LENGTH: 1530
<212> TYPE: DNA
<213> ORGANISM: Serratia liquefaciens FK01
<220> FEATURE:
<221> NAME/KEY: CDS
<222> LOCATION: (1)..(1530)

<400> SEQUENCE: 21

atg gca gag aat aat acg gca ata gat tcg gtc gcc gtg att ggc gcc       48
Met Ala Glu Asn Asn Thr Ala Ile Asp Ser Val Ala Val Ile Gly Ala
1               5                   10                  15

gga acc atg ggc aga ggc att gcc tat ctt ttg gca ctg aac ggc ata       96
Gly Thr Met Gly Arg Gly Ile Ala Tyr Leu Leu Ala Leu Asn Gly Ile
            20                  25                  30

cga acc ctg ctt tat aat cga aac ggt aat cat ctt aac cag gcc cgg      144
Arg Thr Leu Leu Tyr Asn Arg Asn Gly Asn His Leu Asn Gln Ala Arg
        35                  40                  45

gat tat att gtc ggc gac ctg gat aaa aaa atc gac aac gga aaa ata      192
Asp Tyr Ile Val Gly Asp Leu Asp Lys Lys Ile Asp Asn Gly Lys Ile
    50                  55                  60

agc caa cag aaa aag ggc gag gtc ctg gcc aat ctg gtt ttc tcg cca      240
```

```
Ser Gln Gln Lys Lys Gly Glu Val Leu Ala Asn Leu Val Phe Ser Pro
65                  70                  75                  80

gtt ttc gac gcc att gcc gac agt gac ctg gtg att gaa acc ata gcg      288
Val Phe Asp Ala Ile Ala Asp Ser Asp Leu Val Ile Glu Thr Ile Ala
                85                  90                  95

gaa cat gaa ccc acc aag cat gag atc ctc gcg gcc att gcc gcc acg      336
Glu His Glu Pro Thr Lys His Glu Ile Leu Ala Ala Ile Ala Ala Thr
            100                 105                 110

gta aaa aaa gag gcg att atc gcc acc aat acc tct tcg ctg tcg ctg      384
Val Lys Lys Glu Ala Ile Ile Ala Thr Asn Thr Ser Ser Leu Ser Leu
        115                 120                 125

aat aaa ctg gcc gca ggg ata gaa aac aac tcg cgc ttt atc ggc ctg      432
Asn Lys Leu Ala Ala Gly Ile Glu Asn Asn Ser Arg Phe Ile Gly Leu
    130                 135                 140

cat ttc ttc aac ccg gca ccg ctg atg aag ctg atc gaa att atc ccg      480
His Phe Phe Asn Pro Ala Pro Leu Met Lys Leu Ile Glu Ile Ile Pro
145                 150                 155                 160

tcc tat ttt acc gcc cgg gcc acc acc tta cgc tgc cag cag ttg gtc      528
Ser Tyr Phe Thr Ala Arg Ala Thr Thr Leu Arg Cys Gln Gln Leu Val
                165                 170                 175

acg gcg ata ggc aaa aaa ttt gtg gtc tgc aaa gcc acg ccg ggc ttt      576
Thr Ala Ile Gly Lys Lys Phe Val Val Cys Lys Ala Thr Pro Gly Phe
            180                 185                 190

atc gtc aat cgc atg gcg cgg cct ttt tat ctg gaa ggt ttt cgc ctg      624
Ile Val Asn Arg Met Ala Arg Pro Phe Tyr Leu Glu Gly Phe Arg Leu
        195                 200                 205

ctg gag gaa aac gtg gcg ctg gca ccg caa atc gac cgc gcg ctc aag      672
Leu Glu Glu Asn Val Ala Leu Ala Pro Gln Ile Asp Arg Ala Leu Lys
    210                 215                 220

gcc gga ggc cac ttc cgc atg ggg cct ttg gaa ctg act gat ttt att      720
Ala Gly Gly His Phe Arg Met Gly Pro Leu Glu Leu Thr Asp Phe Ile
225                 230                 235                 240

ggt cag gac att aat tat cag gtc agc agc cag att tgg cag gac atg      768
Gly Gln Asp Ile Asn Tyr Gln Val Ser Ser Gln Ile Trp Gln Asp Met
                245                 250                 255

cag tat gac ccc cgc tat acc ccc ggc cat ttg caa cgt tcg ctg gtg      816
Gln Tyr Asp Pro Arg Tyr Thr Pro Gly His Leu Gln Arg Ser Leu Val
            260                 265                 270

gat gcc ggg ctg ttg ggg aag aaa aac ggg cgc tct ttt ttt tcc ccc      864
Asp Ala Gly Leu Leu Gly Lys Lys Asn Gly Arg Ser Phe Phe Ser Pro
        275                 280                 285

tcg gct gac gcc gcc aac cca ccg gct acc ggc ggc ggt acg ctg agc      912
Ser Ala Asp Ala Ala Asn Pro Pro Ala Thr Gly Gly Gly Thr Leu Ser
    290                 295                 300

tcg ctg cat ttt ttt ggc gaa cat ccg ctg ttt gat ctg ctg caa cag      960
Ser Leu His Phe Phe Gly Glu His Pro Leu Phe Asp Leu Leu Gln Gln
305                 310                 315                 320

cac gcc ttc gca acc tgg gcg ccc ctg gca ata aca cgt cag ccg gaa     1008
His Ala Phe Ala Thr Trp Ala Pro Leu Ala Ile Thr Arg Gln Pro Glu
                325                 330                 335

cac ccg gtt ctg ggc cgt ttt atc cag gtg aat gac agt ctg gca gtc     1056
His Pro Val Leu Gly Arg Phe Ile Gln Val Asn Asp Ser Leu Ala Val
            340                 345                 350

aaa atc acc gac ggg cga acg gcc aat cag ctt gcc gag ctg gcg ggt     1104
Lys Ile Thr Asp Gly Arg Thr Ala Asn Gln Leu Ala Glu Leu Ala Gly
        355                 360                 365

ctc gat acc ttc gtg gtc gac gtt gca ctg aac tat gcc aac acc gct     1152
Leu Asp Thr Phe Val Val Asp Val Ala Leu Asn Tyr Ala Asn Thr Ala
    370                 375                 380
```

-continued

```
ttt ctg gtg gcg gcc cac agc caa cag gct acc gag gcg aat aaa gag      1200
Phe Leu Val Ala Ala His Ser Gln Gln Ala Thr Glu Ala Asn Lys Glu
385                 390                 395                 400

ctg ttc ctc acg ctg ctg caa acg gtg atc ccg cag gtg gag ttt gtt      1248
Leu Phe Leu Thr Leu Leu Gln Thr Val Ile Pro Gln Val Glu Phe Val
                405                 410                 415

aaa gat tcc cca ggc ctg atc gtc gcc cgg gtt ctg agc agc ctg atc      1296
Lys Asp Ser Pro Gly Leu Ile Val Ala Arg Val Leu Ser Ser Leu Ile
            420                 425                 430

aat gag tcg gtg atc atg gtg gag agc ggg gtt tgt agc cga gaa gac      1344
Asn Glu Ser Val Ile Met Val Glu Ser Gly Val Cys Ser Arg Glu Asp
        435                 440                 445

atc gat atc gcc gcc gtg gcc ggc gtc aac tat gcc gac ggc att ttt      1392
Ile Asp Ile Ala Ala Val Ala Gly Val Asn Tyr Ala Asp Gly Ile Phe
    450                 455                 460

gcc tgg ctg gcg cag ctc ggg cag aaa aac gtg aaa tcg acg ctg gat      1440
Ala Trp Leu Ala Gln Leu Gly Gln Lys Asn Val Lys Ser Thr Leu Asp
465                 470                 475                 480

aat atg gcg caa ctg ctg cat tcc gcc cgc tat tac ccg cac tac tcg      1488
Asn Met Ala Gln Leu Leu His Ser Ala Arg Tyr Tyr Pro His Tyr Ser
                485                 490                 495

ttg ctc cac gct acc agg ccc gag ctg gcc gtc gcg cca tga              1530
Leu Leu His Ala Thr Arg Pro Glu Leu Ala Val Ala Pro
            500                 505


<210> SEQ ID NO 22
<211> LENGTH: 509
<212> TYPE: PRT
<213> ORGANISM: Serratia liquefaciens FK01

<400> SEQUENCE: 22

Met Ala Glu Asn Asn Thr Ala Ile Asp Ser Val Ala Val Ile Gly Ala
1               5                   10                  15

Gly Thr Met Gly Arg Gly Ile Ala Tyr Leu Leu Ala Leu Asn Gly Ile
            20                  25                  30

Arg Thr Leu Leu Tyr Asn Arg Asn Gly Asn His Leu Asn Gln Ala Arg
        35                  40                  45

Asp Tyr Ile Val Gly Asp Leu Asp Lys Lys Ile Asp Asn Gly Lys Ile
    50                  55                  60

Ser Gln Gln Lys Lys Gly Glu Val Leu Ala Asn Leu Val Phe Ser Pro
65                  70                  75                  80

Val Phe Asp Ala Ile Ala Asp Ser Asp Leu Val Ile Glu Thr Ile Ala
                85                  90                  95

Glu His Glu Pro Thr Lys His Glu Ile Leu Ala Ala Ile Ala Ala Thr
            100                 105                 110

Val Lys Lys Glu Ala Ile Ile Ala Thr Asn Thr Ser Ser Leu Ser Leu
        115                 120                 125

Asn Lys Leu Ala Ala Gly Ile Glu Asn Asn Ser Arg Phe Ile Gly Leu
    130                 135                 140

His Phe Phe Asn Pro Ala Pro Leu Met Lys Leu Ile Glu Ile Ile Pro
145                 150                 155                 160

Ser Tyr Phe Thr Ala Arg Ala Thr Thr Leu Arg Cys Gln Gln Leu Val
                165                 170                 175

Thr Ala Ile Gly Lys Lys Phe Val Val Cys Lys Ala Thr Pro Gly Phe
            180                 185                 190

Ile Val Asn Arg Met Ala Arg Pro Phe Tyr Leu Glu Gly Phe Arg Leu
        195                 200                 205
```

```
Leu Glu Glu Asn Val Ala Leu Ala Pro Gln Ile Asp Arg Ala Leu Lys
    210                 215                 220

Ala Gly Gly His Phe Arg Met Gly Pro Leu Glu Leu Thr Asp Phe Ile
225                 230                 235                 240

Gly Gln Asp Ile Asn Tyr Gln Val Ser Ser Gln Ile Trp Gln Asp Met
                245                 250                 255

Gln Tyr Asp Pro Arg Tyr Thr Pro Gly His Leu Gln Arg Ser Leu Val
            260                 265                 270

Asp Ala Gly Leu Leu Gly Lys Lys Asn Gly Arg Ser Phe Phe Ser Pro
        275                 280                 285

Ser Ala Asp Ala Ala Asn Pro Pro Ala Thr Gly Gly Gly Thr Leu Ser
    290                 295                 300

Ser Leu His Phe Phe Gly Glu His Pro Leu Phe Asp Leu Leu Gln Gln
305                 310                 315                 320

His Ala Phe Ala Thr Trp Ala Pro Leu Ala Ile Thr Arg Gln Pro Glu
                325                 330                 335

His Pro Val Leu Gly Arg Phe Ile Gln Val Asn Asp Ser Leu Ala Val
            340                 345                 350

Lys Ile Thr Asp Gly Arg Thr Ala Asn Gln Leu Ala Glu Leu Ala Gly
        355                 360                 365

Leu Asp Thr Phe Val Val Asp Val Ala Leu Asn Tyr Ala Asn Thr Ala
    370                 375                 380

Phe Leu Val Ala Ala His Ser Gln Gln Ala Thr Glu Ala Asn Lys Glu
385                 390                 395                 400

Leu Phe Leu Thr Leu Leu Gln Thr Val Ile Pro Gln Val Glu Phe Val
                405                 410                 415

Lys Asp Ser Pro Gly Leu Ile Val Ala Arg Val Leu Ser Ser Leu Ile
            420                 425                 430

Asn Glu Ser Val Ile Met Val Glu Ser Gly Val Cys Ser Arg Glu Asp
        435                 440                 445

Ile Asp Ile Ala Ala Val Ala Gly Val Asn Tyr Ala Asp Gly Ile Phe
    450                 455                 460

Ala Trp Leu Ala Gln Leu Gly Gln Lys Asn Val Lys Ser Thr Leu Asp
465                 470                 475                 480

Asn Met Ala Gln Leu Leu His Ser Ala Arg Tyr Tyr Pro His Tyr Ser
                485                 490                 495

Leu Leu His Ala Thr Arg Pro Glu Leu Ala Val Ala Pro
            500                 505
```

<210> SEQ ID NO 23
<211> LENGTH: 24
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)

-continued

<223> OTHER INFORMATION: Xaa can be any naturally occurring amino acid

<400> SEQUENCE: 23

Gly Ala Gly Thr Met Gly Arg Gly Ile Ala Tyr Leu Xaa Ala Xaa Xaa
1               5                   10                  15

Xaa Ile Xaa Thr Xaa Leu Tyr Asn
            20

<210> SEQ ID NO 24
<211> LENGTH: 55
<212> TYPE: DNA
<213> ORGANISM: Artificial Sequence
<220> FEATURE:
<223> OTHER INFORMATION: primer

<400> SEQUENCE: 24
gagcgggttt gagttcaatt gtagctggtg gaatatttga tcaataaaac gtacg          55

<210> SEQ ID NO 25
<211> LENGTH: 34
<212> TYPE: DNA
<213> ORGANISM: Artificial Sequence
<220> FEATURE:
<223> OTHER INFORMATION: primer

<400> SEQUENCE: 25
gagtcattaa gtgtttcact tgatcagcgg cacg                                 34

<210> SEQ ID NO 26
<211> LENGTH: 1413
<212> TYPE: DNA
<213> ORGANISM: Escherichia coli str. K-12 substr. MG1655
<220> FEATURE:
<221> NAME/KEY: CDS
<222> LOCATION: (1)..(1413)

<400> SEQUENCE: 26 atg aaa aag acc aaa att gtt tgc acc atc gga ccg aaa acc gaa tct       48
Met Lys Lys Thr Lys Ile Val Cys Thr Ile Gly Pro Lys Thr Glu Ser
1               5                   10                  15 gaa gag atg tta gct aaa atg ctg gac gct ggc atg aac gtt atg cgt       96
Glu Glu Met Leu Ala Lys Met Leu Asp Ala Gly Met Asn Val Met Arg
            20                  25                  30 ctg aac ttc tct cat ggt gac tat gca gaa cac ggt cag cgc att cag      144
Leu Asn Phe Ser His Gly Asp Tyr Ala Glu His Gly Gln Arg Ile Gln
        35                  40                  45 aat ctg cgc aac gtg atg agc aaa act ggt aaa acc gcc gct atc ctg      192
Asn Leu Arg Asn Val Met Ser Lys Thr Gly Lys Thr Ala Ala Ile Leu
    50                  55                  60 ctt gat acc aaa ggt ccg gaa atc cgc acc atg aaa ctg gaa ggc ggt      240
Leu Asp Thr Lys Gly Pro Glu Ile Arg Thr Met Lys Leu Glu Gly Gly
65                  70                  75                  80 aac gac gtt tct ctg aaa gct ggt cag acc ttt act ttc acc act gat      288
Asn Asp Val Ser Leu Lys Ala Gly Gln Thr Phe Thr Phe Thr Thr Asp
                85                  90                  95 aaa tct gtt atc ggc aac agc gaa atg gtt gcg gta acg tat gaa ggt      336
Lys Ser Val Ile Gly Asn Ser Glu Met Val Ala Val Thr Tyr Glu Gly
            100                 105                 110 ttc act act gac ctg tct gtt ggc aac acc gta ctg gtt gac gat ggt      384
Phe Thr Thr Asp Leu Ser Val Gly Asn Thr Val Leu Val Asp Asp Gly
        115                 120                 125 ctg atc ggt atg gaa gtt acc gcc att gaa ggt aac aaa gtt atc tgt      432
Leu Ile Gly Met Glu Val Thr Ala Ile Glu Gly Asn Lys Val Ile Cys -continued

```
    130                 135                 140

aaa gtg ctg aac aac ggt gac ctg ggc gaa aac aaa ggt gtg aac ctg      480
Lys Val Leu Asn Asn Gly Asp Leu Gly Glu Asn Lys Gly Val Asn Leu
145                 150                 155                 160

cct ggc gtt tcc att gct ctg cca gca ctg gct gaa aaa gac aaa cag      528
Pro Gly Val Ser Ile Ala Leu Pro Ala Leu Ala Glu Lys Asp Lys Gln
                165                 170                 175

gac ctg atc ttt ggt tgc gaa caa ggc gta gac ttt gtt gct gct tcc      576
Asp Leu Ile Phe Gly Cys Glu Gln Gly Val Asp Phe Val Ala Ala Ser
            180                 185                 190

ttt att cgt aag cgt tct gac gtt atc gaa atc cgt gag cac ctg aaa      624
Phe Ile Arg Lys Arg Ser Asp Val Ile Glu Ile Arg Glu His Leu Lys
        195                 200                 205

gcg cac ggc ggc gaa aac atc cac atc atc tcc aaa atc gaa aac cag      672
Ala His Gly Gly Glu Asn Ile His Ile Ile Ser Lys Ile Glu Asn Gln
    210                 215                 220

gaa ggc ctc aac aac ttc gac gaa atc ctc gaa gcc tct gac ggc atc      720
Glu Gly Leu Asn Asn Phe Asp Glu Ile Leu Glu Ala Ser Asp Gly Ile
225                 230                 235                 240

atg gtt gcg cgt ggc gac ctg ggt gta gaa atc ccg gta gaa gaa gtt      768
Met Val Ala Arg Gly Asp Leu Gly Val Glu Ile Pro Val Glu Glu Val
                245                 250                 255

atc ttc gcc cag aag atg atg atc gaa aaa tgt atc cgt gca cgt aaa      816
Ile Phe Ala Gln Lys Met Met Ile Glu Lys Cys Ile Arg Ala Arg Lys
            260                 265                 270

gtc gtt atc act gcg acc cag atg ctg gat tcc atg atc aaa aac cca      864
Val Val Ile Thr Ala Thr Gln Met Leu Asp Ser Met Ile Lys Asn Pro
        275                 280                 285

cgc ccg act cgc gca gaa gcc ggt gac gtt gca aac gcc atc ctc gac      912
Arg Pro Thr Arg Ala Glu Ala Gly Asp Val Ala Asn Ala Ile Leu Asp
    290                 295                 300

ggt act gac gca gtg atg ctg tct ggt gaa tcc gca aaa ggt aaa tac      960
Gly Thr Asp Ala Val Met Leu Ser Gly Glu Ser Ala Lys Gly Lys Tyr
305                 310                 315                 320

ccg ctg gaa gcg gtt tct atc atg gcg acc atc tgc gaa cgt acc gac     1008
Pro Leu Glu Ala Val Ser Ile Met Ala Thr Ile Cys Glu Arg Thr Asp
                325                 330                 335

cgc gtg atg aac agc cgt ctc gag ttc aac aat gac aac cgt aaa ctg     1056
Arg Val Met Asn Ser Arg Leu Glu Phe Asn Asn Asp Asn Arg Lys Leu
            340                 345                 350

cgc att acc gaa gcg gta tgc cgt ggt gcc gtt gaa act gct gaa aaa     1104
Arg Ile Thr Glu Ala Val Cys Arg Gly Ala Val Glu Thr Ala Glu Lys
        355                 360                 365

ctg gat gct ccg ctg atc gtg gtt gct act cag ggc ggt aaa tct gct     1152
Leu Asp Ala Pro Leu Ile Val Val Ala Thr Gln Gly Gly Lys Ser Ala
    370                 375                 380

cgc gca gta cgt aaa tac ttc ccg gat gcc acc atc ctg gca ctg acc     1200
Arg Ala Val Arg Lys Tyr Phe Pro Asp Ala Thr Ile Leu Ala Leu Thr
385                 390                 395                 400

acc aac gaa aaa acg gct cat cag ttg gta ctg agc aaa ggc gtt gtg     1248
Thr Asn Glu Lys Thr Ala His Gln Leu Val Leu Ser Lys Gly Val Val
                405                 410                 415

ccg cag ctt gtt aaa gag atc act tct act gat gat ttc tac cgt ctg     1296
Pro Gln Leu Val Lys Glu Ile Thr Ser Thr Asp Asp Phe Tyr Arg Leu
            420                 425                 430

ggt aaa gaa ctg gct ctg cag agc ggt ctg gca cac aaa ggt gac gtt     1344
Gly Lys Glu Leu Ala Leu Gln Ser Gly Leu Ala His Lys Gly Asp Val
        435                 440                 445

gta gtt atg gtt tct ggt gca ctg gta ccg agc ggc act act aac acc     1392
```

-continued

```
Val Val Met Val Ser Gly Ala Leu Val Pro Ser Gly Thr Thr Asn Thr
    450                 455                 460

gca tct gtt cac gtc ctg taa                                          1413
Ala Ser Val His Val Leu
465                 470


<210> SEQ ID NO 27
<211> LENGTH: 470
<212> TYPE: PRT
<213> ORGANISM: Escherichia coli str. K-12 substr. MG1655

<400> SEQUENCE: 27

Met Lys Lys Thr Lys Ile Val Cys Thr Ile Gly Pro Lys Thr Glu Ser
1               5                   10                  15

Glu Glu Met Leu Ala Lys Met Leu Asp Ala Gly Met Asn Val Met Arg
            20                  25                  30

Leu Asn Phe Ser His Gly Asp Tyr Ala Glu His Gly Gln Arg Ile Gln
        35                  40                  45

Asn Leu Arg Asn Val Met Ser Lys Thr Gly Lys Thr Ala Ala Ile Leu
    50                  55                  60

Leu Asp Thr Lys Gly Pro Glu Ile Arg Thr Met Lys Leu Glu Gly Gly
65                  70                  75                  80

Asn Asp Val Ser Leu Lys Ala Gly Gln Thr Phe Thr Phe Thr Thr Asp
                85                  90                  95

Lys Ser Val Ile Gly Asn Ser Glu Met Val Ala Val Thr Tyr Glu Gly
            100                 105                 110

Phe Thr Thr Asp Leu Ser Val Gly Asn Thr Val Leu Val Asp Asp Gly
        115                 120                 125

Leu Ile Gly Met Glu Val Thr Ala Ile Glu Gly Asn Lys Val Ile Cys
    130                 135                 140

Lys Val Leu Asn Asn Gly Asp Leu Gly Glu Asn Lys Gly Val Asn Leu
145                 150                 155                 160

Pro Gly Val Ser Ile Ala Leu Pro Ala Leu Ala Glu Lys Asp Lys Gln
                165                 170                 175

Asp Leu Ile Phe Gly Cys Glu Gln Gly Val Asp Phe Val Ala Ala Ser
            180                 185                 190

Phe Ile Arg Lys Arg Ser Asp Val Ile Glu Ile Arg Glu His Leu Lys
        195                 200                 205

Ala His Gly Gly Glu Asn Ile His Ile Ile Ser Lys Ile Glu Asn Gln
    210                 215                 220

Glu Gly Leu Asn Asn Phe Asp Glu Ile Leu Glu Ala Ser Asp Gly Ile
225                 230                 235                 240

Met Val Ala Arg Gly Asp Leu Gly Val Glu Ile Pro Val Glu Glu Val
                245                 250                 255

Ile Phe Ala Gln Lys Met Met Ile Glu Lys Cys Ile Arg Ala Arg Lys
            260                 265                 270

Val Val Ile Thr Ala Thr Gln Met Leu Asp Ser Met Ile Lys Asn Pro
        275                 280                 285

Arg Pro Thr Arg Ala Glu Ala Gly Asp Val Ala Asn Ala Ile Leu Asp
    290                 295                 300

Gly Thr Asp Ala Val Met Leu Ser Gly Glu Ser Ala Lys Gly Lys Tyr
305                 310                 315                 320

Pro Leu Glu Ala Val Ser Ile Met Ala Thr Ile Cys Glu Arg Thr Asp
                325                 330                 335

Arg Val Met Asn Ser Arg Leu Glu Phe Asn Asn Asp Asn Arg Lys Leu
```

-continued

```
            340                 345                 350

Arg Ile Thr Glu Ala Val Cys Arg Gly Ala Val Glu Thr Ala Glu Lys
        355                 360                 365

Leu Asp Ala Pro Leu Ile Val Val Ala Thr Gln Gly Gly Lys Ser Ala
    370                 375                 380

Arg Ala Val Arg Lys Tyr Phe Pro Asp Ala Thr Ile Leu Ala Leu Thr
385                 390                 395                 400

Thr Asn Glu Lys Thr Ala His Gln Leu Val Leu Ser Lys Gly Val Val
                405                 410                 415

Pro Gln Leu Val Lys Glu Ile Thr Ser Thr Asp Asp Phe Tyr Arg Leu
            420                 425                 430

Gly Lys Glu Leu Ala Leu Gln Ser Gly Leu Ala His Lys Gly Asp Val
        435                 440                 445

Val Val Met Val Ser Gly Ala Leu Val Pro Ser Gly Thr Thr Asn Thr
    450                 455                 460

Ala Ser Val His Val Leu
465                 470


<210> SEQ ID NO 28
<211> LENGTH: 480
<212> TYPE: PRT
<213> ORGANISM: Escherichia coli str. K-12 substr. MG1655

<400> SEQUENCE: 28

Met Ser Arg Arg Leu Arg Arg Thr Lys Ile Val Thr Thr Leu Gly Pro
1               5                   10                  15

Ala Thr Asp Arg Asp Asn Asn Leu Glu Lys Val Ile Ala Ala Gly Ala
            20                  25                  30

Asn Val Val Arg Met Asn Phe Ser His Gly Ser Pro Glu Asp His Lys
        35                  40                  45

Met Arg Ala Asp Lys Val Arg Glu Ile Ala Ala Lys Leu Gly Arg His
    50                  55                  60

Val Ala Ile Leu Gly Asp Leu Gln Gly Pro Lys Ile Arg Val Ser Thr
65                  70                  75                  80

Phe Lys Glu Gly Lys Val Phe Leu Asn Ile Gly Asp Lys Phe Leu Leu
                85                  90                  95

Asp Ala Asn Leu Gly Lys Gly Glu Gly Asp Lys Glu Lys Val Gly Ile
            100                 105                 110

Asp Tyr Lys Gly Leu Pro Ala Asp Val Val Pro Gly Asp Ile Leu Leu
        115                 120                 125

Leu Asp Asp Gly Arg Val Gln Leu Lys Val Leu Glu Val Gln Gly Met
    130                 135                 140

Lys Val Phe Thr Glu Val Thr Val Gly Gly Pro Leu Ser Asn Asn Lys
145                 150                 155                 160

Gly Ile Asn Lys Leu Gly Gly Gly Leu Ser Ala Glu Ala Leu Thr Glu
                165                 170                 175

Lys Asp Lys Ala Asp Ile Lys Thr Ala Ala Leu Ile Gly Val Asp Tyr
            180                 185                 190

Leu Ala Val Ser Phe Pro Arg Cys Gly Glu Asp Leu Asn Tyr Ala Arg
        195                 200                 205

Arg Leu Ala Arg Asp Ala Gly Cys Asp Ala Lys Ile Val Ala Lys Val
    210                 215                 220

Glu Arg Ala Glu Ala Val Cys Ser Gln Asp Ala Met Asp Asp Ile Ile
225                 230                 235                 240
```

-continued

```
Leu Ala Ser Asp Val Val Met Val Ala Arg Gly Asp Leu Gly Val Glu
                245                 250                 255

Ile Gly Asp Pro Glu Leu Val Gly Ile Gln Lys Ala Leu Ile Arg Arg
            260                 265                 270

Ala Arg Gln Leu Asn Arg Ala Val Ile Thr Ala Thr Gln Met Met Glu
        275                 280                 285

Ser Met Ile Thr Asn Pro Met Pro Thr Arg Ala Glu Val Met Asp Val
    290                 295                 300

Ala Asn Ala Val Leu Asp Gly Thr Asp Ala Val Met Leu Ser Ala Glu
305                 310                 315                 320

Thr Ala Ala Gly Gln Tyr Pro Ser Glu Thr Val Ala Ala Met Ala Arg
                325                 330                 335

Val Cys Leu Gly Ala Glu Lys Ile Pro Ser Ile Asn Val Ser Lys His
            340                 345                 350

Arg Leu Asp Val Gln Phe Asp Asn Val Glu Glu Ala Ile Ala Met Ser
        355                 360                 365

Ala Met Tyr Ala Ala Asn His Leu Lys Gly Val Thr Ala Ile Ile Thr
    370                 375                 380

Met Thr Glu Ser Gly Arg Thr Ala Leu Met Thr Ser Arg Ile Ser Ser
385                 390                 395                 400

Gly Leu Pro Ile Phe Ala Met Ser Arg His Glu Arg Thr Leu Asn Leu
                405                 410                 415

Thr Ala Leu Tyr Arg Gly Val Thr Pro Val His Phe Asp Ser Ala Asn
            420                 425                 430

Asp Gly Val Ala Ala Ala Ser Glu Ala Val Asn Leu Leu Arg Asp Lys
        435                 440                 445

Gly Tyr Leu Met Ser Gly Asp Leu Val Ile Val Thr Gln Gly Asp Val
    450                 455                 460

Met Ser Thr Val Gly Ser Thr Asn Thr Thr Arg Ile Leu Thr Val Glu
465                 470                 475                 480


<210> SEQ ID NO 29
<211> LENGTH: 1413
<212> TYPE: DNA
<213> ORGANISM: Serratia grimesii NBRC13537
<220> FEATURE:
<221> NAME/KEY: CDS
<222> LOCATION: (1)..(1413)

<400> SEQUENCE: 29

atg aaa aag acc aaa att gtt tgt acc atc ggt cca aaa acc gaa tcg       48
Met Lys Lys Thr Lys Ile Val Cys Thr Ile Gly Pro Lys Thr Glu Ser
1               5                   10                  15

gaa gaa atg ctg acc aac ctg ctg aat gcc ggc atg aac gta atg cgc       96
Glu Glu Met Leu Thr Asn Leu Leu Asn Ala Gly Met Asn Val Met Arg
            20                  25                  30

ctg aac ttc tca cat ggt gat tat gaa gag cac ggc aac cgc atc aag      144
Leu Asn Phe Ser His Gly Asp Tyr Glu Glu His Gly Asn Arg Ile Lys
        35                  40                  45

aac atg cgc gca gtg atg gcg aaa acc ggt cag aac gcg ggt atc ctg      192
Asn Met Arg Ala Val Met Ala Lys Thr Gly Gln Asn Ala Gly Ile Leu
    50                  55                  60

ttg gat acc aaa ggc ccg gaa atc cgc acc atg aaa ctg gaa ggc ggc      240
Leu Asp Thr Lys Gly Pro Glu Ile Arg Thr Met Lys Leu Glu Gly Gly
65                  70                  75                  80

aaa gac gct gcc ctg gtt gcc ggt cag act ttc act ttc acc acc gat      288
Lys Asp Ala Ala Leu Val Ala Gly Gln Thr Phe Thr Phe Thr Thr Asp
                85                  90                  95
```

-continued

```
cag agc gtt atc ggc aac aac gaa cgt gtt gca gtc act tat gca ggc      336
Gln Ser Val Ile Gly Asn Asn Glu Arg Val Ala Val Thr Tyr Ala Gly
            100                 105                 110

ttt agt gct gac ctg aaa att ggt aac acc gtg ctg gta gac gat ggt      384
Phe Ser Ala Asp Leu Lys Ile Gly Asn Thr Val Leu Val Asp Asp Gly
        115                 120                 125

ctg atc ggc atg gaa gtc acc aac gtg acc gaa aac gaa gtg gtt tgt      432
Leu Ile Gly Met Glu Val Thr Asn Val Thr Glu Asn Glu Val Val Cys
    130                 135                 140

aag gtg ctg aac agc ggt gac ctg ggc gag aac aaa ggc gtt aac ctg      480
Lys Val Leu Asn Ser Gly Asp Leu Gly Glu Asn Lys Gly Val Asn Leu
145                 150                 155                 160

cca ggc gtt tct att cag ttg cct gca ctg gca gaa aaa gac aaa cgc      528
Pro Gly Val Ser Ile Gln Leu Pro Ala Leu Ala Glu Lys Asp Lys Arg
                165                 170                 175

gat ctg att ttc ggc tgc gaa caa ggt gtg gac ttc gtt gct gcg tcc      576
Asp Leu Ile Phe Gly Cys Glu Gln Gly Val Asp Phe Val Ala Ala Ser
            180                 185                 190

ttt atc cgt aaa cgt tca gac gtg ctg gaa atc cgt gaa cac ctg aaa      624
Phe Ile Arg Lys Arg Ser Asp Val Leu Glu Ile Arg Glu His Leu Lys
        195                 200                 205

gcc cac ggt ggt gag caa atc cag atc atc tct aaa atc gaa aac cag      672
Ala His Gly Gly Glu Gln Ile Gln Ile Ile Ser Lys Ile Glu Asn Gln
    210                 215                 220

gaa ggc ctg aac aac ttc gac gag atc ctc gaa gcg tct gac ggc atc      720
Glu Gly Leu Asn Asn Phe Asp Glu Ile Leu Glu Ala Ser Asp Gly Ile
225                 230                 235                 240

atg gtt gct cgt ggt gat ctg ggt gtg gaa att ccg gta gaa gaa gtg      768
Met Val Ala Arg Gly Asp Leu Gly Val Glu Ile Pro Val Glu Glu Val
                245                 250                 255

atc ttc gcg cag aag atg atg atc gaa aaa tgt aat cgt gca cgc aaa      816
Ile Phe Ala Gln Lys Met Met Ile Glu Lys Cys Asn Arg Ala Arg Lys
            260                 265                 270

gtg gtt atc acc gca acg cag atg ctc gat tca atg atc aaa aac ccg      864
Val Val Ile Thr Ala Thr Gln Met Leu Asp Ser Met Ile Lys Asn Pro
        275                 280                 285

cgc cct acc cgc gca gaa gct ggc gac gtt gct aac gcc att ttg gat      912
Arg Pro Thr Arg Ala Glu Ala Gly Asp Val Ala Asn Ala Ile Leu Asp
    290                 295                 300

ggt acc gac gct gtc atg ctg tca ggt gag agc gcc aag ggt aag tac      960
Gly Thr Asp Ala Val Met Leu Ser Gly Glu Ser Ala Lys Gly Lys Tyr
305                 310                 315                 320

cca ctg gaa gcc gtt acc atc atg gcg acc atc tgt gag cgc aca gat     1008
Pro Leu Glu Ala Val Thr Ile Met Ala Thr Ile Cys Glu Arg Thr Asp
                325                 330                 335

cgc gta atg cca agc cgt atc gac agc ctg aat gac aac cgc aaa ctg     1056
Arg Val Met Pro Ser Arg Ile Asp Ser Leu Asn Asp Asn Arg Lys Leu
            340                 345                 350

cgc atc act gaa gca gta tgc cgt ggt gct gtt gaa acc gca gaa aaa     1104
Arg Ile Thr Glu Ala Val Cys Arg Gly Ala Val Glu Thr Ala Glu Lys
        355                 360                 365

ctg gat gcg cca ctg atc gtt gtt gcc acc agc ggc ggt aaa tca gcc     1152
Leu Asp Ala Pro Leu Ile Val Val Ala Thr Ser Gly Gly Lys Ser Ala
    370                 375                 380

aaa tcc gtg cgt aaa tac ttc cct aac gca gtg atc ctg gcg ttg acc     1200
Lys Ser Val Arg Lys Tyr Phe Pro Asn Ala Val Ile Leu Ala Leu Thr
385                 390                 395                 400

acc aat gaa gtc acc gct cac cag ctc att ctg agc aaa ggc gtg att     1248
Thr Asn Glu Val Thr Ala His Gln Leu Ile Leu Ser Lys Gly Val Ile
```

-continued

```
                405                 410                 415

cca cag atg gtt aag gaa atc gcc tct acc gac gat ttc tac cgc att      1296
Pro Gln Met Val Lys Glu Ile Ala Ser Thr Asp Asp Phe Tyr Arg Ile
            420                 425                 430

ggt aaa gaa gcg gcg ttg gcc agc ggt ctt gca caa aaa ggc gac gtt      1344
Gly Lys Glu Ala Ala Leu Ala Ser Gly Leu Ala Gln Lys Gly Asp Val
        435                 440                 445

gtg gtg atg gtt tct ggt gcc ctg gta cca agt ggc acc acc aat act      1392
Val Val Met Val Ser Gly Ala Leu Val Pro Ser Gly Thr Thr Asn Thr
    450                 455                 460

gcc tcg gtt cac gtg ctc taa                                          1413
Ala Ser Val His Val Leu
465                 470


<210> SEQ ID NO 30
<211> LENGTH: 470
<212> TYPE: PRT
<213> ORGANISM: Serratia grimesii NBRC13537

<400> SEQUENCE: 30

Met Lys Lys Thr Lys Ile Val Cys Thr Ile Gly Pro Lys Thr Glu Ser
1               5                   10                  15

Glu Glu Met Leu Thr Asn Leu Leu Asn Ala Gly Met Asn Val Met Arg
            20                  25                  30

Leu Asn Phe Ser His Gly Asp Tyr Glu Glu His Gly Asn Arg Ile Lys
        35                  40                  45

Asn Met Arg Ala Val Met Ala Lys Thr Gly Gln Asn Ala Gly Ile Leu
    50                  55                  60

Leu Asp Thr Lys Gly Pro Glu Ile Arg Thr Met Lys Leu Glu Gly Gly
65                  70                  75                  80

Lys Asp Ala Ala Leu Val Ala Gly Gln Thr Phe Thr Phe Thr Thr Asp
                85                  90                  95

Gln Ser Val Ile Gly Asn Asn Glu Arg Val Ala Val Thr Tyr Ala Gly
            100                 105                 110

Phe Ser Ala Asp Leu Lys Ile Gly Asn Thr Val Leu Val Asp Asp Gly
        115                 120                 125

Leu Ile Gly Met Glu Val Thr Asn Val Thr Glu Asn Glu Val Val Cys
    130                 135                 140

Lys Val Leu Asn Ser Gly Asp Leu Gly Glu Asn Lys Gly Val Asn Leu
145                 150                 155                 160

Pro Gly Val Ser Ile Gln Leu Pro Ala Leu Ala Glu Lys Asp Lys Arg
                165                 170                 175

Asp Leu Ile Phe Gly Cys Glu Gln Gly Val Asp Phe Val Ala Ala Ser
            180                 185                 190

Phe Ile Arg Lys Arg Ser Asp Val Leu Glu Ile Arg Glu His Leu Lys
        195                 200                 205

Ala His Gly Gly Glu Gln Ile Gln Ile Ile Ser Lys Ile Glu Asn Gln
    210                 215                 220

Glu Gly Leu Asn Asn Phe Asp Glu Ile Leu Glu Ala Ser Asp Gly Ile
225                 230                 235                 240

Met Val Ala Arg Gly Asp Leu Gly Val Glu Ile Pro Val Glu Glu Val
                245                 250                 255

Ile Phe Ala Gln Lys Met Met Ile Glu Lys Cys Asn Arg Ala Arg Lys
            260                 265                 270

Val Val Ile Thr Ala Thr Gln Met Leu Asp Ser Met Ile Lys Asn Pro
        275                 280                 285
```

```
Arg Pro Thr Arg Ala Glu Ala Gly Asp Val Ala Asn Ala Ile Leu Asp
    290                 295                 300

Gly Thr Asp Ala Val Met Leu Ser Gly Glu Ser Ala Lys Gly Lys Tyr
305                 310                 315                 320

Pro Leu Glu Ala Val Thr Ile Met Ala Thr Ile Cys Glu Arg Thr Asp
                325                 330                 335

Arg Val Met Pro Ser Arg Ile Asp Ser Leu Asn Asp Asn Arg Lys Leu
            340                 345                 350

Arg Ile Thr Glu Ala Val Cys Arg Gly Ala Val Glu Thr Ala Glu Lys
        355                 360                 365

Leu Asp Ala Pro Leu Ile Val Val Ala Thr Ser Gly Gly Lys Ser Ala
    370                 375                 380

Lys Ser Val Arg Lys Tyr Phe Pro Asn Ala Val Ile Leu Ala Leu Thr
385                 390                 395                 400

Thr Asn Glu Val Thr Ala His Gln Leu Ile Leu Ser Lys Gly Val Ile
                405                 410                 415

Pro Gln Met Val Lys Glu Ile Ala Ser Thr Asp Asp Phe Tyr Arg Ile
            420                 425                 430

Gly Lys Glu Ala Ala Leu Ala Ser Gly Leu Ala Gln Lys Gly Asp Val
        435                 440                 445

Val Val Met Val Ser Gly Ala Leu Val Pro Ser Gly Thr Thr Asn Thr
    450                 455                 460

Ala Ser Val His Val Leu
465                 470


<210> SEQ ID NO 31
<211> LENGTH: 480
<212> TYPE: PRT
<213> ORGANISM: Serratia grimesii NBRC13537

<400> SEQUENCE: 31

Met Ser Arg Arg Leu Arg Arg Thr Lys Ile Val Thr Thr Leu Gly Pro
1               5                   10                  15

Ala Thr Asp Arg Asp Asn Asn Leu Glu Lys Ile Ile Ala Ala Gly Ala
            20                  25                  30

Asn Val Val Arg Leu Asn Phe Ser His Gly Ser Ala Glu Asp His Gln
        35                  40                  45

Ala Arg Ala Asp Lys Val Arg Glu Ile Ala Ala Lys Leu Gly Arg His
    50                  55                  60

Val Ala Ile Leu Gly Asp Leu Gln Gly Pro Lys Ile Arg Val Ser Thr
65                  70                  75                  80

Phe Lys Glu Gly Lys Ile Phe Leu Asn Ile Gly Asp Lys Phe Leu Leu
                85                  90                  95

Asp Ala Asn Met Ser Lys Gly Glu Gly Asp Lys Glu Lys Val Gly Ile
            100                 105                 110

Asp Tyr Lys Gly Leu Pro Ala Asp Val Val Pro Gly Asp Val Leu Leu
        115                 120                 125

Leu Asp Asp Gly Arg Val Gln Leu Lys Val Leu Glu Val Gln Gly Met
    130                 135                 140

Lys Val Phe Thr Glu Val Thr Val Gly Gly Pro Leu Ser Asn Asn Lys
145                 150                 155                 160

Gly Ile Asn Lys Leu Gly Gly Gly Leu Ser Ala Glu Ala Leu Thr Glu
                165                 170                 175

Lys Asp Lys Ala Asp Ile Val Thr Ala Ala Lys Ile Gly Val Asp Tyr
```

```
            180                 185                 190

Leu Ala Val Ser Phe Pro Arg Thr Gly Glu Asp Leu Asn Tyr Ala Arg
        195                 200                 205

Arg Leu Ala Arg Asp Ala Gly Cys Asn Ala Lys Ile Val Ser Lys Val
    210                 215                 220

Glu Arg Ala Glu Ala Val Cys Ser Asp Glu Ala Met Asp Asp Ile Ile
225                 230                 235                 240

Leu Ala Ser Asp Val Val Met Val Ala Arg Gly Asp Leu Gly Val Glu
                245                 250                 255

Ile Gly Asp Pro Glu Leu Val Gly Ile Gln Lys Lys Leu Ile Arg Arg
            260                 265                 270

Ala Arg Thr Leu Asn Arg Ala Val Ile Thr Ala Thr Gln Met Met Glu
        275                 280                 285

Ser Met Ile Thr Asn Pro Met Pro Thr Arg Ala Glu Val Met Asp Val
    290                 295                 300

Ala Asn Ala Val Leu Asp Gly Thr Asp Ala Val Met Leu Ser Ala Glu
305                 310                 315                 320

Thr Ala Ala Gly Gln Tyr Pro Ala Glu Thr Val Ala Ala Met Ala Arg
                325                 330                 335

Val Cys Leu Gly Ala Glu Lys Ile Pro Ser Ile Asn Val Ser Lys His
            340                 345                 350

Arg Leu Asp Val Gln Phe Asp Asn Ile Glu Glu Ala Ile Ala Met Ser
        355                 360                 365

Ser Met Tyr Ala Ala Asn His Leu Lys Gly Val Thr Ala Leu Ile Ala
    370                 375                 380

Met Thr Glu Ser Gly Arg Thr Ala Leu Met Met Ser Arg Ile Ser Ser
385                 390                 395                 400

Gly Leu Pro Ile Phe Ala Met Ser Arg His Glu His Thr Leu Asn Leu
                405                 410                 415

Thr Ala Leu Tyr Arg Gly Val Thr Pro Val Tyr Phe Asp Ser His Glu
            420                 425                 430

Asp Gly Val Ile Ala Ala Asn Asp Ala Val Asn Arg Leu Arg Asp Lys
        435                 440                 445

Gly Phe Leu Val Ser Gly Asp Leu Val Ile Val Thr Gln Gly Asp Val
    450                 455                 460

Met Glu Thr Val Gly Thr Thr Asn Thr Ser Arg Ile Leu Arg Val Glu
465                 470                 475                 480


<210> SEQ ID NO 32
<211> LENGTH: 540
<212> TYPE: PRT
<213> ORGANISM: Escherichia coli str. K-12 substr. MG1655

<400> SEQUENCE: 32

Met Arg Val Asn Asn Gly Leu Thr Pro Gln Glu Leu Glu Ala Tyr Gly
1               5                   10                  15

Ile Ser Asp Val His Asp Ile Val Tyr Asn Pro Ser Tyr Asp Leu Leu
            20                  25                  30

Tyr Gln Glu Glu Leu Asp Pro Ser Leu Thr Gly Tyr Glu Arg Gly Val
        35                  40                  45

Leu Thr Asn Leu Gly Ala Val Ala Val Asp Thr Gly Ile Phe Thr Gly
    50                  55                  60

Arg Ser Pro Lys Asp Lys Tyr Ile Val Arg Asp Asp Thr Thr Arg Asp
65                  70                  75                  80
```

-continued

```
Thr Phe Trp Trp Ala Asp Lys Gly Lys Gly Lys Asn Asp Asn Lys Pro
                85                  90                  95

Leu Ser Pro Glu Thr Trp Gln His Leu Lys Gly Leu Val Thr Arg Gln
            100                 105                 110

Leu Ser Gly Lys Arg Leu Phe Val Val Asp Ala Phe Cys Gly Ala Asn
        115                 120                 125

Pro Asp Thr Arg Leu Ser Val Arg Phe Ile Thr Glu Val Ala Trp Gln
    130                 135                 140

Ala His Phe Val Lys Asn Met Phe Ile Arg Pro Ser Asp Glu Glu Leu
145                 150                 155                 160

Ala Gly Phe Lys Pro Asp Phe Ile Val Met Asn Gly Ala Lys Cys Thr
                165                 170                 175

Asn Pro Gln Trp Lys Glu Gln Gly Leu Asn Ser Glu Asn Phe Val Ala
            180                 185                 190

Phe Asn Leu Thr Glu Arg Met Gln Leu Ile Gly Gly Thr Trp Tyr Gly
        195                 200                 205

Gly Glu Met Lys Lys Gly Met Phe Ser Met Met Asn Tyr Leu Leu Pro
    210                 215                 220

Leu Lys Gly Ile Ala Ser Met His Cys Ser Ala Asn Val Gly Glu Lys
225                 230                 235                 240

Gly Asp Val Ala Val Phe Phe Gly Leu Ser Gly Thr Gly Lys Thr Thr
                245                 250                 255

Leu Ser Thr Asp Pro Lys Arg Arg Leu Ile Gly Asp Asp Glu His Gly
            260                 265                 270

Trp Asp Asp Asp Gly Val Phe Asn Phe Glu Gly Gly Cys Tyr Ala Lys
        275                 280                 285

Thr Ile Lys Leu Ser Lys Glu Ala Glu Pro Glu Ile Tyr Asn Ala Ile
    290                 295                 300

Arg Arg Asp Ala Leu Leu Glu Asn Val Thr Val Arg Glu Asp Gly Thr
305                 310                 315                 320

Ile Asp Phe Asp Asp Gly Ser Lys Thr Glu Asn Thr Arg Val Ser Tyr
                325                 330                 335

Pro Ile Tyr His Ile Asp Asn Ile Val Lys Pro Val Ser Lys Ala Gly
            340                 345                 350

His Ala Thr Lys Val Ile Phe Leu Thr Ala Asp Ala Phe Gly Val Leu
        355                 360                 365

Pro Pro Val Ser Arg Leu Thr Ala Asp Gln Thr Gln Tyr His Phe Leu
    370                 375                 380

Ser Gly Phe Thr Ala Lys Leu Ala Gly Thr Glu Arg Gly Ile Thr Glu
385                 390                 395                 400

Pro Thr Pro Thr Phe Ser Ala Cys Phe Gly Ala Ala Phe Leu Ser Leu
                405                 410                 415

His Pro Thr Gln Tyr Ala Glu Val Leu Val Lys Arg Met Gln Ala Ala
            420                 425                 430

Gly Ala Gln Ala Tyr Leu Val Asn Thr Gly Trp Asn Gly Thr Gly Lys
        435                 440                 445

Arg Ile Ser Ile Lys Asp Thr Arg Ala Ile Ile Asp Ala Ile Leu Asn
    450                 455                 460

Gly Ser Leu Asp Asn Ala Glu Thr Phe Thr Leu Pro Met Phe Asn Leu
465                 470                 475                 480

Ala Ile Pro Thr Glu Leu Pro Gly Val Asp Thr Lys Ile Leu Asp Pro
                485                 490                 495

Arg Asn Thr Tyr Ala Ser Pro Glu Gln Trp Gln Glu Lys Ala Glu Thr
```

-continued

```
            500                 505                 510

Leu Ala Lys Leu Phe Ile Asp Asn Phe Asp Lys Tyr Thr Asp Thr Pro
        515                 520                 525

Ala Gly Ala Ala Leu Val Ala Ala Gly Pro Lys Leu
    530                 535                 540


<210> SEQ ID NO 33
<211> LENGTH: 539
<212> TYPE: PRT
<213> ORGANISM: Serratia grimesii NBRC13537

<400> SEQUENCE: 33

Met Arg Val Lys Gly Ile Thr Pro Gln Asp Leu Ala Ala Tyr Gly Ile
1               5                   10                  15

His Asn Val Gly Glu Ile Val His Asn Pro Ser Tyr Asp Leu Leu Phe
            20                  25                  30

Lys Glu Glu Thr Asp Pro Ser Leu Glu Gly Phe Glu Arg Gly Val Val
        35                  40                  45

Thr Lys Leu Gly Ala Val Ser Val Asp Thr Gly Ile Phe Thr Gly Arg
    50                  55                  60

Ser Pro Lys Asp Lys Tyr Ile Val Arg Asp Asp Ile Thr Arg Asp Thr
65                  70                  75                  80

Val Trp Trp Ala Asp Gln Gly Lys Gly Lys Asn Asp Asn Lys Pro Leu
                85                  90                  95

Ser Pro Glu Ile Trp Ala Asp Leu Lys Gln Leu Val Thr Thr Gln Leu
            100                 105                 110

Ser Gly Lys Arg Leu Phe Val Met Asp Thr Phe Cys Gly Ala Asn Ala
        115                 120                 125

Asp Ser Arg Leu Lys Val Arg Phe Ile Thr Glu Val Ala Trp Gln Ala
    130                 135                 140

His Phe Val Lys Asn Met Phe Ile Arg Pro Thr Asp Glu Glu Leu Gln
145                 150                 155                 160

Asp Phe Glu Pro Asp Phe Val Val Met Asn Gly Ala Lys Cys Thr Asn
                165                 170                 175

Pro Asn Trp Gln Gln Gln Gly Leu Asn Ser Glu Asn Phe Val Ala Phe
            180                 185                 190

Asn Leu Thr Glu Arg Met Gln Leu Ile Gly Gly Thr Trp Tyr Gly Gly
        195                 200                 205

Glu Met Lys Lys Gly Met Phe Ser Ile Met Asn Tyr Leu Leu Pro Leu
    210                 215                 220

Lys Gly Ile Ala Ser Met His Cys Ser Ala Asn Val Gly Glu Lys Gly
225                 230                 235                 240

Asp Val Ala Val Phe Phe Gly Leu Ser Gly Thr Gly Lys Thr Thr Leu
                245                 250                 255

Ser Thr Asp Pro Lys Arg Gln Leu Ile Gly Asp Asp Glu His Gly Trp
            260                 265                 270

Asp Asp Asp Gly Val Phe Asn Phe Glu Gly Gly Cys Tyr Ala Lys Thr
        275                 280                 285

Ile Lys Leu Ser Glu Glu Ala Glu Pro Asp Ile Tyr His Ala Ile Lys
    290                 295                 300

Arg Asp Ala Leu Leu Glu Asn Val Val Val Leu Ala Asp Gly Thr Ile
305                 310                 315                 320

Asp Phe Asn Asp Gly Ser Lys Thr Glu Asn Thr Arg Val Ser Tyr Pro
                325                 330                 335
```

-continued

```
Ile Tyr His Ile Gln Asn Ile Val Lys Pro Val Ser Lys Ala Gly His
            340                 345                 350

Ala Thr Lys Val Ile Phe Leu Thr Ala Asp Ala Phe Gly Val Leu Pro
        355                 360                 365

Pro Val Ser Arg Leu Thr Ala Asn Gln Thr Gln Tyr His Phe Leu Ser
    370                 375                 380

Gly Phe Thr Ala Lys Leu Ala Gly Thr Glu Arg Gly Val Thr Glu Pro
385                 390                 395                 400

Thr Pro Thr Phe Ser Ala Cys Phe Gly Ala Ala Phe Leu Ser Leu His
                405                 410                 415

Pro Thr Gln Tyr Ala Glu Val Leu Val Lys Arg Met Gln Ala Ala Gly
            420                 425                 430

Ala Gln Ala Tyr Leu Val Asn Thr Gly Trp Asn Gly Thr Gly Lys Arg
        435                 440                 445

Ile Ser Ile Lys Asp Thr Arg Gly Ile Ile Asp Ala Ile Leu Ser Gly
    450                 455                 460

Glu Ile Asp Lys Ala Glu Thr Ile Thr Leu Pro Ile Phe Asp Leu Ala
465                 470                 475                 480

Met Pro Thr Ser Leu Pro Gly Val Asn Pro Asp Ile Leu Asp Pro Arg
                485                 490                 495

Ala Thr Tyr Ala Ser Leu Glu Gln Trp Gln Glu Lys Ala Gln Asp Leu
            500                 505                 510

Ala Glu Arg Phe Val Thr Asn Phe Asp Lys Tyr Thr Asp Thr Pro Ala
        515                 520                 525

Gly Ala Ala Leu Val Ser Ala Gly Pro Lys Leu
    530                 535


<210> SEQ ID NO 34
<211> LENGTH: 539
<212> TYPE: PRT
<213> ORGANISM: Serratia grimesii NBRC13537

<400> SEQUENCE: 34

Met Ser Ser Ile Ala Ile Thr Pro Gln Thr Leu Ala Arg Tyr Gly Ile
1               5                   10                  15

His Gln Ala Thr Glu Ile Val His Asn Pro Ser Tyr Glu Gln Leu Phe
            20                  25                  30

Thr Glu Glu Thr Arg Ala Asp Leu Pro Ala Leu Glu Arg Gly Thr Leu
        35                  40                  45

Thr Thr Leu Gly Ala Val Asn Val Asp Thr Gly Glu Phe Thr Gly Arg
    50                  55                  60

Ser Pro Lys Asp Lys Tyr Ile Val Arg Asp Asp Thr Thr Arg Asp Thr
65                  70                  75                  80

Val Trp Trp Ser Asp Asn Gly Thr Gly Lys Asn Asp Asn Gln Pro Leu
                85                  90                  95

Ser Pro Glu Ile Trp Gln His Leu Lys Thr Leu Val Gly Asn Gln Leu
            100                 105                 110

Ser Gly Lys Arg Leu Phe Val Val Asp Ala Phe Cys Gly Ala Asn Ala
        115                 120                 125

Asp Thr Arg Leu Lys Val Arg Phe Ile Thr Glu Val Ala Trp Gln Ala
    130                 135                 140

His Phe Val Lys Asn Met Phe Ile Arg Pro Thr Asp Glu Glu Leu Gln
145                 150                 155                 160

Asn Phe Glu Pro Asp Phe Val Val Met Asn Gly Ala Lys Cys Thr Asn
                165                 170                 175
```

-continued

```
Pro Asp Trp Gln Gln Gln Gly Met His Ser Glu Asn Phe Val Thr Phe
            180                 185                 190

Asn Leu Thr Glu Arg Met Gln Leu Ile Gly Gly Thr Trp Tyr Gly Gly
        195                 200                 205

Glu Met Lys Lys Gly Leu Phe Ser Ile Met Asn Tyr Leu Leu Pro Leu
    210                 215                 220

Gln Gly Ile Ala Ser Met His Cys Ser Ala Asn Val Gly Glu Gln Gly
225                 230                 235                 240

Asp Val Ala Val Phe Phe Gly Leu Ser Gly Thr Gly Lys Thr Thr Leu
                245                 250                 255

Ser Thr Asp Pro Lys Arg Gln Leu Ile Gly Asp Asp Glu His Gly Trp
            260                 265                 270

Asp Asp Asp Gly Val Phe Asn Phe Glu Gly Gly Cys Tyr Ala Lys Thr
        275                 280                 285

Ile Lys Leu Ser Gln Gln Ala Glu Pro Glu Ile Tyr Gln Ala Ile Arg
    290                 295                 300

Arg Asn Ala Leu Leu Glu Asn Val Gln Val Leu Ala Asp Gly Ser Ile
305                 310                 315                 320

Asp Phe Asp Asp Ala Ser Lys Thr Glu Asn Thr Arg Val Ser Tyr Pro
                325                 330                 335

Ile Asp His Ile Glu Asn Ile Val Lys Pro Val Ser Lys Ala Gly His
            340                 345                 350

Ala Lys Lys Ile Ile Phe Leu Thr Ala Asp Ala Phe Gly Val Leu Pro
        355                 360                 365

Pro Val Ser Arg Leu Thr Pro Glu Gln Thr Gln Tyr His Phe Leu Ser
    370                 375                 380

Gly Phe Thr Ala Lys Leu Ala Gly Thr Glu Arg Gly Ile Thr Thr Pro
385                 390                 395                 400

Thr Pro Thr Phe Ser Ala Cys Phe Gly Ala Ala Phe Leu Thr Leu His
                405                 410                 415

Pro Thr Gln Tyr Ala Glu Val Leu Val Lys Arg Met Glu Ala Ala Gly
            420                 425                 430

Ala Gln Ala Tyr Leu Val Asn Thr Gly Trp Asn Gly Ser Gly Lys Arg
        435                 440                 445

Ile Ser Ile Lys Asp Thr Arg Gly Ile Ile Asp Ala Ile Leu Asn Gly
    450                 455                 460

Glu Ile Glu His Ala Glu Thr Phe Thr Leu Pro Ile Phe Gly Leu Ala
465                 470                 475                 480

Val Pro Thr Ala Leu Pro Gly Val Asp Pro Ser Ile Leu Asp Pro Arg
                485                 490                 495

Lys Thr Tyr Ala Asp Glu Ser Leu Trp Gln Glu Lys Ala Gln Asp Leu
            500                 505                 510

Ala Gln Arg Phe Ile Asp Asn Phe Ala Lys Tyr Thr Val Thr Pro Ala
        515                 520                 525

Gly Glu Lys Leu Val Gly Ala Gly Pro Lys Leu
    530                 535
```

<210> SEQ ID NO 35
<211> LENGTH: 200
<212> TYPE: DNA
<213> ORGANISM: Escherichia coli str. K-12 substr. MG1655

<400> SEQUENCE: 35

```
cgtaattgcc ctttaaaatt cggggcgccg accccatgtg gtctcaagcc caaaggaaga     60
```

gtgaggcgag tcagtcgcgt aatgcttagg cacaggattg atttgtcgca atgattgaca 120
cgattccgct tgacgctgcg taaggttttt gtaattttac aggcaacctt ttattcacta 180
acaaatagct ggtggaatat 200

<210> SEQ ID NO 36
<211> LENGTH: 30
<212> TYPE: DNA
<213> ORGANISM: Artificial Sequence
<220> FEATURE:
<223> OTHER INFORMATION: primer

<400> SEQUENCE: 36
taccgtcgac ctcgacgtaa ttgcccttta 30

<210> SEQ ID NO 37
<211> LENGTH: 41
<212> TYPE: DNA
<213> ORGANISM: Artificial Sequence
<220> FEATURE:
<223> OTHER INFORMATION: primer

<400> SEQUENCE: 37 ggcccccct cgagtcatta agtactatat tccaccagct a 41

<210> SEQ ID NO 38
<211> LENGTH: 774
<212> TYPE: DNA
<213> ORGANISM: Pseudomonas putida KT2440

<400> SEQUENCE: 38
atgccgcgat atatcgatgt gcaggcgccc gaacatggcg ttcagctcat taccctgcaa 60
cggcccgagg ccttgaatgc cctgtgcacc gagctactgg cagaactggc cgctgcgctg 120
caggctgccg ggaacgacga gcatgtccgt gccacagtga ttaccggcag cgccaaggca 180
ttcgccgcag gcgccgacat ccgcgagatg gccgatcgcg acctggtcgg catcctcaat 240
gacccgcgcg tagcgcattg gcaaagcatc gccgcattcg ccaaaccgct gattgctgca 300
gtcaacggct atgccctggg tggcggttgc gaactggcaa tgtgcgccga catcgtcatc 360
gccagtaccg acgcccgttt cggccagccg gaaatcaacc ttggcatcat ccccggtgct 420
ggcggcaccc agcgcctgtt acgtgccgtc ggtaagccgt tggccatgca gatggtgctg 480
acgggggaag ccatcactgc cctccgcgcc cagcaggccg gcctggtcag cgaaatcacc 540
cagcccgaac tcaccgtaga acgcgccatg caggttgccc gcagcatcgc cgccaaagcg 600
ccgctggctg tgcgcctggc caaggaggcg ttactgaagg ccggtgatac cgacctggcc 660
agcggcctgc gcttcgagcg ccatgccttc accctgctgg cgggcaccgc cgaccgcgat 720
gaaggcatcc gcgccttcca ggaaaagcgc caggcccgct tccaagggcg ctga 774

<210> SEQ ID NO 39
<211> LENGTH: 32
<212> TYPE: DNA
<213> ORGANISM: Artificial Sequence
<220> FEATURE:
<223> OTHER INFORMATION: primer

<400> SEQUENCE: 39
ctggtggaat atatgcacga cgtattcatc tg 32

<210> SEQ ID NO 40

-continued

<211> LENGTH: 41
<212> TYPE: DNA
<213> ORGANISM: Artificial Sequence
<220> FEATURE:
<223> OTHER INFORMATION: primer

<400> SEQUENCE: 40
ctcgagtcat taagtgttaa ctcaaacccg ctcgatggcc a 41

<210> SEQ ID NO 41
<211> LENGTH: 696
<212> TYPE: DNA
<213> ORGANISM: Pseudomonas putida KT2440

<400> SEQUENCE: 41
ttgatcaata aaacgtacga gtccatcgcc agcgcggtgg aagggattac cgacggttcg 60
accatcatgg tcggtggctt cggcacggct ggcatgccgt ccgagctgat cgatggcctc 120
attgccaccg gtgcccgcga cctgaccatc atcagcaaca acgccggcaa cggcgagatc 180
ggcctggccg ccctgctcat ggcaggcagc gtgcgcaagg tggtctgctc gttcccgcgc 240
cagtccgact cctacgtgtt cgacgaactg taccgcgccg gcaagatcga gctggaagtg 300
gtcccgcagg gcaacctggc cgagcgtatc cgcgccgcag gctccggcat tggtgcgttc 360
ttctcgccaa ccggctacgg caccctgctg gccgagggca aggaaacccg tgagatcgat 420
ggccgcatgt acgtgctgga aatgccgctg cacgccgact tcgcactgat caaggcgcac 480
aagggtgacc gttggggcaa cctgacctac cgcaaggccg cccgcaactt cggccccgatc 540 atggccatgg ctgccaagac cgccatcgcc caggtcgacc aggtcgtcga actcggtgaa 600
ctggacccgg aacacatcat caccccgggt atcttcgtcc agcgcgtggt cgccgtcacc 660
ggtgctgccg cttcttcgat tgccaaagct gtctga 696

<210> SEQ ID NO 42
<211> LENGTH: 642
<212> TYPE: DNA
<213> ORGANISM: Pseudomonas putida KT2440

<400> SEQUENCE: 42
atgaccatca ccaaaaagct ctcccgcacc gagatggccc aacgcgtggc cgcagacatc 60
caggaaggcg cgtacgtaaa cctgggcatc ggcgcaccga ccctggtggc caactacctg 120
ggcgacaagg aagtgttcct gcacagcgag aacggcctgc tgggcatggg cccaagccct 180
gcgccgggcg aggaagacga tgacctgatc aacgccggca agcagcacgt caccctgctg 240
accggtggtg ccttcttcca ccatgccgat tcgttctcga tgatgcgtgg cggccacctg 300
gacatcgctg tactgggcgc cttccaggtg tcggtcaagg gcgacctggc caactggcac 360
acgggtgccg aaggctcgat cccggccgta ggcggtgcaa tggacctggc caccggcgcc 420
cgccaggtgt tcgtgatgat ggaccacctg accaagaccg gcgaaagcaa gctggtgccc 480
gagtgcacct acccgctgac cggtatcgct tgcgtcagcc gcatctacac cgacctggcc 540
gtactggaag tgacacctga agggctgaaa gtggtcgaaa tctgcgcgga catcgacttt 600
gacgagctgc agaaactcag tggcgtgccg ctgatcaagt ga 642

<210> SEQ ID NO 43
<211> LENGTH: 55
<212> TYPE: DNA
<213> ORGANISM: Artificial Sequence
<220> FEATURE:
<223> OTHER INFORMATION: primer

<400> SEQUENCE: 43
gagcgggttt gagttcaatt gtagctggtg gaatatttga tcaataaaac gtacg 55

<210> SEQ ID NO 44
<211> LENGTH: 34
<212> TYPE: DNA
<213> ORGANISM: Artificial Sequence
<220> FEATURE:
<223> OTHER INFORMATION: primer

<400> SEQUENCE: 44
gagtcattaa gtgtttcact tgatcagcgg cacg 34

<210> SEQ ID NO 45
<211> LENGTH: 35
<212> TYPE: DNA
<213> ORGANISM: Artificial Sequence
<220> FEATURE:
<223> OTHER INFORMATION: primer

<400> SEQUENCE: 45
ctggtggaat atagtactat ggcagaaagt aatgc 35

<210> SEQ ID NO 46
<211> LENGTH: 39
<212> TYPE: DNA
<213> ORGANISM: Artificial Sequence
<220> FEATURE:
<223> OTHER INFORMATION: primer

<400> SEQUENCE: 46
ttccaccagc taagtgctag cttaaggcgt ggtcgtcag 39

<210> SEQ ID NO 47
<211> LENGTH: 40
<212> TYPE: DNA
<213> ORGANISM: Artificial Sequence
<220> FEATURE:
<223> OTHER INFORMATION: primer

<400> SEQUENCE: 47
cggccagtga attcgagctc cgtaattgcc ctttaaaatt 40

<210> SEQ ID NO 48
<211> LENGTH: 41
<212> TYPE: DNA
<213> ORGANISM: Artificial Sequence
<220> FEATURE:
<223> OTHER INFORMATION: primer

<400> SEQUENCE: 48
gatccccggg taccgcatgc tatattccac cagctatttg t 41

<210> SEQ ID NO 49
<211> LENGTH: 774
<212> TYPE: DNA
<213> ORGANISM: Pseudomonas putida KT2440

<400> SEQUENCE: 49
atgccgcgat atatcgatgt gcaggcgccc gaacatggcg ttcagctcat taccctgcaa 60
cggcccgagg ccttgaatgc cctgtgcacc gagctactgg cagaactggc cgctgcgctg 120
caggctgccg ggaacgacga gcatgtccgt gccacagtga ttaccggcag cgccaaggca 180

-continued ttcgccgcag gcgccgacat ccgcgagatg gccgatcgcg acctggtcgg catcctcaat 240
gacccgcgcg tagcgcattg gcaaagcatc gccgcattcg ccaaaccgct gattgctgca 300
gtcaacggct atgccctggg tggcggttgc gaactggcaa tgtgcgccga catcgtcatc 360
gccagtaccg acgcccgttt cggccagccg gaaatcaacc ttggcatcat ccccggtgct 420
ggcggcaccc agcgcctgtt acgtgccgtc ggtaagccgt tggccatgca gatggtgctg 480
acgggggaag ccatcactgc cctccgcgcc cagcaggccg gcctggtcag cgaaatcacc 540
cagcccgaac tcaccgtaga acgcgccatg caggttgccc gcagcatcgc cgccaaagcg 600
ccgctggctg tgcgcctggc caaggaggcg ttactgaagg ccggtgatac cgacctggcc 660
agcggcctgc gcttcgagcg ccatgccttc accctgctgg cgggcaccgc cgaccgcgat 720
gaaggcatcc gcgccttcca ggaaaagcgc caggcccgct tccaagggcg ctga 774

<210> SEQ ID NO 50
<211> LENGTH: 34
<212> TYPE: DNA
<213> ORGANISM: Artificial Sequence
<220> FEATURE:
<223> OTHER INFORMATION: primer

<400> SEQUENCE: 50
gctggtggaa tatagatgcc gcgatatatc gatg 34

<210> SEQ ID NO 51
<211> LENGTH: 34
<212> TYPE: DNA
<213> ORGANISM: Artificial Sequence
<220> FEATURE:
<223> OTHER INFORMATION: primer

<400> SEQUENCE: 51
attacgccaa gcttgtcagc gcccttggaa gcgg 34

<210> SEQ ID NO 52
<211> LENGTH: 70
<212> TYPE: DNA
<213> ORGANISM: Artificial Sequence
<220> FEATURE:
<223> OTHER INFORMATION: primer

<400> SEQUENCE: 52
gtaatgtttg gcaataagat gaacattatt ttgatgaacc aggggccccc gtgtaggctg 60
gagctgcttc 70

<210> SEQ ID NO 53
<211> LENGTH: 70
<212> TYPE: DNA
<213> ORGANISM: Artificial Sequence
<220> FEATURE:
<223> OTHER INFORMATION: primer

<400> SEQUENCE: 53
gatagctctt atcagcataa ctaatactca attttaccgg ctgatcacgc atgggaatta 60
gccatggtcc 70

<210> SEQ ID NO 54
<211> LENGTH: 20
<212> TYPE: DNA
<213> ORGANISM: Artificial Sequence
<220> FEATURE:
<223> OTHER INFORMATION: primer

<400> SEQUENCE: 54
cggtgccctg aatgaactgc 20

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55
gcagtattga tggcaaagcg 20

<210> SEQ ID NO 56
<211> LENGTH: 20
<212> TYPE: DNA
<213> ORGANISM: Artificial Sequence
<220> FEATURE:
<223> OTHER INFORMATION: primer

<400> SEQUENCE: 56
ctcaattttg gtcgtcatag 20

<210> SEQ ID NO 57
<211> LENGTH: 70
<212> TYPE: DNA
<213> ORGANISM: Artificial Sequence
<220> FEATURE:
<223> OTHER INFORMATION: primer

<400> SEQUENCE: 57
attctcatta tctgaacaat acgcagcacg tctatgacaa agggcgagtt gtgtaggctg 60
gagctgcttc 70

<210> SEQ ID NO 58
<211> LENGTH: 70
<212> TYPE: DNA
<213> ORGANISM: Artificial Sequence
<220> FEATURE:
<223> OTHER INFORMATION: primer

<400> SEQUENCE: 58
cacggaggag aggaggctgt ctctcatccg tgtgcttaag cgaggcaatt atgggaatta 60
gccatggtcc 70

<210> SEQ ID NO 59
<211> LENGTH: 18
<212> TYPE: DNA
<213> ORGANISM: Artificial Sequence
<220> FEATURE:
<223> OTHER INFORMATION: primer

<400> SEQUENCE: 59
ggagcgtgac accatgaa 18

<210> SEQ ID NO 60
<211> LENGTH: 18
<212> TYPE: DNA
<213> ORGANISM: Artificial Sequence
<220> FEATURE:
<223> OTHER INFORMATION: primer

<400> SEQUENCE: 60
cttcacactc aacgcgat 18

<210> SEQ ID NO 61
<211> LENGTH: 70
<212> TYPE: DNA
<213> ORGANISM: Artificial Sequence
<220> FEATURE:
<223> OTHER INFORMATION: primer

<400> SEQUENCE: 61
gctggtttta ttcgtttctt tatccatcac aacttgtaga aaaatccgtc gtgtaggctg 60
gagctgcttc 70

<210> SEQ ID NO 62
<211> LENGTH: 70
<212> TYPE: DNA
<213> ORGANISM: Artificial Sequence
<220> FEATURE:
<223> OTHER INFORMATION: primer

<400> SEQUENCE: 62
aaacgccgca aagcggcgtt tttgacaaaa gaattatgtc acgttttata atgggaatta 60
gccatggtcc 70

<210> SEQ ID NO 63
<211> LENGTH: 20
<212> TYPE: DNA
<213> ORGANISM: Artificial Sequence
<220> FEATURE:
<223> OTHER INFORMATION: primer

<400> SEQUENCE: 63
cgccggtgaa accgtcacga 20

<210> SEQ ID NO 64
<211> LENGTH: 20
<212> TYPE: DNA
<213> ORGANISM: Artificial Sequence
<220> FEATURE:
<223> OTHER INFORMATION: primer

<400> SEQUENCE: 64
gtgctgcgtc gtctttagct 20

<210> SEQ ID NO 65
<211> LENGTH: 1443
<212> TYPE: DNA
<213> ORGANISM: Serratia grimesii NBRC13537

<400> SEQUENCE: 65
atgtccagac ggctcagaag aaccaaaatt gttaccacac tgggtccggc tactgaccgc 60
gacaataatc tggaaaagat cattgccgct ggcgctaacg tagttcggct aaacttttcc 120
catggcagtg ctgaagatca ccaagctcgc gctgacaaag tgcgcgaaat tgctgccaag 180
ttgggacgtc acgtcgctat tctgggtgac ctgcaagggc cgaagattcg tgtttccacc 240
tttaaggaag gcaaaatatt ccttaacatc ggtgacaaat tcctgctcga tgccaacatg 300
tccaaaggcg aaggcgataa agaaaaagtc ggtatcgact ataaaggcct gcctgccgat 360
gttgtgccgg gcgatgtgct gctgctggac gatggccgcg tacagttgaa agtgctcgaa 420
gttcagggca tgaaagtctt caccgaagtg accgttggcg gcccactgtc caacaacaaa 480
ggtatcaaca aactcggtgg tggcctgtcc gctgaagccc tgaccgagaa agacaaagcc 540

-continued gatatcgtca ctgcagcaaa aatcggcgtt gactacctgg ctgtttcctt cccacgtacc 600
ggcgaagacc tgaactacgc acgccgcttg gcacgcgatg ccggctgcaa tgccaagatc 660
gtatccaagg ttgagcgcgc cgaagccgtg tgcagcgacg aagctatgga tgacatcatc 720
ctggcttctg acgtagtcat ggtagcacgt ggcgatctgg gcgtcgaaat cggcgatcct 780
gagctggtcg gcatccagaa aaaactgatc cgccgtgccc gtacactgaa ccgcgccgtg 840
attaccgcta cccagatgat ggaatcgatg atcaccaacc cgatgcctac ccgcgccgaa 900
gtcatggacg tggcgaacgc cgtgctggat ggtaccgacg ccgttatgct gtctgctgaa 960
accgcagccg gtcaataccc ggcggaaacc gtggctgcga tggcccgtgt ttgcctgggc 1020
gcggagaaga tccctagcat caatgtctcc aaacaccgcc tggacgtgca atttgacaac 1080
attgaagagg ctatcgccat gtcttcaatg tacgcggcaa accatctgaa aggggttacc 1140
gcactgatcg ccatgaccga gtccgggcgc actgctctga tgatgtcacg catcagttcc 1200
ggcctgccta tcttcgccat gtcacgtcat gagcacacac tgaacctgac tgcactgtac 1260
cgcggtgtta caccggtgta cttcgatagc cacgaagacg gcgtcatcgc tgccaacgac 1320
gcggttaatc gcctgcgtga taaaggcttc ctggtctctg gcgatttagt gatcgttacc 1380
cagggcgacg taatggaaac cgttggtacg accaatacca gccgtatttt gcgcgtcgaa 1440
taa 1443

<210> SEQ ID NO 66
<211> LENGTH: 70
<212> TYPE: DNA
<213> ORGANISM: Artificial Sequence
<220> FEATURE:
<223> OTHER INFORMATION: primer

<400> SEQUENCE: 66
gacgttatcg caacaccaat aatttgcttc accagtcaac ggagtaatac gtgtaggctg 60
gagctgcttc 70

<210> SEQ ID NO 67
<211> LENGTH: 70
<212> TYPE: DNA
<213> ORGANISM: Artificial Sequence
<220> FEATURE:
<223> OTHER INFORMATION: primer

<400> SEQUENCE: 67
cagtcaggtt cagtgtgtgc tcatgacgtg acatggcgaa gataggcagg atgggaatta 60
gccatggtcc 70

<210> SEQ ID NO 68
<211> LENGTH: 20
<212> TYPE: DNA
<213> ORGANISM: Artificial Sequence
<220> FEATURE:
<223> OTHER INFORMATION: primer

<400> SEQUENCE: 68
tggtggaaat ggcgcagctt 20

<210> SEQ ID NO 69
<211> LENGTH: 20
<212> TYPE: DNA
<213> ORGANISM: Artificial Sequence
<220> FEATURE:

<223> OTHER INFORMATION: primer

<400> SEQUENCE: 69
gcgtaaccga cccaattcga 20

<210> SEQ ID NO 70
<211> LENGTH: 67
<212> TYPE: DNA
<213> ORGANISM: Artificial Sequence
<220> FEATURE:
<223> OTHER INFORMATION: primer

<400> SEQUENCE: 70
gaaagcaagt ttctcccatc cttctcaact taaagactaa gactgtcgtg taggctggag 60
ctgcttc 67

<210> SEQ ID NO 71
<211> LENGTH: 70
<212> TYPE: DNA
<213> ORGANISM: Artificial Sequence
<220> FEATURE:
<223> OTHER INFORMATION: primer

<400> SEQUENCE: 71
cgcccatcag ggcgcttcga tatacaaatt aattcacaaa agcaatatta atgggaatta 60
gccatggtcc 70

<210> SEQ ID NO 72
<211> LENGTH: 18
<212> TYPE: DNA
<213> ORGANISM: Artificial Sequence
<220> FEATURE:
<223> OTHER INFORMATION: primer

<400> SEQUENCE: 72
ccggatgaac tttcactt 18

<210> SEQ ID NO 73
<211> LENGTH: 18
<212> TYPE: DNA
<213> ORGANISM: Artificial Sequence
<220> FEATURE:
<223> OTHER INFORMATION: primer

<400> SEQUENCE: 73
gagctgcgtc atctttag 18

<210> SEQ ID NO 74
<211> LENGTH: 1443
<212> TYPE: DNA
<213> ORGANISM: Escherichia coli str. K-12 substr. MG1655

<400> SEQUENCE: 74
atgtccagaa ggcttcgcag aacaaaaatc gttaccacgt taggcccagc aacagatcgc 60
gataataatc ttgaaaaagt tatcgcggcg ggtgccaacg ttgtacgtat gaacttttct 120
cacggctcgc ctgaagatca caaaatgcgc gcggataaag ttcgtgagat tgccgcaaaa 180
ctggggcgtc atgtggctat tctgggtgac ctccaggggc ccaaaatccg tgtatccacc 240
tttaaagaag gcaaagtttt cctcaatatt ggggataaat tcctgctcga cgccaacctg 300
ggtaaaggtg aaggcgacaa agaaaaagtc ggtatcgact acaaaggcct gcctgctgac 360
gtcgtgcctg gtgacatcct gctgctggac gatggtcgcg tccagttaaa agtactggaa 420

-continued

```
gttcagggca tgaaagtgtt caccgaagtc accgtcggtg gtcccctctc caacaataaa    480

ggtatcaaca aacttggcgg cggtttgtcg gctgaagcgc tgaccgaaaa agacaaagca    540

gacattaaga ctgcggcgtt gattggcgta gattacctgg ctgtctcctt cccacgctgt    600

ggcgaagatc tgaactatgc ccgtcgcctg gcacgcgatg caggatgtga tgcgaaaatt    660

gttgccaagg ttgaacgtgc ggaagccgtt tgcagccagg atgcaatgga tgacatcatc    720

ctcgcctctg acgtggtaat ggttgcacgt ggcgacctcg gtgtggaaat tggcgacccg    780

gaactggtcg gcattcagaa agcgttgatc cgtcgtgcgc gtcagctaaa ccgagcggta    840

atcacggcga cccagatgat ggagtcaatg attactaacc cgatgccgac gcgtgcagaa    900

gtcatggacg tagcaaacgc cgttctggat ggtactgacg ctgtgatgct gtctgcagaa    960

actgccgctg ggcagtatcc gtcagaaacc gttgcagcca tggcgcgcgt ttgcctgggt   1020

gcggaaaaaa tcccgagcat caacgtttct aaacaccgtc tggacgttca gttcgacaat   1080

gtggaagaag ctattgccat gtcagcaatg tacgcagcta accacctgaa aggcgttacg   1140

gcgatcatca ccatgaccga atcgggtcgt accgcgctga tgacctcccg tatcagctct   1200

ggtctgccaa ttttcgccat gtcgcgccat gaacgtacgc tgaacctgac tgctctctat   1260

cgtggcgtta cgccggtgca ctttgatagc gctaatgacg gcgtagcagc tgccagcgaa   1320

gcggttaatc tgctgcgcga taaaggttac ttgatgtctg gtgacctggt gattgtcacc   1380

cagggcgacg tgatgagtac cgtgggttct actaatacca cgcgtatttt aacggtagag   1440

taa                                                                  1443
```

<210> SEQ ID NO 75
<211> LENGTH: 70
<212> TYPE: DNA
<213> ORGANISM: Artificial Sequence
<220> FEATURE:
<223> OTHER INFORMATION: primer

<400> SEQUENCE: 75

```
ggatttcatg ttcaagcaac acctggttgt ttcagtcaac ggagtattac gtgtaggctg     60

gagctgcttc                                                            70
```

<210> SEQ ID NO 76
<211> LENGTH: 70
<212> TYPE: DNA
<213> ORGANISM: Artificial Sequence
<220> FEATURE:
<223> OTHER INFORMATION: primer

<400> SEQUENCE: 76

```
tgaactgtag gccggatgtg gcgttttcgc cgcatccggc aacgtactta atgggaatta     60

gccatggtcc                                                            70
```

<210> SEQ ID NO 77
<211> LENGTH: 18
<212> TYPE: DNA
<213> ORGANISM: Artificial Sequence
<220> FEATURE:
<223> OTHER INFORMATION: primer

<400> SEQUENCE: 77

```
acgcatgagt tgtatgaa                                                   18
```

<210> SEQ ID NO 78

-continued

<211> LENGTH: 18
<212> TYPE: DNA
<213> ORGANISM: Artificial Sequence
<220> FEATURE:
<223> OTHER INFORMATION: primer

<400> SEQUENCE: 78
ttacccgatc aggatcat 18

<210> SEQ ID NO 79
<211> LENGTH: 1628
<212> TYPE: DNA
<213> ORGANISM: Escherichia coli str. K-12 substr. MG1655

<400> SEQUENCE: 79
acattaaaaa acgtgcccgg ttatctatta tcctgattcg taaaggccaa acaataaatt 60
cattatgatg ataatattca tgtgatagtt tgtttgcggc gagagataat tcgcttttta 120
tcaccgagct tctcccgata accaggatta atcagcgcaa ttttgatctt aacctaccgc 180
aaaacaaccg tgcttcatga tacaaatgga ttctcattat ctgaacaata cgcagcacgt 240
ctatgacaaa gggcgagtta tgcaaactga gcaacagcga gccgtaacac ggctttgtat 300
ccagtgtgga ttatttcttt tgcaacatgg tgcggaaagc gcgttggttg atgagctttc 360
ctcacgactg ggtcgggcac tgggaatgga cagcgtcgaa agttctatct cttcgaacgc 420
catagtgctg acaactatta aagatgggca atgcctgaca tcgacacgta aaaatcacga 480
tcgcggcatt aatatgcatg tggtgactga agtccagcac attgtgattc ttgcggagca 540
tcatctgctg gattacaaag gcgtagagaa acgatttagc caaattcagc cattacgtta 600
cccaagatgg ctggtagcct taatggttgg cctttcttgc gcctgtttct gtaaactcaa 660
taacggtggc tgggatggtg ccgtcatcac cttctttgcc agtacgaccg cgatgtatat 720
ccgccagctg ctggcacaac gtcatcttca tccacagatc aacttttgcc ttaccgcttt 780
cgccgccacc accatttccg gattgctttt gcaactcccc actttcagca ataccccac 840 cattgcgatg gccgccagcg ttctgctgct agtgccgggc tttccgttga ttaatgccgt 900
cgccgatatg tttaaaggcc acatcaatac cggactggca cgctgggcga tcgccagtct 960
gctgacactg gctacctgcg tcggcgtagt gatggcactg acgatttggg ggctacgcgg 1020
atgggtgtga tcgaatttct gttagcgttg gcgcaggata tgatcctcgc cgccattcct 1080
gcggtcggct ttgcgatggt gttcaacgtt cccgtgcggg cgttacgctg gtgtgcgctg 1140
cttggctcga taggtcatgg ttcccgaatg atcttgatga ccagcgggtt gaatattgag 1200
tggtcaacct ttatggcttc tatgctggtc ggtaccattg gtattcaatg gtcgcgctgg 1260
tatctggcgc atccgaaagt gtttaccgtg gcggccgtta tccctatgtt cccgggcata 1320
tcggcttata ccgcaatgat ttcggcggta aaaatcagcc agttaggtta cagcgaaccg 1380
ttgatgatta ccctgttaac caactttctt acagcttcat cgattgttgg tgcgttatcc 1440
atcggtcttt ccattcctgg attatggttg taccgcaagc gccctcgcgt ataaaattgc 1500
ctcgcttaag cacacggatg agagacagcc tcctctcctc cgtgtgttac tataaaagtt 1560
atctcccttc tcgttcatcg ttccatattt gagaaacagt atgtcttcca gagttttgac 1620
cccggacg 1628

<210> SEQ ID NO 80
<211> LENGTH: 35
<212> TYPE: DNA
<213> ORGANISM: Artificial Sequence
<220> FEATURE:
<223> OTHER INFORMATION: primer

<400> SEQUENCE: 80
ctgaaccgct ctagaacatt aaaaaacgtg cccgg 35

<210> SEQ ID NO 81
<211> LENGTH: 35
<212> TYPE: DNA
<213> ORGANISM: Artificial Sequence
<220> FEATURE:
<223> OTHER INFORMATION: primer

<400> SEQUENCE: 81
tgcggccgca agcttcgtcc ggggtcaaaa ctctg 35

<210> SEQ ID NO 82
<211> LENGTH: 70
<212> TYPE: DNA
<213> ORGANISM: Artificial Sequence
<220> FEATURE:
<223> OTHER INFORMATION: primer

<400> SEQUENCE: 82
ggccgacaga tgagttatga gcgcttttaa tctcattacg gagtttctgc gtgtaggctg 60
gagctgcttc 70

<210> SEQ ID NO 83
<211> LENGTH: 70
<212> TYPE: DNA
<213> ORGANISM: Artificial Sequence
<220> FEATURE:
<223> OTHER INFORMATION: primer

<400> SEQUENCE: 83
ttatccttgc tgaatcgaag cagcagcaag atgattctga agttcaggaa atgggaatta 60
gccatggtcc 70

<210> SEQ ID NO 84
<211> LENGTH: 20
<212> TYPE: DNA
<213> ORGANISM: Artificial Sequence
<220> FEATURE:
<223> OTHER INFORMATION: primer

<400> SEQUENCE: 84
acacccgccg aaaaattacg 20

<210> SEQ ID NO 85
<211> LENGTH: 20
<212> TYPE: DNA
<213> ORGANISM: Artificial Sequence
<220> FEATURE:
<223> OTHER INFORMATION: primer

<400> SEQUENCE: 85
tacttcgctt cgccgttttt 20

<210> SEQ ID NO 86
<211> LENGTH: 70
<212> TYPE: DNA
<213> ORGANISM: Artificial Sequence
<220> FEATURE:
<223> OTHER INFORMATION: primer

<400> SEQUENCE: 86
ctaccctatg tataagcctg atctacaggc atatttagca aggatttcaa gtgtaggctg 60
gagctgcttc 70

<210> SEQ ID NO 87
<211> LENGTH: 70
<212> TYPE: DNA
<213> ORGANISM: Artificial Sequence
<220> FEATURE:
<223> OTHER INFORMATION: primer

<400> SEQUENCE: 87
gagctggcaa taagtccgga cgggtattta ccgcagtccg gacttatttt atgggaatta 60
gccatggtcc 70

<210> SEQ ID NO 88
<211> LENGTH: 20
<212> TYPE: DNA
<213> ORGANISM: Artificial Sequence
<220> FEATURE:
<223> OTHER INFORMATION: primer

<400> SEQUENCE: 88
tgttcatttc gcgggtttgt 20

<210> SEQ ID NO 89
<211> LENGTH: 20
<212> TYPE: DNA
<213> ORGANISM: Artificial Sequence
<220> FEATURE:
<223> OTHER INFORMATION: primer

<400> SEQUENCE: 89
gtcgtagtct ctgcagcaaa 20

<210> SEQ ID NO 90
<211> LENGTH: 1059
<212> TYPE: DNA
<213> ORGANISM: Escherichia coli str. K-12 substr. MG1655
<220> FEATURE:
<221> NAME/KEY: CDS
<222> LOCATION: (1)..(1059)

<400> SEQUENCE: 90

```
gtg cgt gcc gat aag tca tta agc ccg ttt gaa atc cgg gta tac cgc       48
Met Arg Ala Asp Lys Ser Leu Ser Pro Phe Glu Ile Arg Val Tyr Arg
1               5                   10                  15

cat tac cgc att gtg cat ggt act cgg gtc gcg ctg gca ttc ctg ctc       96
His Tyr Arg Ile Val His Gly Thr Arg Val Ala Leu Ala Phe Leu Leu
            20                  25                  30

act ttt ctc att atc cgc ctg ttt act atc ccg gaa agc acc tgg ccg      144
Thr Phe Leu Ile Ile Arg Leu Phe Thr Ile Pro Glu Ser Thr Trp Pro
        35                  40                  45

ctg gtc acc atg gtg gtg att atg ggg cca atc tcg ttc tgg ggt aac      192
Leu Val Thr Met Val Val Ile Met Gly Pro Ile Ser Phe Trp Gly Asn
    50                  55                  60

gtt gtc cct cgc gcc ttt gag cgt att ggc ggt acg gtg ttg ggt tcg      240
Val Val Pro Arg Ala Phe Glu Arg Ile Gly Gly Thr Val Leu Gly Ser
65                  70                  75                  80

att tta ggt ctt atc gct ctg caa ctg gag tta atc tcg tta ccg ctg      288
Ile Leu Gly Leu Ile Ala Leu Gln Leu Glu Leu Ile Ser Leu Pro Leu
                85                  90                  95
```

-continued

```
atg tta gtc tgg tgc gcg gcg gcc atg ttc ctt tgc ggt tgg ctg gcg      336
Met Leu Val Trp Cys Ala Ala Ala Met Phe Leu Cys Gly Trp Leu Ala
            100                 105                 110

ctg ggc aag aaa ccg tat caa ggt tta ttg att ggg gtg acg ctg gca      384
Leu Gly Lys Lys Pro Tyr Gln Gly Leu Leu Ile Gly Val Thr Leu Ala
        115                 120                 125

att gtt gtg ggt tcc ccg aca ggt gaa att gat acg gcg tta tgg cga      432
Ile Val Val Gly Ser Pro Thr Gly Glu Ile Asp Thr Ala Leu Trp Arg
    130                 135                 140

agc ggc gat gtg atc ctc ggc tct tta ctg gca atg ttg ttt acc ggt      480
Ser Gly Asp Val Ile Leu Gly Ser Leu Leu Ala Met Leu Phe Thr Gly
145                 150                 155                 160

atc tgg cca caa cgg gcg ttc atc cac tgg cgc att caa ctg gcg aaa      528
Ile Trp Pro Gln Arg Ala Phe Ile His Trp Arg Ile Gln Leu Ala Lys
                165                 170                 175

agt ctg acc gag tat aat cgg gtc tat caa tct gca ttc tca ccg aac      576
Ser Leu Thr Glu Tyr Asn Arg Val Tyr Gln Ser Ala Phe Ser Pro Asn
            180                 185                 190

tta ctc gaa cgc cca cgt ctg gaa agc cat cta caa aaa ctc ctg acc      624
Leu Leu Glu Arg Pro Arg Leu Glu Ser His Leu Gln Lys Leu Leu Thr
        195                 200                 205

gat gcc gtg aaa atg cgt gga ctg att gcg ccc gcc agc aaa gaa acc      672
Asp Ala Val Lys Met Arg Gly Leu Ile Ala Pro Ala Ser Lys Glu Thr
    210                 215                 220

cgt att cca aaa tcg ata tat gaa ggt atc cag acc att aac cgc aat      720
Arg Ile Pro Lys Ser Ile Tyr Glu Gly Ile Gln Thr Ile Asn Arg Asn
225                 230                 235                 240

ctg gtt tgt atg ctg gag ttg caa atc aat gca tac tgg gcc acg cgc      768
Leu Val Cys Met Leu Glu Leu Gln Ile Asn Ala Tyr Trp Ala Thr Arg
                245                 250                 255

ccc agc cat ttc gtg tta ttg aac gcg caa aaa ctt cgt gat acc cag      816
Pro Ser His Phe Val Leu Leu Asn Ala Gln Lys Leu Arg Asp Thr Gln
            260                 265                 270

cac atg atg cag caa ata ctg ctg agc ctt gtt cat gcg ctg tac gaa      864
His Met Met Gln Gln Ile Leu Leu Ser Leu Val His Ala Leu Tyr Glu
        275                 280                 285

ggt aat ccg cag ccg gtt ttt gcc aat acg gaa aaa ttg aac gat gct      912
Gly Asn Pro Gln Pro Val Phe Ala Asn Thr Glu Lys Leu Asn Asp Ala
    290                 295                 300

gtg gaa gag ctg cgt cag ttg ctc aat aac cac cat gac ctg aag gtt      960
Val Glu Glu Leu Arg Gln Leu Leu Asn Asn His His Asp Leu Lys Val
305                 310                 315                 320

gtg gaa aca cca atc tat ggt tat gtg tgg ctg aac atg gaa acg gcg     1008
Val Glu Thr Pro Ile Tyr Gly Tyr Val Trp Leu Asn Met Glu Thr Ala
                325                 330                 335

cat cag ctt gag ttg cta tcg aat ctg att tgc cgg gcc ttg cgc aaa     1056
His Gln Leu Glu Leu Leu Ser Asn Leu Ile Cys Arg Ala Leu Arg Lys
            340                 345                 350

taa                                                                 1059


<210> SEQ ID NO 91
<211> LENGTH: 352
<212> TYPE: PRT
<213> ORGANISM: Escherichia coli str. K-12 substr. MG1655

<400> SEQUENCE: 91

Met Arg Ala Asp Lys Ser Leu Ser Pro Phe Glu Ile Arg Val Tyr Arg
1               5                   10                  15

His Tyr Arg Ile Val His Gly Thr Arg Val Ala Leu Ala Phe Leu Leu
            20                  25                  30
```

-continued

```
Thr Phe Leu Ile Ile Arg Leu Phe Thr Ile Pro Glu Ser Thr Trp Pro
        35                  40                  45

Leu Val Thr Met Val Val Ile Met Gly Pro Ile Ser Phe Trp Gly Asn
    50                  55                  60

Val Val Pro Arg Ala Phe Glu Arg Ile Gly Gly Thr Val Leu Gly Ser
65                  70                  75                  80

Ile Leu Gly Leu Ile Ala Leu Gln Leu Glu Leu Ile Ser Leu Pro Leu
                85                  90                  95

Met Leu Val Trp Cys Ala Ala Ala Met Phe Leu Cys Gly Trp Leu Ala
            100                 105                 110

Leu Gly Lys Lys Pro Tyr Gln Gly Leu Leu Ile Gly Val Thr Leu Ala
        115                 120                 125

Ile Val Val Gly Ser Pro Thr Gly Glu Ile Asp Thr Ala Leu Trp Arg
    130                 135                 140

Ser Gly Asp Val Ile Leu Gly Ser Leu Leu Ala Met Leu Phe Thr Gly
145                 150                 155                 160

Ile Trp Pro Gln Arg Ala Phe Ile His Trp Arg Ile Gln Leu Ala Lys
                165                 170                 175

Ser Leu Thr Glu Tyr Asn Arg Val Tyr Gln Ser Ala Phe Ser Pro Asn
            180                 185                 190

Leu Leu Glu Arg Pro Arg Leu Glu Ser His Leu Gln Lys Leu Leu Thr
        195                 200                 205

Asp Ala Val Lys Met Arg Gly Leu Ile Ala Pro Ala Ser Lys Glu Thr
    210                 215                 220

Arg Ile Pro Lys Ser Ile Tyr Glu Gly Ile Gln Thr Ile Asn Arg Asn
225                 230                 235                 240

Leu Val Cys Met Leu Glu Leu Gln Ile Asn Ala Tyr Trp Ala Thr Arg
                245                 250                 255

Pro Ser His Phe Val Leu Leu Asn Ala Gln Lys Leu Arg Asp Thr Gln
            260                 265                 270

His Met Met Gln Gln Ile Leu Leu Ser Leu Val His Ala Leu Tyr Glu
        275                 280                 285

Gly Asn Pro Gln Pro Val Phe Ala Asn Thr Glu Lys Leu Asn Asp Ala
    290                 295                 300

Val Glu Glu Leu Arg Gln Leu Leu Asn Asn His His Asp Leu Lys Val
305                 310                 315                 320

Val Glu Thr Pro Ile Tyr Gly Tyr Val Trp Leu Asn Met Glu Thr Ala
                325                 330                 335

His Gln Leu Glu Leu Leu Ser Asn Leu Ile Cys Arg Ala Leu Arg Lys
            340                 345                 350


<210> SEQ ID NO 92
<211> LENGTH: 1254
<212> TYPE: DNA
<213> ORGANISM: Escherichia coli str. K-12 substr. MG1655
<220> FEATURE:
<221> NAME/KEY: CDS
<222> LOCATION: (1)..(1254)

<400> SEQUENCE: 92

gtg agc cgt act aca act gtt gat ggc gct ccg gca agc gac act gac       48
Met Ser Arg Thr Thr Thr Val Asp Gly Ala Pro Ala Ser Asp Thr Asp
1               5                   10                  15

aag caa agc att tct cag cca aat caa ttt att aaa cgc ggt acg ccg       96
Lys Gln Ser Ile Ser Gln Pro Asn Gln Phe Ile Lys Arg Gly Thr Pro
            20                  25                  30
```

-continued

```
caa ttt atg cgc gtc acc ctg gcg ctg ttc tct gcc gga ctg gca aca      144
Gln Phe Met Arg Val Thr Leu Ala Leu Phe Ser Ala Gly Leu Ala Thr
        35                  40                  45

ttt gca ctt ctc tat tgt gtg cag cct atc ctt ccg gtg ctt tcg cag      192
Phe Ala Leu Leu Tyr Cys Val Gln Pro Ile Leu Pro Val Leu Ser Gln
    50                  55                  60

gag ttt ggc tta acc ccc gcg aac agt agt att tca ctg tcc att tcc      240
Glu Phe Gly Leu Thr Pro Ala Asn Ser Ser Ile Ser Leu Ser Ile Ser
65                  70                  75                  80

acg gcg atg ttg gct att ggt ttg ctg ttt act ggc ccg cta tcc gat      288
Thr Ala Met Leu Ala Ile Gly Leu Leu Phe Thr Gly Pro Leu Ser Asp
                85                  90                  95

gcc att ggt cgc aaa cca gtg atg gtc acg gcg cta ctg ttg gcc tcc      336
Ala Ile Gly Arg Lys Pro Val Met Val Thr Ala Leu Leu Leu Ala Ser
            100                 105                 110

att tgt acg tta ctt tcg aca atg atg acc agc tgg cac ggc att ttg      384
Ile Cys Thr Leu Leu Ser Thr Met Met Thr Ser Trp His Gly Ile Leu
        115                 120                 125

att atg cgc gcc ttg att ggg ctt tcg tta agt ggc gtg gca gct gtt      432
Ile Met Arg Ala Leu Ile Gly Leu Ser Leu Ser Gly Val Ala Ala Val
    130                 135                 140

ggc atg act tat ctt agc gag gaa atc cat ccc agt ttc gtg gcc ttt      480
Gly Met Thr Tyr Leu Ser Glu Glu Ile His Pro Ser Phe Val Ala Phe
145                 150                 155                 160

tca atg ggg ttg tat atc agc ggc aac tca att ggc ggc atg agc gga      528
Ser Met Gly Leu Tyr Ile Ser Gly Asn Ser Ile Gly Gly Met Ser Gly
                165                 170                 175

cgc tta att agc ggt gtc ttc acg gac ttt ttc aac tgg cga att gct      576
Arg Leu Ile Ser Gly Val Phe Thr Asp Phe Phe Asn Trp Arg Ile Ala
            180                 185                 190

ctg gcg gca atc ggt tgt ttc gcg ctg gcc tcg gcg ttg atg ttc tgg      624
Leu Ala Ala Ile Gly Cys Phe Ala Leu Ala Ser Ala Leu Met Phe Trp
        195                 200                 205

aaa atc ctc cct gaa tca cgc cat ttt cgc ccg act tcg ctg cgc cct      672
Lys Ile Leu Pro Glu Ser Arg His Phe Arg Pro Thr Ser Leu Arg Pro
    210                 215                 220

aag acg ttg ttt atc aac ttt cgt ctg cac tgg cgt gac cgg gga tta      720
Lys Thr Leu Phe Ile Asn Phe Arg Leu His Trp Arg Asp Arg Gly Leu
225                 230                 235                 240

ccg tta ttg ttc gca gaa ggc ttt ttg ctg atg ggg tcg ttc gtc acg      768
Pro Leu Leu Phe Ala Glu Gly Phe Leu Leu Met Gly Ser Phe Val Thr
                245                 250                 255

ctg ttt aat tac atc ggc tat cgg ttg atg ctc tcc ccc tgg cat gtc      816
Leu Phe Asn Tyr Ile Gly Tyr Arg Leu Met Leu Ser Pro Trp His Val
            260                 265                 270

agt cag gcc gtg gtt ggc tta tta tcg ctg gct tat ttg acc ggt aca      864
Ser Gln Ala Val Val Gly Leu Leu Ser Leu Ala Tyr Leu Thr Gly Thr
        275                 280                 285

tgg agc tca ccc aaa gcc gga acc atg acc acc cgc tat ggg cgt ggt      912
Trp Ser Ser Pro Lys Ala Gly Thr Met Thr Thr Arg Tyr Gly Arg Gly
    290                 295                 300

cca gtg atg ttg ttt tcg acg ggg gtt atg ctg ttt ggt tta ctg atg      960
Pro Val Met Leu Phe Ser Thr Gly Val Met Leu Phe Gly Leu Leu Met
305                 310                 315                 320

acc tta ttc agc tcg ctg tgg ctg atc ttt gcc gga atg tta ctc ttc     1008
Thr Leu Phe Ser Ser Leu Trp Leu Ile Phe Ala Gly Met Leu Leu Phe
                325                 330                 335

tca gca gga ttc ttc gca gcc cac tca gta gcc agc agc tgg atc ggc     1056
Ser Ala Gly Phe Phe Ala Ala His Ser Val Ala Ser Ser Trp Ile Gly
```

```
            340                 345                 350

ccc cgc gca aaa cgc gct aaa ggc cag gcc tcc tcg ctg tat ctg ttc      1104
Pro Arg Ala Lys Arg Ala Lys Gly Gln Ala Ser Ser Leu Tyr Leu Phe
        355                 360                 365

agt tac tat ctg ggg tcg agt att gcc ggg acg ctg ggt ggt gtt ttc      1152
Ser Tyr Tyr Leu Gly Ser Ser Ile Ala Gly Thr Leu Gly Gly Val Phe
    370                 375                 380

tgg cat aac tat ggc tgg aac ggc gtc ggc gca ttt att gct ctg atg      1200
Trp His Asn Tyr Gly Trp Asn Gly Val Gly Ala Phe Ile Ala Leu Met
385                 390                 395                 400

ctg gtc att gct ctg ctg gtc ggg acg cgt ttg cat cgt cgt ctg cac      1248
Leu Val Ile Ala Leu Leu Val Gly Thr Arg Leu His Arg Arg Leu His
                405                 410                 415

gcc tga                                                              1254
Ala


<210> SEQ ID NO 93
<211> LENGTH: 417
<212> TYPE: PRT
<213> ORGANISM: Escherichia coli str. K-12 substr. MG1655

<400> SEQUENCE: 93

Met Ser Arg Thr Thr Thr Val Asp Gly Ala Pro Ala Ser Asp Thr Asp
1               5                   10                  15

Lys Gln Ser Ile Ser Gln Pro Asn Gln Phe Ile Lys Arg Gly Thr Pro
            20                  25                  30

Gln Phe Met Arg Val Thr Leu Ala Leu Phe Ser Ala Gly Leu Ala Thr
        35                  40                  45

Phe Ala Leu Leu Tyr Cys Val Gln Pro Ile Leu Pro Val Leu Ser Gln
    50                  55                  60

Glu Phe Gly Leu Thr Pro Ala Asn Ser Ser Ile Ser Leu Ser Ile Ser
65                  70                  75                  80

Thr Ala Met Leu Ala Ile Gly Leu Leu Phe Thr Gly Pro Leu Ser Asp
                85                  90                  95

Ala Ile Gly Arg Lys Pro Val Met Val Thr Ala Leu Leu Leu Ala Ser
            100                 105                 110

Ile Cys Thr Leu Leu Ser Thr Met Met Thr Ser Trp His Gly Ile Leu
        115                 120                 125

Ile Met Arg Ala Leu Ile Gly Leu Ser Leu Ser Gly Val Ala Ala Val
    130                 135                 140

Gly Met Thr Tyr Leu Ser Glu Glu Ile His Pro Ser Phe Val Ala Phe
145                 150                 155                 160

Ser Met Gly Leu Tyr Ile Ser Gly Asn Ser Ile Gly Gly Met Ser Gly
                165                 170                 175

Arg Leu Ile Ser Gly Val Phe Thr Asp Phe Phe Asn Trp Arg Ile Ala
            180                 185                 190

Leu Ala Ala Ile Gly Cys Phe Ala Leu Ala Ser Ala Leu Met Phe Trp
        195                 200                 205

Lys Ile Leu Pro Glu Ser Arg His Phe Arg Pro Thr Ser Leu Arg Pro
    210                 215                 220

Lys Thr Leu Phe Ile Asn Phe Arg Leu His Trp Arg Asp Arg Gly Leu
225                 230                 235                 240

Pro Leu Leu Phe Ala Glu Gly Phe Leu Leu Met Gly Ser Phe Val Thr
                245                 250                 255

Leu Phe Asn Tyr Ile Gly Tyr Arg Leu Met Leu Ser Pro Trp His Val
            260                 265                 270
```

-continued

```
Ser Gln Ala Val Val Gly Leu Leu Ser Leu Ala Tyr Leu Thr Gly Thr
        275                 280                 285

Trp Ser Ser Pro Lys Ala Gly Thr Met Thr Thr Arg Tyr Gly Arg Gly
    290                 295                 300

Pro Val Met Leu Phe Ser Thr Gly Val Met Leu Phe Gly Leu Leu Met
305                 310                 315                 320

Thr Leu Phe Ser Ser Leu Trp Leu Ile Phe Ala Gly Met Leu Leu Phe
                325                 330                 335

Ser Ala Gly Phe Phe Ala Ala His Ser Val Ala Ser Ser Trp Ile Gly
            340                 345                 350

Pro Arg Ala Lys Arg Ala Lys Gly Gln Ala Ser Ser Leu Tyr Leu Phe
        355                 360                 365

Ser Tyr Tyr Leu Gly Ser Ser Ile Ala Gly Thr Leu Gly Gly Val Phe
    370                 375                 380

Trp His Asn Tyr Gly Trp Asn Gly Val Gly Ala Phe Ile Ala Leu Met
385                 390                 395                 400

Leu Val Ile Ala Leu Leu Val Gly Thr Arg Leu His Arg Arg Leu His
                405                 410                 415

Ala
```

GENETICALLY MODIFIED MICROORGANISM FOR PRODUCING 3-HYDROXYHEXANEDIOIC ACID AND/OR (E)-HEX-2-ENEDIOIC ACID AND PRODUCTION METHOD FOR SAID CHEMICALS

TECHNICAL FIELD

The present invention relates to a genetically modified microorganism that abundantly produces 3-hydroxyadipic acid and/or α-hydromuconic acid, and to a method of producing 3-hydroxyadipic acid and/or α-hydromuconic acid using the genetically modified microorganism.

BACKGROUND ART

3-Hydroxyadipic acid (IUPAC name: 3-hydroxyhexanedioic acid) and α-hydromuconic acid (IUPAC name: (E)-hex-2-enedioic acid) are $C_6$ dicarboxylic acids. These dicarboxylic acids can be used as raw materials for the production of polyesters by polymerization with polyhydric alcohols or as raw materials for the production of polyamides by polymerization with polyfunctional amines. Additionally, a compound lactamized by adding ammonia to the end of such a dicarboxylic acid can be used as a raw material for a polyamide.

Examples of the literature relating to the production of a $C_6$ dicarboxylic acid using a microorganism include Patent Document 1 that describes a method of producing 3-hydroxyadipic acid, α-hydromuconic acid, and/or adipic acid using a polypeptide having an excellent activity that catalyzes a reaction to reduce 3-oxoadipyl-CoA to 3-hydroxyadipyl-CoA. The Document describes a biosynthesis pathway through which these substances undergo an enzymatic reaction to reduce 3-oxoadipyl-CoA to 3-hydroxyadipyl-CoA. In Patent Document 1, any gene to be modified is limited to an intracellular reaction in the above-mentioned biosynthesis pathway, and there is no mention of transporting 3-hydroxyadipic acid, α-hydromuconic acid, and/or adipic acid out of a cell.

Patent Document 2 describes a method of producing dicarboxylic acid using a bacterium modified to increase the expression level of dicarboxylic acid excretion carrier genes yjP, yjjB, yeeA, and ynfM, and mentions succinic acid as an example of a $C_4$ dicarboxylic acid and adipic acid as an example of a $C_6$ dicarboxylic acid.

PRIOR ART DOCUMENTS

Patent Documents

Patent Document 1: EP 3719121 A1
Patent Document 2: JP 2017-216881 A

SUMMARY OF THE INVENTION

Problems to be Solved by the Invention

An object of the present invention is to provide a genetically modified microorganism for producing 3-hydroxyadipic acid and/or α-hydromuconic acid with a high yield; and a method of producing a substance using the modified microorganism, wherein the genetically modified microorganism is based on a microorganism in which a 3-oxoadipyl-CoA reducing enzyme gene is introduced, or the expression of the gene is enhanced, so that the enzyme activity is enhanced, and furthermore, in which a dicarboxylic acid excretion carrier is modified.

Means for Solving the Problem

The inventors have intensively studied to achieve the above-described object, and consequently have come to complete the present invention through the discovery that, contrary to the prediction by conventional technologies, a genetically modified microorganism in which a dicarboxylic acid excretion carrier function is deleted or decreased has an excellent ability to produce 3-hydroxyadipic acid and/or α-hydromuconic acid.

That is, the present invention provides the following:

(1) A genetically modified microorganism having an ability to produce 3-hydroxyadipic acid and/or α-hydromuconic acid, and having an enhanced enzymatic activity to catalyze a reaction to reduce 3-oxoadipyl-CoA to 3-hydroxyadipyl-CoA, wherein, in the genetically modified microorganism, a dicarboxylic acid excretion carrier function is deleted or decreased.

(2) The genetically modified microorganism according to (1), wherein the deletion or decrease of the dicarboxylic acid excretion carrier function is caused by the deletion or decrease of the function of YjjP or a homolog thereof and/or YjjB or a homolog thereof.

(3) The genetically modified microorganism according to (2), wherein a yjjP gene or a homolog gene thereof and/or a yjjB gene or a homolog gene thereof is/are destroyed or deleted.

(4) The genetically modified microorganism according to (1), wherein the deletion or decrease of the dicarboxylic acid excretion carrier function is caused by the deletion or decrease of the function of YeeA or a homolog thereof and/or YnfM or a homolog thereof.

(5) The genetically modified microorganism according to (4), wherein a yeeA gene or a homolog gene thereof and/or a ynfM gene or a homolog gene thereof is/are destroyed or deleted.

(6) The genetically modified microorganism according to any one of (1) to (5), wherein the microorganism belongs to the genus *Escherichia* or *Serratia*.

(7) The genetically modified microorganism according to any one of (1) to (6), wherein, in the genetically modified microorganism, a gene encoding an enzyme that catalyzes a reaction to reduce 3-oxoadipyl-CoA to 3-hydroxyadipyl-CoA is introduced.

(8) A method of producing 3-hydroxyadipic acid and/or α-hydromuconic acid, comprising culturing the genetically modified microorganism according to any one of (1) to (7).

Effects of the Invention

The genetically modified microorganism can produce 3-hydroxyadipic acid and/or α-hydromuconic acid with a higher yield than a microorganism of the parent strain in which the dicarboxylic acid excretion carrier gene is not modified.

MODE FOR CARRYING OUT THE INVENTION

Below in the specification, 3-hydroxyadipic acid may be abbreviated as 3HA, and α-hydromuconic acid may be abbreviated as HMA. Additionally, 3-oxoadipyl-CoA may be abbreviated as 3OA-CoA, 3-hydroxyadipyl-CoA may be abbreviated as 3HA-CoA, and 2,3-dehydroadipyl-CoA may be abbreviated as HMA-CoA. An enzyme that catalyzes a reaction to reduce 3-oxoadipyl-CoA to 3-hydroxyadipyl-CoA may be hereinafter referred to as "3-oxoadipyl-CoA reductase". An operon formed by the yjjP and yjjB genes in the presence of a single promoter may be referred to as yjjPB. The proteins encoded by the yjjP and yjjB genes may be referred to as YjjP and YjjB respectively, and a complex of these may be referred to as YjjPB. The protein encoded by the yeeA gene may be referred to as YeeA, and the protein encoded by the ynfM gene may be referred to as YnfM.

The microorganism according to the present invention has a gene modified so that the dicarboxylic acid excretion carrier function is deleted or decreased. Making the dicarboxylic acid excretion carrier function be deleted or decreased means making the dicarboxylic acid excretion activity be deleted or decreased. The method of making the function be deleted or decreased is not limited, and can be performed by destroying or deleting the dicarboxylic acid excretion carrier gene, for example, through the following: using a gene mutation agent, ultraviolet radiation, or the like to perform a gene mutation treatment on the nucleotide sequence of the gene or a homolog gene thereof (hereinafter, these are collectively referred to as a "dicarboxylic acid excretion carrier gene") or the nucleotide sequence of the promoter or terminator region of the gene; performing a site-specific mutagenesis method or the like to delete part or all of the nucleotide sequence; introducing a frameshift mutation into the nucleotide sequence; inserting a stop codon into the nucleotide sequence; or the like. It is also possible to destroy or delete the gene, using a genetic recombination technology to remove all or part of the nucleotide sequence of the dicarboxylic acid excretion gene or the nucleotide sequence of the promoter or terminator region of the gene or to replace the nucleotide sequence with another nucleotide sequence. A method preferable among these is preferably to delete part or all of the nucleotide sequence of the dicarboxylic acid excretion carrier gene.

The dicarboxylic acid excretion carrier gene the function of which is to be deleted or decreased in the present invention can be easily obtained, for example, through performing a BLAST (Basic Local Alignment Search Tool) search on a public database in NCBI (National Center for Biotechnology Information), KEGG (Kyoto Encyclopedia of Genes and Genomes), or the like using the amino acid sequence of a known dicarboxylic acid excretion carrier as a query sequence, and referring to the gene that encodes the applicable sequence. Alternatively, the gene can be obtained by PCR using, as a primer, an oligonucleotide generated on the basis of the nucleotide sequence of a known dicarboxylic acid excretion carrier gene, and using, as a template, the genomic DNA of another organism.

The amino acid sequence identity between a known dicarboxylic acid excretion carrier and the protein of a homolog of the carrier is specifically 50% or more, preferably 70% or more, more preferably 80% or more, still more preferably 90% or more, particularly preferably 95% or more.

In this regard, in the present invention, the term "sequence identity" means a ratio (percentage) of the number of identical amino acid or nucleotide residues relative to the total number of amino acid or nucleotide residues over the overlapping portion of an amino acid sequence alignment (including an amino acid corresponding to the translation start site) or a nucleotide sequence alignment (including the start codon), which is obtained by aligning two amino acid or nucleotide sequences with or without introduction of gaps for an optimal match, and is calculated by the following formula (1). In the formula (1), the length of a shorter sequence being compared is not less than 100 amino acids or not less than 300 bases; in cases where the length of the shorter sequence is less than 100 amino acids or less than 300 bases, the sequence identity is not defined. The sequence identity can be easily investigated using, for example, a default parameter on BLAST. Additionally, the sequence identity can also be determined using a similar function implemented in a software program such as Genetyx.

Sequence identity (%)=the number of matches (without counting the number of gaps)/the length of a shorter sequence (excluding the terminal gaps)×100 (1)

In the present invention, the dicarboxylic acid excretion carrier the function of which is to be deleted or decreased is preferably YjjP or a homolog thereof, YjjB or a homolog thereof, YeeA or a homolog thereof, and/or YnfM or a homolog thereof.

YjjP and YjjB are proteins presumed to be putative succinate exporters, and are specifically, for example, YjP (NCBI Protein ID: NP_418784, SEQ ID NO: 2) from *Escherichia coli* str. K-12 substr. MG1655, YjjB (NCBI Protein ID: NP_418783, SEQ ID NO: 4), a YjjP homolog (SEQ ID NO: 6) from *Serratia grimesii* strain NBRC13537, and a YjjB homolog (SEQ ID NO: 8). Examples of genes that encode these proteins include yjjP (NCBI Gene ID: 948812, SEQ ID NO: 1) from *Escherichia coli* str. K-12 substr. MG1655, and yjjB (NCBI Gene ID: 948811, SEQ ID NO: 3), a yjjP homolog (SEQ ID NO: 5) from *Serratia grimesii* strain NBRC13537, and a yjjB homolog (SEQ ID NO: 7). In this regard, the sequence identity between the amino acid sequences represented by SEQ ID NOs: 2 and 6 is calculated using a function of Genetyx (% Identity Matrix) in accordance with the formula (1), and is found to be 71.1%. The sequence identity between the amino acid sequences represented by SEQ ID NOs: 4 and 8 is calculated and found to be 75.8%.

It is known that YjjP and YjjB that coexist have a dicarboxylic acid excretion activity (Biosci Biotechnol Biochem 2017 September; 81 (9): 1837-1844). In particular, JP 2017-216881 A mentions that modifying a bacterium so that the expression of yjjP and yjjB, which are dicarboxylic acid excretion carrier genes, is increased makes it possible to enhance the ability of the bacterium to produce dicarboxylic acid. The document mentions a $C_4$ succinic acid, a $C_6$ adipic acid, and the like as dicarboxylic acids to be produced. Furthermore, the document mentions that YjjP and YjjB from *Escherichia coli* and *Enterobactr aerogenes* belonging to Enterobacteriaceae actually have a dicarboxylic acid excretion activity. Accordingly, those skilled in the art consider that it is predictable that deleting or decreasing the dicarboxylic acid excretion activity in a microorganism having an ability to produce a $C_6$ dicarboxylic acid leads to decreasing the ability of the microorganism to produce a $C_6$ dicarboxylic acid. However, as demonstrated in EXAMPLES in the specification, deleting the functions of YjjP and YjjB enhances the ability to produce 3-hydroxyadipic acid and/or α-hydromuconic acid that are $C_6$ dicarboxylic acids, and deleting or decreasing the dicarboxylic acid excretion activity in a microorganism having an ability to produce 3-hydroxyadipic acid and/or α-hydromuconic acid makes it possible to enhance the ability to produce 3-hydroxyadipic acid and/or α-hydromuconic acid, contrary to the prediction of those skilled in the art.

YeeA is a protein presumed to be a putative transporter, and specific examples of the protein include YeeA (NCBI Protein ID: NP 416512, SEQ ID NO: 91) from *Escherichia coli* str. K-12 substr. MG1655. Examples of genes that encode these proteins include yeeA (NCBI Gene ID: 946545. SEQ ID NO: 90) from *Escherichia coli* str. K-12 substr. MG1655.

YnfM is a protein presumed to be a putative membrane transport protein, and specific examples of the protein include YnfM (NCBI Protein ID: NP_416113, SEQ ID NO: 93) from *Escherichia coli* str. K-12 substr. MG1655. Examples of genes that encode these proteins include ynfM (NCBI Gene ID: 946138, SEQ ID NO: 92) from *Escherichia coli* str. K-12 substr. MG1655.

It is known that YeeA and YnfM have a dicarboxylic acid excretion activity (*Biosci Biotechnol Biochem* 2017 September; 81 (9): 1837-1844). In particular, JP 2017-216881 A mentions that modifying a bacterium so that the expression of yeeA or ynfM, which are dicarboxylic acid excretion carrier genes, is increased makes it possible to enhance the ability of the bacterium to produce dicarboxylic acid. Additionally, the document mentions a $C_4$ succinic acid, a $C_6$ adipic acid, and the like as dicarboxylic acids to be produced. Furthermore, the document mentions that YeeA and YnfM from *Pantoea ananatis* and *Enterobactr aerogenes* belonging to family Enterobacteriaceae actually have a dicarboxylic acid excretion activity. Accordingly, those skilled in the art consider that it is predictable that deleting or decreasing the dicarboxylic acid excretion activity in a microorganism having an ability to produce a $C_6$ dicarboxylic acid leads to decreasing the ability of the microorganism to produce a $C_6$ dicarboxylic acid. However, as demonstrated in EXAMPLES in the specification, deleting the functions of YeeA and YnfM enhances the ability to produce 3-hydroxyadipic acid and/or α-hydromuconic acid that are $C_6$ dicarboxylic acids, and thus deleting or decreasing the dicarboxylic acid excretion activity in a microorganism having an ability to produce 3-hydroxyadipic acid and/or α-hydromuconic acid makes it possible to enhance the ability to produce 3-hydroxyadipic acid and/or α-hydromuconic acid, contrary to the prediction of those skilled in the art.

A homolog of YjjP, a homolog of YjjB, a homolog of YeeA, or a homolog of YnfM, as a subject the function of which is to be deleted or decreased in the present invention, preferably has a succinic acid excretion activity. The fact that the protein has a succinic acid excretion activity can be confirmed by, for example, verifying that the homolog gene introduced into *Escherichia coli* strain AFP184 (WO 2005/116227) having an ability to produce succinic acid enhances succinic acid productivity.

In the present invention, examples of methods of enhancing the activity of the enzyme (3-oxoadipyl-CoA reductase) that catalyzes a reaction to reduce 3-oxoadipyl-CoA to 3-hydroxyadipyl-CoA include: a method in which the genes encoding the enzymes are introduced into a host microorganism; a method in which the number of copies of each of the genes is increased; a method in which the promoter region upstream of the coding region and the ribosome-binding sequence are modified in each of the genes; and the like. These methods may be carried out individually or in combination. The method of introducing a gene is not limited to a particular method, and examples of the method that can be used include a method in which the gene incorporated in an expression vector capable of autonomous replication in a microorganism is introduced into a host microorganism, and a method in which the gene is integrated into the genome of a microorganism.

One or more genes may be introduced. Moreover, introduction of a gene and enhancement of the expression of the gene may be combined.

When a gene encoding an enzyme to be expressed in the present invention is integrated into an expression vector or the genome of a host microorganism, the nucleic acid to be integrated into the expression vector or the genome is preferably composed of a promoter, a ribosome-binding sequence, the coding region of the gene, and a transcription termination sequence, and may additionally contain a gene that controls the activity of the promoter.

The promoter used in the present invention is not limited to a particular promoter, provided that the promoter drives expression of the enzyme in the host microorganism; examples of the promoter include gap promoter, trp promoter, lac promoter, tac promoter, and T7 promoter.

In the present invention, the expression vector to be used to introduce a gene and enhance the expression of a gene is not limited to a particular vector, provided that the vector is capable of autonomous replication in the microorganism; examples of the vector include pBBR1MCS vector, pBR322 vector, pMW vector, pET vector, pRSF vector, pCDF vector, pACYC vector, and derivatives of the above vectors.

In cases where a nucleic acid for genome integration is used in the present invention to introduce a gene or to enhance the expression of a gene, the nucleic acid for genome integration can be introduced by site-specific homologous recombination. The method for site-specific homologous recombination is not limited to a particular method, and examples of the method include a method in which a Red recombinase and FLP recombinase are used (*Proc Natl Acad Sci USA*. 2000 Jun. 6; 97 (12): 6640-6645.), and a method in which λ Red recombinase and the sacB gene are used (*Biosci Biotechnol Biochem*. 2007 December; 71 (12):2905-1.).

The method of introducing the expression vector or the nucleic acid for genome integration is not limited to a particular method, provided that the method is for introduction of a nucleic acid into a microorganism; examples of the method include the calcium ion method (*Journal of Molecular Biology,* 53, 159 (1970)), and electroporation (N M Calvin, P C Hanawalt. *J. Bacteriol,* 170 (1988), pp. 2796-2801).

The reaction scheme 1 below shows an exemplary reaction pathway required for the production of 3-hydroxyadipic acid and/or α-hydromuconic acid. In this scheme, the reaction A represents a reaction that generates 3-oxoadipyl-CoA and coenzyme A from acetyl-CoA and succinyl-CoA. The reaction B represents a reaction that reduces 3-oxoadipyl-CoA to 3-hydroxyadipyl-CoA. The reaction C represents a reaction that generates 2,3-dehydroadipyl-CoA from 3-hydroxyadipyl-CoA. The reaction D represents a reaction that generates 3-hydroxyadipic acid from 3-hydroxyadipyl-CoA. The reaction E represents a reaction that generates α-hydromuconic acid from 2,3-dehydroadipyl-CoA.

[Chem 1]
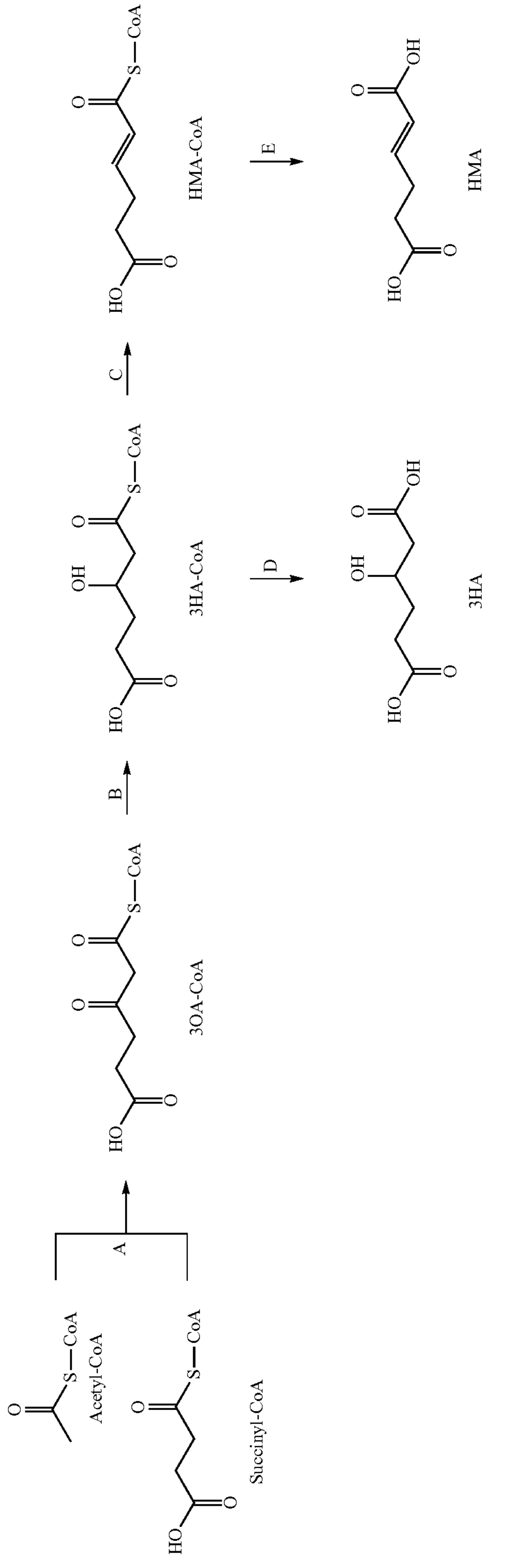
Acetyl-CoA
Succinyl-CoA
3OA-CoA
3HA-CoA
HMA-CoA
3HA
HMA

It is known that in cases where a microorganism has an ability to produce 3-hydroxyadipic acid and/or α-hydromuconic acid, the microorganism has an enzyme that catalyzes at least the reaction A in the biosynthesis pathway represented by the reaction scheme 1, (WO 2019/107516, JP 2013-535203 A, and US 2011/0,124,911 A1).

A reaction that generates 3-hydroxyadipic acid and α-hydromuconic acid from 3-oxoadipylCoA preferably has the biosynthesis pathway represented by the reaction scheme 1. That is, in cases where a genetically modified microorganism according to the present invention has an ability to produce 3-hydroxyadipic acid, a host microorganism for the genetically modified microorganism preferably has an ability to generate 3-oxoadipyl-CoA and coenzyme A from acetyl-CoA and succinyl-CoA (the reaction A), an ability to reduce 3-oxoadipyl-CoA to 3-hydroxyadipyl-CoA (the reaction B), and an ability to generate 3-hydroxyadipic acid from 3-hydroxyadipyl-CoA (the reaction D). In cases where a genetically modified microorganism according to the present invention has an ability to produce α-hydromuconic acid, a host microorganism for the genetically modified microorganism preferably has an ability to generate 3-oxoadipyl-CoA and coenzyme A from acetyl-CoA and succinyl-CoA (the reaction A), an ability to reduce 3-oxoadipyl-CoA to 3-hydroxyadipyl-CoA (the reaction B), an ability to generate 2,3-dehydroadipyl-CoA from 3-hydroxyadipyl-CoA (the reaction C), and an ability to generate α-hydromuconic acid from 2,3-dehydroadipyl-CoA (the reaction E).

A genetically modified microorganism that abundantly produces 3-hydroxyadipic acid and/or α-hydromuconic acid can be obtained using, as a host microorganism, a microorganism having the above-mentioned biosynthesis pathway, in which microorganism, the function(s) of YjjP or a homolog thereof, YjjB or a homolog thereof, YeeA or a homolog thereof, and/or YnfM or a homolog thereof is/are deleted or decreased, and additionally, an enzymatic activity that catalyzes a reaction to reduce 3-oxoadipyl-CoA to 3-hydroxyadipyl-CoA is enhanced.

Examples of microorganisms originally having an ability to produce 3-hydroxyadipic acid include the following microorganisms.

The genus *Escherichia* such as *Escherichia fergusonii* or *Escherichia coli.*

The genus *Serratia* such as *Serratia grimesii, Serratia ficaria, Serratia fonticola, Serratia odorifera, Serratia plymuthica, Serratia entomophila*, or *Serratia nematodiphila.*

The genus *Psuedomonas* such as *Pseudomonas chlororaphis, Pseudomonas putida, Pseudomonas azotoformans*, or *Pseudomonas chlororaphis* subsp. *aureofaciens.*

The genus *Hafnia* such as *Hafnia alvei.*

The genus *Corynebacterium* such as *Corynebacterium acetoacidophilum, Corynebacterium acetoglutamicum, Corynebacterium ammoniagenes*, or *Corynebacterium glutamicum.*

The genus *Bacillus* such as *Bacillus badius, Bacillus magaterium*, or *Bacillus roseus.*

The genus *Streptomyces* such as *Streptomyces vinaceus, Streptomyces karnatakensis*, or *Streptomyces olivaceus.*

The genus *Cupriavidus* such *Cupriavidus metallidurans, Cupriavidus necator*, or *Cupriavidus oxalaticus.*

The genus *Acinetobacter* such as *Acinetobacter baylyi* or *Acinetobacter radioresistens.*

The genus *Alcaligenes* such as *Alcaligenes faecalis.*

The genus *Nocardioides* such as *Nocardioides albus.*

The genus *Brevibacterium* such as *Brevibacterium iodinum.*

The genus *Delftia* such as *Delftia acidovorans.*

The genus *Shimwellia* such as *Shimwellia blattae.*

The genus *Aerobacter* such as *Aerobacter cloacae.*

The genus *Rhizobium* such as *Rhizobium radiobacter.*

Among these microorganisms originally having an ability to produce 3-hydroxyadipic acid, microorganisms belonging to the genus *Escherichia* or *Serratia* are preferably used in the present invention.

Examples of microorganisms presumed to originally have an ability to produce α-hydromuconic acid include the following microorganisms:

The genus *Escherichia* such as *Escherichia fergusonii* or *Escherichia coli.*

The genus *Serratia* such as *Serratia grimesii, Serratia ficaria, Serratia fonticola, Serratia odorifera, Serratia plymuthica, Serratia entomophila*, or *Serratia nematodiphila.*

The genus *Pseudomonas* such as *Pseudomonas fluorescens, Pseudomonas putida, Pseudomonas azotoformans*, or *Pseudomonas chlororaphis* subsp. *aureofaciens.*

The genus *Hafnia* such as *Hafnia alvei.*

The genus *Bacillus* such as *Bacillus badius.*

The genus *Cupriavidus* such *Cupriavidus metallidurans, Cupriavidus numazuensis*, or *Cupriavidus oxalaticus.*

The genus *Acinetobacter* such as *Acinetobacter baylyi* or *Acinetobacter radioresistens.*

The genus *Alcaligenes* such as *Alcaligenes faecalis.*

The genus *Delftia* such as *Delftia acidovorans.*

The genus *Shimwellia* such as *Shimwellia blattae.*

Among these microorganisms originally having an ability to produce α-hydromuconic acid, microorganisms belonging to the genus *Escherichia* or *Serratia* are preferably used in the present invention.

In cases where a genetically modified microorganism according to the present invention originally does not have an ability to produce 3-hydroxyadipic acid, introducing, into a microorganism, a suitable combination of nucleic acids encoding enzymes that catalyze the reactions A, B, and D makes it possible to afford the ability to produce the acid. In cases where a genetically modified microorganism according to the present invention originally does not have an ability to produce α-hydromuconic acid, introducing, into the microorganism, a suitable combination of nucleic acids encoding enzymes that catalyze the reactions A, B, C, and E makes it possible to afford the ability to generate the acid.

In the present invention, a microorganism that can be used as a host to obtain a genetically modified microorganism is not limited to any particular microorganism provided that the microorganism allows genetic modification. The microorganism is preferably a microorganism belonging to the genus *Escherichia, Serratia, Hafnia, Pseudomonas, Corynebacterium, Bacillus, Streptomyces, Cupriavidus, Acinetobacter, Alcaligenes, Brevibacterium, Delftia, Shimwellia, Aerobacter, Rhizobium, Thermobifida, Clostridium, Schizosaccharomyces, Kluyveromyces, Pichia*, or *Candida*, more preferably a microorganism belonging to the genus *Escherichia, Serratia, Hafnia*, or *Pseudomonas*, particularly preferably a microorganism belonging to the genus *Escherichia* or *Serratia.*

Specific examples of the enzymes that catalyze the reaction B to reduce 3-oxoadipyl-CoA to 3-hydroxyadipyl-CoA include the polypeptides described in the following (a) to (c):

(a) a polypeptide composed of an amino acid sequence represented by any one of SEQ ID NOs: 10, 12, 14, 16, 18, 20, and 22;

(b) a polypeptide composed of the same amino acid sequence as that represented by any one of SEQ ID NOs: 10, 12, 14, 16, 18, 20, and 22, except that one or several amino acids are substituted, deleted, inserted, and/or added, and having an enzymatic activity that catalyzes the reaction to reduce 3-oxoadipyl-CoA to 3-hydroxyadipyl-CoA; and (c) a polypeptide composed of an amino acid sequence with a sequence identity of not less than 70% to the sequence represented by any one of SEQ ID NOs: 10, 12, 14, 16, 18, 20, and 22 and having an activity to reduce 3-oxoadipyl-CoA to 3-hydroxyadipyl-CoA.

Furthermore, an enzyme classified as 3-hydroxyacyl-CoA dehydrogenase into EC1.1.1.35 and an enzyme classified as 3-hydroxybutyryl-CoA dehydrogenase into EC1.1.1.157 can also be used as an enzyme having a 3-oxoadipyl-CoA reductase activity. Specific examples of enzymes that catalyze a reaction to reduce 3-oxoadipyl-CoA to 3-hydroxyadipyl-CoA include PaaH (NCBI Protein ID: NP_745425.1) from *Pseudomonas putida* strain KT2440, PaaH (NCBI Protein ID: NP_415913.1) from *Escherichia coli* str. K-12 substr. MG1655, DcaH (NCBI Protein ID: CAG68533.1) from *Acinetobacter baylyi* strain ADP1, PaaH (NCBI Protein ID: WP_063197120) from *Serratia plymuthica* strain NBRC102599, and polypeptide (NCBI Protein ID: WP_033633399.1) from *Serratia nematodiphila* strain DSM21420. Among these, the polypeptides described in (a) to (c) above are preferable.

For the polypeptide used in the present invention and composed of the same amino acid sequence as that represented by any one of SEQ ID NOs: 10, 12, 14, 16, 18, 20, and 22, except that one or several amino acids are substituted, deleted, inserted, and/or added, and having 3-oxoadipyl-CoA reductase activity, the range represented by the phrase "one or several" is preferably 10 or less, more preferably 5 or less, particularly preferably 4 or less, and most preferably one or two. In the case of amino acid substitution, the activity of the original polypeptide is more likely to be maintained when an amino acid(s) is/are replaced by an amino acid(s) with similar properties (so-called conservative substitution). That is, the physiological activity of the original polypeptide is often maintained when the amino acid(s) is/are replaced by an amino acid(s) with similar properties. Thus, the amino acid(s) is/are preferably replaced by an amino acid(s) with similar properties. That is, the 20 amino acids constituting naturally occurring proteins can be divided into groups with similar properties, such as neutral amino acids with a less polar side chain (Gly, Ile, Val, Leu, Ala, Met, Pro), neutral amino acids with a hydrophilic side chain (Asn, Gln, Thr, Ser, Tyr, Cys), acidic amino acids (Asp, Glu), basic amino acids (Arg, Lys, His), and aromatic amino acids (Phe, Tyr, Trp); it is often the case that substitution between amino acids in the same group does not change the properties of the original polypeptide.

For the polypeptide used in the present invention and having an amino acid sequence with a sequence identity of not less than 70% to the sequence represented by any one of SEQ ID NOs: 10, 12, 14, 16, 18, 20, and 22 and having 3-oxoadipyl-CoA reductase activity, the sequence identity is preferably not less than 80%, more preferably not less than 85%, further preferably not less than 90%, still further preferably not less than 95%, yet further preferably not less than 97%, and even further preferably not less than 99%.

All the polypeptides represented by SEQ ID NOs: 10, 12, 14, 16, 18, 20, and 22 as described above in (a) contain a common sequence 1, composed of 24 amino acid residues and represented by SEQ ID NO: 23, within a region from the 15th to the 38th amino acid residues from the N terminus (hereinafter, an amino acid residue at the n-th position from the N terminus may conveniently be represented by n "a.a."; for example, the region from the 15th to the 38th amino acid residues from the N terminus may be thus simply represented by "15 to 38 a.a."). In the common sequence 1, Xaa represents an arbitrary amino acid residue; the 13 a.a. is preferably a phenylalanine or leucine residue; the 15 a.a. is preferably a leucine or glutamine residue; the 16 a.a. is preferably a lysine or asparagine residue; the 17 a.a. is a glycine or serine residue, more preferably glycine residue; the 19 a.a. is preferably a proline or arginine residue, and the 21 a.a. is preferably a leucine, methionine, or valine residue. The common sequence 1 corresponds to the region of the NAD+-binding residue and the surrounding amino acid residues. In the NAD+-binding residues, the 24th amino acid residue in the common sequence 1 is aspartic acid, as described in *Biochimie.* 2012 February; 94 (2): 471-8., but in the common sequence 1, the residue is asparagine, which is characteristic. It is thought that the polypeptides represented by SEQ ID NOs: 10, 12, 14, 16, 18, 20, and 22 exhibit excellent enzymatic activity as 3-oxoadipyl-CoA reductases due to the presence of the common sequence 1.

The polypeptides as described above in (b) and (c) also preferably contain the common sequence 1, composed of 24 amino acid residues and represented by SEQ ID NO: 23, within a region from 1 to 200 a.a. The common sequence is more preferably contained within a region from 1 to 150 a.a., further preferably from 1 to 100 a.a.

The nucleic acids encoding the polypeptides described in (a) to (c) according to the present invention may contain an additional sequence that encodes a peptide or protein added to the original polypeptides at the N terminus and/or the C terminus. Examples of such a peptide or protein can include secretory signal sequences, transport proteins, binding proteins, tag peptides applicable for purification, and fluorescent proteins. Among those peptides or proteins, a peptide or protein with a desired function can be selected depending on the purpose and added to the polypeptides of the present invention by those skilled in the art. It should be noted that the amino acid sequence of such a peptide or protein is not included in the calculation of sequence identity.

The nucleic acids encoding the polypeptides represented by SEQ ID NOs: 10, 12, 14, 16, 18, 20, and 22 are not particularly limited, provided that those nucleic acids are composed of nucleotide sequences which can be translated into the amino acid sequences represented by SEQ ID NOs: 10, 12, 14, 16, 18, 20, and 22, and the nucleotide sequences can be determined by considering a set of codons (standard genetic code) corresponding to each amino acid. In this respect, the nucleotide sequences may be redesigned using codons that are frequently used by a host microorganism used in the present invention.

Specific examples of the nucleotide sequences of the nucleic acids that encode the polypeptides with the amino acid sequences represented by SEQ ID NOs: 10, 12, 14, 16, 18, 20, and 22 include the nucleotide sequences represented by SEQ ID NOs: 9, 11, 13, 15, 17, 19, and 21, respectively.

In the present invention, whether or not a polypeptide encoded by a certain nucleic acid has 3-oxoadipyl-CoA reductase activity is determined as follows: transformant strains A and B described below are produced and grown in a culture test, and if the presence of 3-hydroxyadipic acid or α-hydromuconic acid in the resulting culture fluid is confirmed, it is judged that the nucleic acid encodes a polypeptide having 3-oxoadipyl-CoA reductase activity. The determination method will be described using the reaction scheme 1 above which shows a biosynthesis pathway.

The transformant strain A has enzymes that catalyze the reactions A, D, and E. The transformant strain B has enzymes that catalyze the reactions A, C, D, and E.

The transformant strain A is first produced. Plasmids for the expression of enzymes that catalyze the reactions A, D, and E, respectively, are produced. The reactions D and E can be catalyzed by an identical enzyme. The plasmids are introduced into *Escherichia coli* strain BL21 (DE3), which is a microorganism strain lacking abilities to produce both 3-hydroxyadipic acid and α-hydromuconic acid. An expression plasmid in which a nucleic acid encoding a polypeptide, which is a subject of analysis for the presence of the enzymatic activity of interest, is incorporated downstream of a suitable promoter is introduced to obtain the transformant strain A. The transformant strain A is cultured, and the post-culture fluid is examined for the presence of 3-hydroxyadipic acid. Once the presence of 3-hydroxyadipic acid in the culture fluid is confirmed, the transformant strain B is then produced. The transformant strain B is obtained by introducing a plasmid for the expression of an enzyme that catalyzes the reaction C into the transformant strain A. The transformant strain B is cultured, and the post-culture fluid is examined for the presence of α-hydromuconic acid. When the presence of α-hydromuconic acid in the post-culture fluid is confirmed, it indicates that 3-hydroxyadipic acid produced in the transformant strain A and α-hydromuconic acid produced in the transformant strain B are generated through production of 3-hydroxyadipyl-CoA, and so it is judged that the subject polypeptide has 3-oxoadipyl-CoA reductase activity.

Specific examples of a method that can be used as above-mentioned include a method described in WO 2019/107516.

The 3-oxoadipyl-CoA reductase activity value can be calculated by quantifying 3-hydroxyadipyl-CoA generated from 3-oxoadipyl-CoA used as a substrate by purified 3-oxoadipyl-CoA reductase, wherein the 3-oxoadipyl-CoA is prepared from 3-oxoadipic acid by an enzymatic reaction. The specific method is as follows.

3-Oxoadipic acid can be prepared by a known method (for example, a method described in Reference Example 1 of WO 2017/099209).

Preparation of 3-oxoadipyl-CoA solution: A PCR using the genomic DNA of *Pseudomonas putida* strain KT2440 as a template is performed in accordance with routine procedures, to amplify a nucleic acid encoding a CoA transferase (pcaI and pcaJ; NCBI Gene IDs: 1046613 and 1046612) in the full-length form. The nucleotide sequences of primers used in this PCR are, for example, those represented by SEQ ID NOs: 24 and 25. The amplified fragment is inserted into the KpnI site of pRSF-1b (manufactured by Merck Millipore) which is an expression vector for *E. coli*, in-frame with the histidine-tag sequence. The plasmid is introduced into *E. coli* BL21 (DE3), and expression of the enzyme is induced with isopropyl-β-thiogalactopyranoside (IPTG) in accordance with routine procedures and the enzyme is purified using the histidine tag from the culture fluid to obtain a CoA transferase solution. The solution is used to prepare an enzymatic reaction solution for 3-oxoadipyl-CoA preparation with the following composition, which is allowed to react at 25° C. for 3 minutes and then filtered through a UF membrane (Amicon Ultra-0.5 mL 10K; manufactured by Merck Millipore) to remove the enzyme, and the obtained filtrate is designated as 3-oxoadipyl-CoA solution.

(Enzymatic Reaction Solution)

100 mM Tris-HCl (pH 8.2)
10 mM $MgCl_2$
0.5 mM succinyl-CoA
5 mM 3-oxoadipic acid sodium salt
2 μM CoA transferase.

Identification of 3-oxoadipyl-CoA reductase activity: A PCR using the genomic DNA of a subject microorganism strain as a template is performed in accordance with routine procedures, to amplify a nucleic acid encoding 3-oxoadipyl-CoA reductase in the full-length form. The amplified fragment is inserted into the BamHI site of pACYCDuet-1 (manufactured by Merck Millipore) which is an expression vector for *E. coli*, in-frame with the histidine-tag sequence. The plasmid is introduced into *E. coli* BL21 (DE3), and expression of the enzyme is induced with isopropyl-β-thiogalactopyranoside (IPTG) in accordance with routine procedures and the enzyme is purified using the histidine tag from the culture fluid to obtain a 3-oxoadipyl-CoA reductase solution. The 3-oxoadipyl-CoA reductase activity can be determined by using the enzyme solution to prepare an enzymatic reaction solution with the following composition and quantifying 3-hydroxyadipyl-CoA generated at 25° C.

(Enzymatic Reaction Solution)

100 mM Tris-HCl (pH 8.2)
10 mM $MgCl_2$
150 μL/mL 3-oxoadipyl-CoA solution
0.5 mM NADH
1 mM dithiothreitol
10 μM 3-oxoadipyl-CoA reductase.

Next, specific examples of the enzymes that catalyze the reactions A and C to E are presented. As an enzyme that catalyzes the reaction A to generate 3-oxoadipyl-CoA, for example, an acyl transferase (β-ketothiolase) can be used. The acyl transferase is not limited by a particular number in the EC classification, and is preferably an acyl transferase classified into EC 2.3.1.-, specifically including an enzyme classified as 3-oxoadipyl-CoA thiolase and classified into EC 2.3.1.174, an enzyme classified as acetyl-CoA C-acetyltransferase and classified into EC 2.3.1.9, and an enzyme classified as acetyl-CoA C-acyl transferase and classified into EC 2.3.1.16. Among them, PaaJ from *Escherichia coli* str. K-12 substr. MG1655 (NCBI Protein ID: NP_415915), PcaF from *Pseudomonas putida* strain KT2440 (NCBI Protein ID: NP_743536), and the like can be suitably used.

Whether or not the above acyl transferases can generate 3-oxoadipyl-CoA from succinyl-CoA and acetyl-CoA used as substrates can be determined by measuring a decrease in NADH coupled with reduction of 3-oxoadipyl-CoA in a combination of the reaction to generate 3-oxoadipyl-CoA by purified acyl transferase and the reaction to reduce 3-oxoadipyl-CoA used as a substrate by purified 3-oxoadipyl-CoA reductase. The specific measurement method is, for example, as follows.

Identification of acyl transferase activity: A PCR using the genomic DNA of a subject microorganism strain as a template is performed in accordance with routine procedures, to amplify a nucleic acid encoding an acyl transferase in the full-length form. The amplified fragment is inserted into the SacI site of pACYCDuet-1 (manufactured by Merck Millipore) which is an expression vector for *E. coli*, in-frame with the histidine-tag sequence. The plasmid is introduced into *E. coli* BL21 (DE3), and expression of the enzyme is induced with isopropyl-β-thiogalactopyranoside (IPTG) in accordance with routine procedures and the enzyme is purified using the histidine tag from the culture fluid to obtain an acyl transferase solution. The acyl transferase activity can be determined by using the enzyme solution to prepare an enzymatic reaction solution with the following composition and measuring a decrease in absorbance at 340 nm coupled with oxidation of NADH at 30° C.

100 mM Tris-HCl (pH 8.0)
10 mM $MgCl_2$
0.1 mM succinyl-CoA
0.2 mM acetyl-CoA
0.2 mM NADH
1 mM dithiothreitol
10 μg/mL 3-oxoadipyl-CoA reductase
5 μg/mL acyltransferase.

Whether an enzyme possessed by a microorganism has acyl transferase activity can be determined by performing the above-described measurement using CFE instead of purified acyl transferase. The specific measurement method targeted to *E. coli* is, for example, as follows.

Preparation of CFE: A loopful of *E. coli* strain MG1655 to be subjected to the measurement of the activity is inoculated into 5 mL of a culture medium (culture medium composition: 10 g/L tryptone, 5 g/L yeast extract, 5 g/L sodium chloride) adjusted to pH 7, and incubated at 30° C. with shaking for 18 hours. The obtained culture fluid is added to 5 mL of a culture medium (culture medium composition: 10 g/L tryptone, 5 g/L yeast extract, 5 g/L sodium chloride, 2.5 mM ferulic acid, 2.5 mM p-coumaric acid, 2.5 mM benzoic acid, 2.5 mM cis,cis-muconic acid, 2.5 mM protocatechuic acid, 2.5 mM catechol, 2.5 mM 3OA, 2.5 mM 3-hydroxyadipic acid, 2.5 mM α-hydromuconic acid, 2.5 mM adipic acid, 2.5 mM phenylethylamine) adjusted to pH 7, and incubated at 30° C. with shaking for 3 hours.

The obtained culture fluid is supplemented with 10 mL of 0.9% sodium chloride and then centrifuged to remove the supernatant from bacterial cells, and this operation is repeated three times in total to wash the bacterial cells. The washed bacterial cells are suspended in 1 mL of a Tris-HCl buffer consisting of 100 mM Tris-HCl (pH 8.0) and 1 mM dithiothreitol, and glass beads (with a diameter of 0.1 mm) are added to the resulting suspension to disrupt the bacterial cells at 4° C. with an ultrasonic disruptor. The resulting bacterial homogenate is centrifuged to obtain the supernatant, and 0.5 mL of the supernatant is filtered through a UF membrane (Amicon Ultra-0.5 mL 10K; manufactured by Merck Millipore) to remove the resulting filtrate, followed by application of 0.4 mL of the Tris-HCl buffer to the UF membrane, and this operation is repeated three times in total to remove low-molecular-weight impurities, and the resulting supernatant is then resuspended in the Tris-HCl buffer to a final volume of 0.1 mL, which is designated as CFE. Instead of purified enzyme, 0.05 mL of the CFE is added to a total of 0.1 mL of the enzymatic reaction solution to determine the enzymatic activity.

As an enzyme that catalyzes the reaction C to generate 2,3-dehydroadipyl-CoA, for example, an enoyl-CoA hydratase can be used. The enoyl-CoA hydratase is not limited by a particular number in the EC classification, and is preferably an enoyl-CoA hydratase classified into EC 4.2.1.-, specifically including an enzyme classified as enoyl-CoA hydratase or 2,3-dehydroadipyl-CoA hydratase and classified into EC 4.2.1.17. Among them, PaaF (NCBI Protein ID: NP_415911) from *Escherichia coli* str. K-12 substr. MG1655, PaaF (NCBI Protein ID: NP_745427) from *Pseudomonas putida* strain KT2440, and the like can be suitably used.

Since the reaction catalyzed by enoyl-CoA hydratase is generally reversible, whether or not an enoyl-CoA hydratase has an activity to catalyze a reaction that generates 2,3-dehydroadipyl-CoA from 3-hydroxyadipyl-CoA used as a substrate can be determined by detecting 3-hydroxyadipyl-CoA generated using purified enoyl-CoA hydratase with 2,3-dehydroadipyl-CoA used as a substrate thereof, which is prepared from α-hydromuconic acid through an enzymatic reaction. The specific measurement method is, for example, as follows.

Preparation of α-hydromuconic acid: Preparation of α-hydromuconic acid can be performed according to the method described in Reference Example 1 of WO 2016/199858.

Preparation of 2,3-dehydroadipyl-CoA solution: A PCR using the genomic DNA of *Pseudomonas putida* strain KT2440 as a template is performed in accordance with routine procedures, to amplify a nucleic acid encoding a CoA transferase (including pcaI and pcaJ; NCBI Gene IDs: 1046613 and 1046612) in the full-length form. The nucleotide sequences of primers used in this PCR are, for example, those represented by SEQ ID NOs: 24 and 25. The amplified fragment is inserted into the KpnI site of pRSF-1b (manufactured by Merck Millipore) which is an expression vector for *E. coli*, in-frame with the histidine-tag sequence. The plasmid is introduced into *E. coli* BL21 (DE3), and expression of the enzyme is induced with isopropyl-β-thiogalactopyranoside (IPTG) in accordance with routine procedures and the enzyme is purified using the histidine tag from the culture fluid to obtain a CoA transferase solution. The solution is used to prepare an enzymatic reaction solution for 2,3-dehydroadipyl-CoA preparation with the following composition, which is allowed to react at 30° C. for 10 minutes and then filtered through a UF membrane (Amicon Ultra-0.5 mL 10K; manufactured by Merck Millipore) to remove the enzyme, and the obtained filtrate is designated as 2,3-dehydroadipyl-CoA solution.

Enzymatic Reaction Solution for 2,3-Dehydroadipyl-CoA Preparation 100 mM Tris-HCl (pH 8.0)
10 mM $MgCl_2$
0.4 mM succinyl-CoA
2 mM α-hydromuconic acid sodium salt
20 μg/mL CoA transferase.

Identification of enoyl-CoA hydratase activity: A PCR using the genomic DNA of a subject microorganism strain as a template is performed in accordance with routine procedures, to amplify a nucleic acid encoding an enoyl-CoA hydratase in the full-length form. The amplified fragment is inserted into the NdeI site of pET-16b (manufactured by Merck Millipore) which is an expression vector for *E. coli*, in-frame with the histidine-tag sequence. The plasmid is introduced into *E. coli* BL21 (DE3), and expression of the enzyme is induced with isopropyl-β-thiogalactopyranoside (IPTG) in accordance with routine procedures and the enzyme is purified using the histidine tag from the culture fluid to obtain an enoyl-CoA hydratase solution. The solution is used to prepare an enzymatic reaction solution with the following composition, which is allowed to react at 30° C. for 10 minutes and then filtered through a UF membrane (Amicon Ultra-0.5 mL 10K; manufactured by Merck Millipore) to remove the enzyme. The enoyl-CoA hydratase activity can be confirmed by detecting 3-hydroxyadipyl-CoA in the resulting filtrate on high-performance liquid chromatograph-tandem mass spectrometer (LC-MS/MS) (Agilent Technologies, Inc.).

100 mM Tris-HCl (pH 8.0)
10 mM $MgCl_2$
300 μL/mL 2,3-dehydroadipyl-CoA solution
1 mM dithiothreitol
20 μg/mL enoyl-CoA hydratase.

Whether or not an enzyme originally expressed in a host microorganism used in the present invention has enoyl-CoA hydratase activity can be determined by adding 0.05 ml, of the CFE, instead of purified enoyl-CoA hydratase, to a total of 0.1 mL of the enzymatic reaction solution and performing the above-described measurement. The specific CFE preparation method targeted to *E. coli* is as described for that used in determination of acyl transferase activity.

As an enzyme that catalyzes the reaction D to generate 3-hydroxyadipic acid and the reaction E to generate α-hydromuconic acid, for example, a CoA transferase or an acyl-CoA hydrolase, preferably a CoA transferase, can be used.

The CoA transferase is not limited by a particular number in the EC classification, and is preferably a CoA transferase classified into EC 2.8.3.-, specifically including an enzyme classified as CoA transferase or acyl-CoA transferase and classified into EC 2.8.3.6, and the like.

In the present invention, the term "CoA transferase" refers to an enzyme with activity (CoA transferase activity) to catalyze a reaction that generates carboxylic acid and succinyl-CoA from acyl-CoA and succinic acid used as substrates.

As an enzyme that catalyzes the reaction D to generate 3-hydroxyadipic acid and the reaction E to generate α-hydromuconic acid, PcaI and PcaJ from *Pseudomonas putida* strain KT2440 (NCBI Protein IDs: NP_746081 and NP_746082), and the like can be suitably used, among others.

Since the above enzymatic reactions are reversible, the CoA transferase activity against 3-hydroxyadipyl-CoA or 2,3-dehydroadipyl-CoA used as a substrate can be determined by detecting 3-hydroxyadipyl-CoA and 2,3-dehydroadipyl-CoA generated respectively using purified CoA transferase with 3-hydroxyadipic acid and succinyl-CoA, or α-hydromuconic acid and succinyl-CoA, used as substrates thereof. The specific measurement method is, for example, as follows.

Preparation of 3-hydroxyadipic acid: Preparation of 3-hydroxyadipic acid is performed according to the method described in Reference Example 1 of WO 2016/199856 A1.

Identification of CoA transferase activity using 3-hydroxyadipic acid as a substrate: A PCR using the genomic DNA of a subject microorganism strain as a template is performed in accordance with routine procedures, to amplify a nucleic acid encoding a CoA transferase in the full-length form. The amplified fragment is inserted into the KpnI site of pRSF-1 b (manufactured by Merck Millipore) which is an expression vector for *E. coli*, in-frame with the histidine-tag sequence. The plasmid is introduced into *E. coli* BL21 (DE3), and expression of the enzyme is induced with isopropyl-β-thiogalactopyranoside (IPTG) in accordance with routine procedures and the enzyme is purified using the histidine tag from the culture fluid to obtain a CoA transferase solution. The solution is used to prepare an enzymatic reaction solution with the following composition, which is allowed to react at 30° C. for 10 minutes and then filtered through a UF membrane (Amicon Ultra-0.5 mL 10K; manufactured by Merck Millipore) to remove the enzyme. The CoA transferase activity can be confirmed by detecting 3-hydroxyadipyl-CoA in the resulting filtrate on high-performance liquid chromatograph-tandem mass spectrometer (LC-MS/MS) (Agilent Technologies, Inc.).

100 mM Tris-HCl (pH 8.0)
10 mM $MgCl_2$
0.4 mM succinyl-CoA
2 mM 3-hydroxyadipic acid sodium salt
20 μg/mL CoA transferase.

Preparation of α-hydromuconic acid: Preparation of α-hydromuconic acid can be performed according to a method described in Reference Example 1 of WO 2016/199858.

Identification of CoA transferase activity using α-hydromuconic acid as a substrate: A PCR using the genomic DNA of a subject microorganism strain as a template is performed in accordance with routine procedures, to amplify a nucleic acid encoding a CoA transferase in the full-length form. The amplified fragment is inserted into the KpnI site of pRSF-1b (manufactured by Merck Millipore) which is an expression vector for *E. coli*, in-frame with the histidine-tag sequence. The plasmid is introduced into *E. coli* BL21 (DE3), and expression of the enzyme is induced with isopropyl-β-thiogalactopyranoside (IPTG) in accordance with routine procedures and the enzyme is purified using the histidine tag from the culture fluid to obtain a CoA transferase solution. The solution is used to prepare an enzymatic reaction solution with the following composition, which is allowed to react at 30° C. for 10 minutes and then filtered through a UF membrane (Amicon Ultra-0.5 mL 10K; manufactured by Merck Millipore) to remove the enzyme. The CoA transferase activity can be confirmed by detecting 2,3-dehydroadipyl-CoA in the resulting filtrate on high-performance liquid chromatograph-tandem mass spectrometer (LC-MS/MS) (Agilent Technologies, Inc.).

100 mM Tris-HCl (pH 8.0)
10 mM $MgCl_2$
0.4 mM succinyl-CoA
2 mM α-hydromuconic acid sodium salt
20 μg/mL CoA transferase.

Whether or not an enzyme originally expressed in a host microorganism used in the present invention has CoA transferase activity can be determined by adding 0.05 mL of the CFE, instead of purified CoA transferase, to a total of 0.1 mL of the enzymatic reaction solution and performing the above-described measurement. The specific CFE preparation method targeted to *E. coli* is as described for that used in determination of acyl transferase activity.

When a nucleic acid encoding any one selected from the acyl transferase, the 3-oxoadipyl-CoA reductase, the enoyl-CoA hydratase, and the CoA transferase is introduced into a host microorganism in the present invention, the nucleic acid may be artificially synthesized based on the amino acid sequence information of the enzyme in a database, or isolated from the natural environment. In cases where the nucleic acid is artificially synthesized, the usage frequency of codons corresponding to each amino acid in the nucleic acid sequence may be changed depending on the host microorganism into which the nucleic acid is introduced.

In cases where the nucleic acids encoding the enzymes are isolated from the natural environment, the organisms as sources of the genes are not limited to particular organisms, and examples of the organisms include those of the genus *Acinetobacter*, such as *Acinetobacter baylyi* and *Acinetobacter radioresistens*; the genus *Aerobacter*, such as *Aerobacter cloacae*; the genus *Alcaligenes*, such as *Alcaligenes faecalis*; the genus *Bacillus*, such as *Bacillus badius, Bacillus magaterium*, and *Bacillus roseus*; the genus *Brevibacterium*, such as *Brevibacterium iodinum*; the genus *Corynebacterium*, such as *Corynebacterium acetoacidophilum, Corynebacterium acetoglutamicum, Corynebacterium ammoniagenes*, and *Corynebacterium glutamicum*; the genus *Cupriavidus*, such as *Cupriavidus metallidurans, Cupriavidus necator, Cupriavidus numazuensis*, and *Cupriavidus oxalaticus*; the genus *Delftia*, such as *Delftia acidovorans*; the genus *Escherichia*, such as *Escherichia*

*coli* and *Escherichia fergusonii*; the genus *Hafnia*, such as *Hafnia alvei*; the genes *Microbacterium*, such as *Microbacterium ammoniaphilum*; the genus *Nocardioides*, such as *Nocardioides albus*; the genus *Planomicrobium*, such as *Planomicrobium okeanokoites*; the genus *Pseudomonas*, such as *Pseudomonas azotoformans, Pseudomonas chlororaphis, Pseudomonas fluorescens, Pseudomonas fragi, Pseudomonas putida*, and *Pseudomonas reptilivora*; the genus *Rhizobium*, such as *Rhizobium radiobacter*; the genus *Rhodosporidium*, such as *Rhodosporidium toruloides*; the genus *Saccharomyces*, such as *Saccharomyces cerevisiae*; the genus *Serratia*, such as *Serratia entomophila, Serratia ficaria, Serratia fonticola, Serratia grimesii, Serratia nematodiphila, Serratia odorifera*, and *Serratia plymuthica*; the genus *Shimwellia*, such as *Shimwellia blattae*; the genus *Streptomyces*, such as *Streptomyces vinaceus, Streptomyces karnatakensis, Streptomyces olivaceus*, and *Streptomyces vinaceus*; the genus *Yarrowia*, such as *Yarrowia lipolytica*; the genus *Yersinia*, such as *Yersinia ruckeri*; the genus *Euglena*, such as *Euglena gracilis*; and the genus *Thermobifida*, such as *Thermobifida fusca*; preferably those of the genera *Acinetobacter, Corynebacterium, Escherichia, Pseudomonas, Serratia, Euglena*, and *Thermobifida*.

In a microorganism according to the present invention, the function of pyruvate kinase is preferably deleted to enhance the ability to produce 3-hydroxyadipic acid and/or α-hydromuconic acid.

Pyruvate kinase is classified in EC2.7.1.40, and is an enzyme that catalyzes a reaction by which phosphoenolpyruvate is dephosphorylated and converted into pyruvic acid and ATP. Specific examples include PykF (NCBI Protein ID: NP_416191, SEQ ID NO: 27) from *Escherichia coli* str. K-12 substr. MG1655, PykA (NCBI Protein ID: NP_416368, SEQ ID NO: 28), PykF (SEQ ID NO: 30), PykA (SEQ ID NO: 31) from *Serratia grimesii* strain NBRC13537, and the like. In cases where a microorganism used in the present invention has two or more genes encoding pyruvate kinase, all the pyruvate kinase functions are preferably deleted. Whether or not a polypeptide to be encoded by a gene possessed by a microorganism used in the present invention is pyruvate kinase can be checked by performing a BLAST search on the public database in NCBI, KEGG, or the like.

In a microorganism according to the present invention, the activity of phosphoenolpyruvate carboxykinase is preferably enhanced in order to enhance the ability to produce 3-hydroxyadipic acid and/or α-hydromuconic acid.

Phosphoenolpyruvate carboxykinase is classified in EC4.1.1.49, and is an enzyme that catalyzes a reaction to generate oxaloacetic acid and ATP from phosphoenolpyruvate, carbon dioxide, and ADP. Specific examples include Pck (NCBI Protein ID: NP_417862, SEQ ID NO: 32) from *Escherichia coli* str. K-12 substr. MG1655, PckA_1 (SEQ ID NO: 33), PckA_2 (SEQ ID NO: 34) from *Serratia grimesii* strain NBRC13537, and the like.

From a physiological viewpoint, phosphoenolpyruvate carboxykinase serves for the main reaction in the production of glucose from fatty acid in gluconeogenesis. The reaction catalyzed by phosphoenolpyruvate carboxykinase is reversible. In the production of 3-hydroxyadipic acid and/or α-hydromuconic acid, the reaction progresses toward converting phosphoenolpyruvate and carbon dioxide into oxaloacetic acid.

Whether or not a polypeptide to be encoded by an enzyme gene used in the present invention is phosphoenolpyruvate carboxykinase can be checked by performing a BLAST search on a website of NCBI, KEGG, or the like. The genetically modified microorganism according to the present invention is cultured in a culture medium, preferably a liquid culture medium, containing, as a material for fermentation, a carbon source which can be used by ordinary microorganisms. The culture medium used contains, in addition to the carbon source that can be used by the genetically modified microorganism, appropriate amounts of a nitrogen source, inorganic salts, and, if necessary, organic trace nutrients such as amino acids and vitamins. Any of natural and synthetic culture media can be used as long as the medium contains the above-described nutrients.

The material for fermentation is a material that can be metabolized by the genetically modified microorganism. The term "metabolize" refers to conversion of a chemical compound, which a microorganism has taken up from the extracellular environment or intracellularly generated from a different chemical compound, to another chemical compound through an enzymatic reaction. Sugars can be suitably used as the carbon source. Specific examples of the sugars include monosaccharides, such as glucose, fructose, galactose, mannose, xylose, and arabinose; disaccharides such as sucrose, and polysaccharides formed by linking these monosaccharides; and saccharified starch solution, molasses, and saccharified solution from cellulose-containing biomass, each containing any of those saccharides.

The above-listed carbon sources may be used individually or in combination, and the culture is preferably performed in a culture medium containing glucose in particular. When a carbon source is added, the concentration of the carbon source in the culture medium is not particularly limited, and can be appropriately selected depending on the type of the carbon source. The concentration of the glucose is preferably 5 to 300 g/L.

As the nitrogen source used for culturing the genetically modified microorganism, for example, ammonia gas, aqueous ammonia, ammonium salts, urea, nitric acid salts, other supplementarily used organic nitrogen sources, such as oil cakes, soybean hydrolysate, cascin degradation products, other amino acids; vitamins, corn steep liquor, yeast or yeast extract, meat extract, peptides such as peptone, and bacterial cells and hydrolysate of various fermentative bacteria can be used. The concentration of the nitrogen source in the culture medium is not particularly limited, and is preferably from 0.1 g/L to 50 g/L.

As the inorganic salts used for culturing the genetically modified microorganism, for example, phosphoric acid salts, magnesium salts, calcium salts, iron salts, and manganese salts can be appropriately added to the culture medium and used.

The culture conditions for the genetically modified microorganism to produce 3-hydroxyadipic acid and/or α-hydromuconic acid are set by appropriately adjusting or selecting, for example, the culture medium with the above composition, culture temperature, stirring speed, pH, aeration rate, and inoculation amount, depending on, for example, the type of the genetically modified microorganism and external conditions.

The range of pH in a culture is not limited to any particular value provided that such a range makes it possible to grow the genetically modified microorganism, and is preferably a pH range of from 5 to 8, more preferably a pH range of from 5.5 to 6.8.

The range of the aeration condition in a culture is not limited to any particular value provided that such a range makes it possible to produce 3-hydroxyadipic acid and/or α-hydromuconic acid. To grow the microorganism mutant well, it is preferable that oxygen remain in the liquid phase or the gas phase in the culture container at least when the culture is started.

In cases where foam is formed in a liquid culture, an antifoaming agent such as a mineral oil, silicone oil, or surfactant may be appropriately added to the culture medium.

After a recoverable amount of 3-hydroxyadipic acid and/or α-hydromuconic acid is produced during culturing of the microorganism, the produced products can be recovered. The produced products can be recovered, for example isolated, according to a commonly used method, in which the culturing is stopped once a product of interest is accumulated to an appropriate level, and the fermentation product is collected from the culture. Specifically, the products can be isolated from the culture by column chromatography, ion exchange chromatography, activated charcoal treatment, crystallization, membrane separation, distillation or the like after separation of bacterial cells through centrifugation, filtration or the like. More specifically, examples include, but are not limited to, a method in which an acidic component is added to salts of the products, and the resulting precipitate is collected; a method in which water is removed from the culture by concentration using, for example, a reverse osmosis membrane or an evaporator to increase the concentrations of the products and the products and/or salts of the products are then crystallized and precipitated by cooling or adiabatic crystallization to recover the crystals of the products and/or salts of the products by, for example, centrifugation or filtration; and a method in which an alcohol is added to the culture to produce esters of the products and the resulting esters of the products are subsequently collected by distillation and then hydrolyzed to recover the products. These recovery methods can be appropriately selected and optimized depending on, for example, physical properties of the products.

EXAMPLES

The present invention will now be specifically described by way of Examples.

Reference Example 1

Production of a plasmid for expression of an enzyme that catalyzes a reaction to generate 3OA-CoA and coenzyme A from acetyl-CoA and succinyl-CoA (the reaction A) and an enzyme that catalyzes a reaction to generate 3HA-CoA from 3OA-CoA (the reaction B), a reaction to generate 3-hydroxyadipic acid from 3HA-CoA (the reaction D), and a reaction to generate α-hydromuconic acid from HMA-CoA (the reaction E)

The pBBR1MCS-2 vector, which is capable of autonomous replication in *E. coli* (ME Kovach, (1995), Gene 166: 175-176), was cleaved with XhoI to obtain pBBR1MCS-2/XhoI. To integrate a constitutive expression promoter into the vector, primers (SEQ ID NOs: 36 and 37) were designed for use in amplification of an upstream 200-b region (SEQ ID NO: 35) of gapA (NCBI Gene ID: NC_000913.3) by PCR using the genomic DNA of *Escherichia coli* str. K-12 substr. MG1655 as a template, and a PCR reaction was performed in accordance with routine procedures. The resulting fragment and the pBBR1MCS-2/XhoI were ligated together using the "In-Fusion ID Cloning Kit" (manufactured by Takara Bio Inc.), and the resulting plasmid was introduced into *E. coli* strain DH5a. The nucleotide sequence on the plasmid extracted from the obtained recombinant *E. coli* strain was confirmed in accordance with routine procedures, and the plasmid was designated as pBBR1MCS-2::Pgap. Then, the pBBR1MCS-2::Pgap was cleaved with ScaI to obtain pBBR1MCS-2::Pgap/ScaI. To amplify a gene encoding an enzyme that catalyzes the reaction A, primers (SEQ ID NOs: 39 and 40) were designed for use in amplification of the full length of the acyl transferase gene pcaF (NCBI Gene ID: 1041755; SEQ ID NO: 38) by PCR using the genomic DNA of *Pseudomonas putida* strain KT2440 as a template, and a PCR reaction was performed in accordance with routine procedures. The resulting fragment and the pBBR1MCS-2::Pgap/ScaI were ligated together using the "In-Fusion HD Cloning Kit" (manufactured by Takara Bio Inc.), and the resulting plasmid was introduced into *E. coli* strain DH5α. The nucleotide sequence on the plasmid isolated from the obtained recombinant strain was confirmed in accordance with routine procedures, and the plasmid was designated as pBBR1MCS-2::AT. Then, the pBBR1MCS-2::AT was cleaved with HpaI to obtain pBBR1MCS-2::AT/HpaI. To amplify a gene encoding an enzyme that catalyzes the reactions D and E, primers (SEQ ID NOs: 43 and 44) were designed for use in amplification of a continuous sequence including the full lengths of genes together encoding a CoA transferase, pcaI and pcaJ (NCBI Gene IDs: 1046613 and 1046612, SEQ ID NOs: 41 and 42), by PCR using the genomic DNA of *Pseudomonas putida* strain KT2440 as a template, and a PCR reaction was performed in accordance with routine procedures. The resulting fragment and the pBBR1MCS-2::AT/HpaI were ligated together using the In-Fusion HD Cloning Kit, and the resulting plasmid was introduced into *E. coli* strain DH5α. The nucleotide sequence on the plasmid isolated from the obtained recombinant strain was confirmed in accordance with routine procedures, and the plasmid was designated as pBBR1MCS-2::ATCT.

The pBBR1MCS-2::ATCT is cleaved with ScaI to obtain pBBR1MCS-2::ATCT/ScaI. To amplify a nucleic acid encoding a polypeptide represented by SEQ ID NO: 10, primers (SEQ ID NOs: 45 and 46) were designed for use in amplification of a nucleic acid represented by SEQ ID NO: 9 using the genomic DNA of *Serratia marcescens* strain ATCC13880 as a template, and a PCR reaction was performed in accordance with routine procedures. The resulting fragment and the pBBR1MCS-2::ATCT/ScaI were ligated together using the "In-Fusion HD Cloning Kit" (manufactured by Takara Bio Inc.), and the resulting plasmid was introduced into *E. coli* strain DH5α. The nucleotide sequence on the plasmid isolated from the obtained recombinant strain was confirmed in accordance with routine procedures, and the plasmid was designated as pBBR1MCS-2::ATCTOR.

Reference Example 2

Production of a plasmid for expression of an enzyme that catalyzes a reaction to generate HMA-CoA from 3H A-CoA (the reaction C)

The pMW119 expression vector (manufactured by Nippon Gene Co., Ltd.), which is capable of autonomous replication in *E. coli*, was cleaved with SacI to obtain pMW119/SacI. To integrate a constitutive expression promoter into the vector, primers (SEQ ID NOs: 47 and 48) were designed for use in amplification of an upstream 200-b region (SEQ ID NO: 35) of gapA (NCBI Gene ID: NC_000913.3) by PCR using the genomic DNA of *Escherichia coli* str. K-12 substr. MG1655 as a template, and a PCR reaction was performed in accordance with routine procedures. The resulting fragment and the pMW119/SacI were ligated together using the In-Fusion HD Cloning Kit (manufactured by Takara Bio Inc.), and the resulting plasmid was introduced into *E. coli* strain DH5α. The nucleotide sequence on the plasmid isolated from the obtained recombinant *E. coli* strain was confirmed in accordance with routine procedures, and the plasmid was designated as pMW119::Pgap. Then, the pMW119::Pgap was cleaved with SphI to obtain pMW119::Pgap/SphI. To amplify a gene encoding an enzyme that catalyzes the reaction C, primers (SEQ ID NOs: 50 and 51) were designed for use in amplification of the full length of the enoyl-CoA hydratase gene paaF (NCBI Gene ID: 1046932, SEQ ID NO: 49) by PCR using the genomic DNA of *Pseudomonas putida* strain KT2440 as a template, and a PCR reaction was performed in accordance with routine procedures. The resulting fragment and the pMW119::Pgap/SphI were ligated together using the "In-Fusion HD Cloning Kit" (manufactured by Takara Bio Inc.), and the resulting plasmid was introduced into *E. coli* strain DH5α. The nucleotide sequence on the plasmid isolated from the obtained recombinant strain was confirmed in accordance with routine procedures. The obtained plasmid was designated as pMW119::EH.

Example 1

Production of a *Serratia* Microorganism Mutant in which the YjjPB Homolog Function is Deleted To delete the YjjPB homolog function of a *Serratia* microorganism, a *Serratia* microorganism mutant in which the yjjPB homolog gene was deleted was produced.

A method of deleting a yjjPB homolog gene was performed in accordance with a method described in *Proc Natl Acad Sci USA*. 2000 Jun. 6; 97 (12): 6640-6645.

A PCR was performed using the following: a kanamycin-resistant gene to be used as a marker when a gene was deleted; a template that was pKD4 containing an FRT (FLP recognition target) sequence for the dropout of the kanamycin-resistant gene; and primers that were oligo DNAs of SEQ ID NOs: 52 and 53. Thus, PCR fragments having a sequence length of 1.6 kb for deletion of a yjjPB homolog gene were obtained. Into a *Serratia grimesii* strain NBRC13537, pKD46 that was a X-red recombinase expression plasmid was introduced to obtain an ampicillin-resistant strain. The resulting strain was inoculated into 5 mL of an LB culture medium containing 500 μg/mL ampicillin, and incubated at 30° C. with shaking for 1 day. A culture fluid in an amount of 0.5 mL was inoculated into 50 mL of an LB culture medium containing 500 μg/mL ampicillin and 50 mM arabinose, and cultured with rotation at 30° C. for 2 hours. The culture fluid was cooled on ice for 20 minutes, and the bacterial cell was washed with 10% (w/w) glycerol three times. The pellets washed were suspended in 100 μL of 10% (w/w) glycerol, and mixed with 5 μL of PCR fragments, and the resulting mixture was cooled on ice in an electroporation cuvette for 10 minutes. The resulting mixture was subjected to electroporation (at 3 kV, 200Ω, and 25 μF) using a "Gene pulser" (manufactured by Bio-Rad Laboratories, Inc.), and then immediately supplemented with 1 mL of an SOC culture medium, and the resulting mixture was incubated at 30° C. with shaking for 2 hours. All of the resulting mixture was applied to an LB agar medium containing 25 μg/mL kanamycin, and incubated at 30° C. for 1 day. The resulting kanamycin-resistant strain was used for a colony direct PCR. The band length was used to verify the deletion of the gene of interest and the insertion of the kanamycin-resistant gene. The primers used were the oligo DNAs of SEQ ID NOs: 54 and 56.

Subsequently, the kanamycin-resistant strain was inoculated into 5 mL of an LB culture medium and subcultured at 37° C. twice to dropout pKD46, thereby obtaining an ampicillin-sensitive strain. Into the ampicillin-sensitive strain, pCP20 that was an FLP recombinase expression plasmid was introduced to obtain an ampicillin-resistant strain again. The resulting strain was subcultured at 40° C. twice, and then, subjected to a colony direct PCR. The band length was used to verify the dropout of the kanamycin-resistant gene. The primers used were the oligo DNAs of SEQ ID NOs: 55 and 56. The fact that the resulting strain was ampicillin-sensitive verified that pCP20 dropped out. The resulting strain was designated as SgΔyjjPB.

Example 2

Production of a *Serratia* Microorganism Mutant in which the YjjPB Homolog Function is Deleted and in which a Plasmid that Expresses Enzymes that Catalyze the Reactions A, B, D, and E is Introduced The plasmids produced in Reference Example 1 were each introduced into SgΔyjjPB produced in Example 1, whereby a *Serratia* microorganism mutant was produced.

The SgΔyjjPB was inoculated into 5 mL of an LB culture medium, and incubated at 30° C. with shaking for 1 day. The culture fluid in an amount of 0.5 mL was inoculated into 5 mL of an LB culture medium, and incubated at 30° C. with shaking for 2 hours. The culture fluid was cooled on ice for 20 minutes, and the bacterial cell was washed with 10% (w/w) glycerol three times. The pellets washed were suspended in 100 μL of 10% (w/w) glycerol, and mixed with 1 μL of pBBR1MCS-2::ATCTOR, and the resulting mixture was cooled on ice in an electroporation cuvette for 10 minutes. The resulting mixture was subjected to electroporation (at 3 kV, 200Ω, and 25 μF) using a "Gene pulser" (manufactured by Bio-Rad Laboratories, Inc.), and then immediately supplemented with 1 mL of an SOC culture medium, and the resulting mixture was incubated at 30° C. with shaking for 1 hour. The resulting mixture in an amount of 50 μL was applied to an LB agar medium containing 25 μg/ml, kanamycin, and incubated at 30° C. for 1 day. The resulting strain was designated as SgΔyjjPB/3HA.

Reference Example 3

Production of a *Serratia* Microorganism Mutant in which the YjjPB Homolog Function is not Deleted and in which a Plasmid that Expresses Enzymes that Catalyze the Reactions A, B, D, and E is Introduced The pBBR1 MCS-2::ATCTOR was introduced into a *Serratia grimesii* NBRC13537 in the same manner as in Example 2. The resulting strain was designated as Sg/3HA.

Example 3

Production Test of 3-Hydroxyadipic Acid by Using a *Serratia* Microorganism Mutant in which the YjjPB Homolog Function is Deleted and in which a Plasmid that Expresses Enzymes that Catalyze the Reactions A, B, D, and E is Introduced The *Serratia* microorganism mutant produced in Example 2 was used to perform a test for 3-hydroxyadipic acid production.

A loopful of each mutant produced in Example 2 was inoculated into 5 mL of the culture medium 1 (10 g/L Bacto Tryptone (manufactured by Difco Laboratories), 5 g/L Bacto Yeast Extract (manufactured by Difco Laboratories), 5 g/L sodium chloride, 25 μg/mL kanamycin) adjusted to pH 7 (a glass test tube having a diameter of 18 mm with an aluminum plug), and incubated at 30° C. with shaking at 120 $min^{-1}$ for 24 hours. Subsequently, 0.25 mL of the culture fluid was added to 5 mL of the culture medium II (50 g/L glucose, 1 g/L ammonium sulfate, 50 mM potassium phosphate, 0.025 g/L magnesium sulfate, 0.0625 mg/L iron sulfate, 2.7 mg/L manganese sulfate, 0.33 mg/L calcium chloride, 1.25 g/L sodium chloride, 2.5 g/L Bacto Tryptone, 1.25 g/L Bacto Yeast Extract, 25 μg/mL kanamycin) adjusted to pH 6.5 (a glass test tube having a diameter of 18 mm with an aluminum plug), and stationarily incubated at 30° C.

Quantitative Analysis of a Substrate and a Product

The supernatant separated from bacterial cells by centrifugation of the culture fluid was processed by membrane treatment using Millex-GV (0.22 μm; PVDF; manufactured by Merck KGaA), and the resulting filtrate was analyzed according to the following method to measure the concentrations of the following: the 3-hydroxyadipic acid and other products accumulated in the culture supernatant; and the sugars remaining unused in the culture medium. Furthermore, on the basis of the results, the yields of 3-hydroxyadipic acid and succinic acid were calculated using the following formula (2), and are shown in Table 1.

$$\text{Yield (\%)}=\text{amount of product generated (mol)}/\text{amount of sugar consumed (mol)}\times 100 \quad (2)$$

Quantitative Analysis of 3-Hydroxyadipic Acid by LC-MS/MS

HPLC: 1290 Infinity (manufactured by Agilent Technologies, Inc.)

Column: Synergi hydro-RP (manufactured by Phenomenex Inc.), length: 100 mm, internal diameter: 3 mm, particle size: 2.5 μm Mobile phase: 0.1% aqueous formic acid solution/methanol=70/30

Flow rate: 0.3 mL/min

Column temperature: 40° C.

LC detector: 1260DAD VL+ (210 nm)

MS/MS: Triple-Quad LC/MS (manufactured by Agilent Technologies, Inc.) Ionization method: ESI in negative mode Quantitative Analysis of an Organic Acid by HPLC HPLC: LC-10A (manufactured by Shimadzu Corporation)

Column: Shim-pack SPR-H (manufactured by Shimadzu GLC Ltd.), 250 mm in length, 7.8 mm in internal diameter, and 8 μm in particle size Shim-pack SCR-101H (manufactured by Shimadzu GLC Ltd.), 250 mm in length, 7.8 mm in internal diameter, and 10 μm in particle size Mobile phase: 5 mM p-toluenesulfonic acid Reaction liquid: 5 mMp-toluenesulfonic acid, 0.1 mM EDTA, 20 mM Bis-Tris Flow rate: 0.8 mL/min Column temperature: 45° C.

Detector: CDD-10Avp (manufactured by Shimadzu Corporation)

Quantitative Analysis of Sugars and Alcohols by HPLC

HPLC: Shimadzu Prominence (manufactured by Shimadzu Corporation)

Column: Shodex Sugar SH1011 (manufactured by Showa Denko K.K.), length: 300 mm, internal diameter: 8 mm, particle size: 6 m Mobile phase: 0.05M aqueous sulfuric acid solution Flow rate: 0.6 mL/min Column temperature: 65° C.

Detector: RID-10A (manufactured by Shimadzu Corporation)

Comparative Example 1

Production test of 3-Hydroxyadipic Acid by Using a *Serratia* Microorganism Mutant in which the YjjPB Function is not Deleted and in which a Plasmid that Expresses Enzymes that Catalyze the Reactions A, B, D, and E is Introduced The mutant produced in Reference Example 3 was cultured in the same manner as in Example 3. Measurements were made of the concentrations of the following: the 3-hydroxyadipic acid and other products accumulated in the culture supernatant; and the sugars remaining unused in the culture medium. Furthermore, on the basis of the results, the yields of 3-hydroxyadipic acid and succinic acid were calculated using the formula (2), and are shown in Table 1.

Comparison between the results of Comparative Example 1 and those of Example 3 has revealed that the deletion of the YjjPB homolog function of a *Serratia* microorganism enhances the yield of 3-hydroxyadipic acid.

TABLE 1

| | Strain | Yield of succinic acid (%) | Yield of 3HA (%) |
|---|---|---|---|
| Example 3 | SgΔyjjPB/3HA | 9.5 | 0.89 |
| Comparative Example 1 | Sg/3HA | 11 | 0.69 |

Example 4

Production of an *Escherichia* Microorganism Mutant in which the YjjPB Function is Deleted To delete the YjjPB function of an *Escherichia* microorganism, an *Escherichia* microorganism mutant in which the yjjPB gene was deleted was produced.

A method of deleting a yjjPB gene was performed in accordance with a method described in Proc Natl Acad Sci USA. 2000 Jun. 6; 97 (12): 6640-6645.

A PCR was performed using the following: a template that was pKD4; and primers that were oligo DNAs of SEQ ID NOs: 57 and 58. Thus, PCR fragments having a sequence length of 1.6 kb for deletion of yjjPB were obtained. Into an *Escherichia coli* str. K-12 substr. MG1655, pKD46 that was an FRT recombinase expression plasmid was introduced to obtain an ampicillin-resistant strain. The resulting strain was inoculated into 5 mL of an LB culture medium containing 100 μg/mL ampicillin, and incubated at 37° C. with shaking for 1 day. A culture fluid in an amount of 0.5 mL was inoculated into 50 mL of an LB culture medium containing 100 μg/mL ampicillin and 50 mM arabinose, and cultured with rotation at 37° C. for 2 hours. The culture fluid was cooled on ice for 20 minutes, and the bacterial cell was washed with 10% (w/w) glycerol three times. The pellets washed were suspended in 100 μL of 10% (w/w) glycerol, and mixed with 5 μL of PCR fragments, and the resulting mixture was cooled on ice in an electroporation cuvette for 10 minutes. The resulting mixture was subjected to electroporation (at 3 kV, 200Ω, and 25 μF) using a “Gene pulser” (manufactured by Bio-Rad Laboratories, Inc.), and then immediately supplemented with 1 mL of an SOC culture medium, and the resulting mixture was incubated at 37° C. with shaking for 2 hours. All of the resulting mixture was applied to an LB agar medium containing 25 μg/mL kanamycin, and incubated at 37° C. for 1 day. The resulting kanamycin-resistant strain was used for a colony direct PCR. The band length was used to verify the deletion of the gene of interest and the insertion of the kanamycin-resistant gene. The primers used were the oligo DNAs of SEQ ID NOs: 54 and 60.

Subsequently, the kanamycin-resistant strain was inoculated into 5 mL of an LB culture medium and subcultured at 40° C. twice to dropout pKD46, thereby obtaining an ampicillin-sensitive strain. Into the ampicillin-sensitive strain, pCP20 was introduced to obtain an ampicillin-resistant strain again. The resulting strain was subcultured at 43° C. twice, and then, subjected to a colony direct PCR. The band length was used to verify the dropout of the kanamycin-resistant gene. The primers used were the oligo DNAs of SEQ ID NOs: 59 and 60. The fact that the resulting strain was ampicillin-sensitive verified that pCP20 dropped out. The resulting strain was designated as EcΔyjjPB.

Example 5

Production of an *Escherichia* Microorganism Mutant in which the YjjPB Function is Deleted and in which a Plasmid that Expresses Enzymes that Catalyze the Reactions A, B, D, and E is Introduced The plasmids produced in Reference Example 1 were each introduced into EcΔyjjPB produced in Example 4, whereby an *Escherichia* microorganism mutant was produced.

The EcΔyjjPB was inoculated into 5 mL of an LB culture medium, and incubated at 37° C. with shaking for 1 day. The culture fluid in an amount of 0.5 mL was inoculated into 5 mL of an LB culture medium, and incubated at 37° C. with shaking for 2 hours. The culture fluid was cooled on ice for 20 minutes, and the bacterial cell was washed with 10% (w/w) glycerol three times. The pellets washed were suspended in 100 μL of 10% (w/w) glycerol, and mixed with 1 μL of pBBR1 MCS-2::ATCTOR and the resulting mixture was cooled on ice in an electroporation cuvette for 10 minutes. The resulting mixture was subjected to electroporation (at 3 kV, 200Ω, and 25 μF) using a "Gene pulser" (manufactured by Bio-Rad Laboratories, Inc.), and then immediately supplemented with 1 mL of an SOC culture medium, and the resulting mixture was incubated at 37° C. with shaking for 1 hour. The resulting mixture in an amount of 50 μL was applied to an LB agar medium containing 25 μg/mL kanamycin, and incubated at 37° C. for 1 day. The resulting strain was designated as EcΔyjjPB/3HA.

Reference Example 4

Production of an *Escherichia* Microorganism Mutant in which the YjjPB Function is not Deleted and in which a Plasmid that Expresses Enzymes that Catalyze the Reactions A, B, D, and E is Introduced The pBBR1MCS-2::ATCTOR was introduced into the *Escherichia coli* str. K-12 substr. MG1655 in the same manner as in Example 5. The resulting strain was designated as Ec/3HA.

Example 6

Production Test of 3-Hydroxyadipic Acid by Using an *Escherichia* Microorganism Mutant in which the YjjPB Function is Deleted and in which a Plasmid that Expresses Enzymes that Catalyze the Reactions A, B, D, and E is Introduced The mutant produced in Example 5 was cultured in the same manner as in Example 3. Measurements were made of the concentrations of the following: the 3-hydroxyadipic acid and other products accumulated in the culture supernatant; and the sugars remaining unused in the culture medium. On the basis of the values, the yields of 3-hydroxyadipic acid and succinic acid were calculated using the formula (2), and are shown in Table 2.

Comparative Example 2

Production Test of 3-Hydroxyadipic Acid by Using an *Escherichia* Microorganism Mutant in which the YjjPB Function is not Deleted and in which a Plasmid that Expresses Enzymes that Catalyze the Reactions A, B, D, and E is Introduced The mutant produced in Reference Example 4 was cultured in the same manner as in Example 3. Measurements were made of the concentrations of the following: the 3-hydroxyadipic acid and other products accumulated in the culture supernatant; and the sugars remaining unused in the culture medium. On the basis of the values, the yields of 3-hydroxyadipic acid and succinic acid were calculated using the formula (2), and are shown in Table 2.

Comparison between the results of Comparative Example 2 and those of Example 6 has revealed that the deletion of the YjjPB function of an *Escherichia* microorganism enhances the yield of 3-hydroxyadipic acid.

TABLE 2

| | Strain | Yield of succinic acid (%) | Yield of 3HA (%) |
|---|---|---|---|
| Example 6 | EcΔyjjPB/3HA | 8.8 | 1.2 |
| Comparative Example 2 | Ec/3HA | 14 | 1.1 |

Example 7

Production of a *Serratia* Microorganism Mutant in which the YjjPB Homolog Function is Deleted and in which a Plasmid that Expresses Enzymes that Catalyze the Reactions A, B, C, D, and E is Introduced The plasmid pMW I19::EH produced in Reference Example 2 was introduced into the *Serratia* microorganism mutant produced in Example 2, whereby a *Serratia* microorganism mutant was produced.

The SgΔyjjPB/3HA was inoculated into 5 mL of an LB culture medium containing 25 μg/mL kanamycin, and incubated at 30° C. with shaking for 1 day. The culture fluid in an amount of 0.5 mL was inoculated into 5 mL of an LB culture medium containing 25 μg/mL kanamycin, and incubated at 30° C. with shaking for 2 hours. The culture fluid was cooled on ice for 20 minutes, and the bacterial cell was washed with 10% (w/w) glycerol three times. The pellets washed were suspended in 100 μL of 10% (w/w) glycerol, and mixed with 1 μL of pMW119::EH, and the resulting mixture was cooled on ice in an electroporation cuvette for 10 minutes. The resulting mixture was subjected to electroporation (at 3 kV, 200Ω, and 25 μF) using a "Gene pulser" (manufactured by Bio-Rad Laboratories, Inc.), and then immediately supplemented with 1 mL of an SOC culture medium, and the resulting mixture was incubated at 30° C.

with shaking for 1 hour. The resulting mixture in an amount of 50 μL was applied to an LB agar medium containing 500 μg/mL ampicillin and 25 μg/mL kanamycin, and incubated at 30° C. for 1 day. The resulting strain was designated as SgΔyjjPB/HMA.

Reference Example 5

Production of a *Serratia* Microorganism Mutant in which the YjjPB Homolog Function is not Deleted and in which a Plasmid that Expresses Enzymes that Catalyze the Reactions A, B, C, D, and E is Introduced The pMW119::EH was introduced into the Sg/3HA in the same manner as in Example 7. The resulting strain was designated as Sg/HMA.

Example 8

Production Test of 3-Hydroxyadipic Acid and α-Hydromuconic Acid by Using a *Serratia* Microorganism Mutant in which the YjjPB Homolog Function is Deleted and in which a Plasmid that Expresses Enzymes that Catalyze the Reactions A, B, C, D, and E is Introduced The mutant produced in Example 7 was cultured in the same manner as in Example 3 except that a culture medium containing 25 μg/mL kanamycin and 500 μg/mL ampicillin was used. Measurements were made of the concentrations of the following: the 3-hydroxyadipic acid, α-hydromuconic acid, and other products accumulated in the culture supernatant; and the sugars remaining unused in the culture medium. In this regard, α-hydromuconic acid was quantitated using an LC-MS/MS under the same conditions as 3-hydroxyadipic acid. On the basis of the values, the yields of 3-hydroxyadipic acid, α-hydromuconic acid, and succinic acid were calculated using the formula (2), and are shown in Table 3.

Comparative Example 3

Production Test of 3-Hydroxyadipic Acid and α-Hydromuconic Acid by Using a *Serratia* Microorganism Mutant in which the YjjPB Homolog Function is not Deleted and in which a Plasmid that Expresses Enzymes that Catalyze the Reactions A, B, C, D, and E is Introduced The mutant produced in Reference Example 5 was cultured in the same manner as in Example 8. Measurements were made of the concentrations of the following: the 3-hydroxyadipic acid, α-hydromuconic acid, and other products accumulated in the culture supernatant; and the sugars remaining unused in the culture medium. On the basis of the values, the yields of 3-hydroxyadipic acid, α-hydromuconic acid, and succinic acid were calculated using the formula (2), and are shown in Table 3.

Comparison between the results of Comparative Example 3 and those of Example 8 has revealed that the deletion of the YjjPB homolog function of a *Serratia* microorganism enhances the yields of 3-hydroxyadipic acid and α-hydromuconic acid.

TABLE 3

| | Strain | Yield of succinic acid (%) | Yield of 3HA (%) | Yield of HMA (%) |
|---|---|---|---|---|
| Example 8 | SgΔyjjPB/HMA | 9.5 | 0.43 | 0.025 |
| Comparative Example 3 | Sg/HMA | 11 | 0.33 | 0.019 |

Example 9

Production of an *Escherichia* Microorganism Mutant in which the YjjPB Function is Deleted and in which a Plasmid that Expresses Enzymes that Catalyze the Reactions A, B, C, D, and E is Introduced The plasmid pMW119::EH produced in Reference Example 2 was introduced into the *Escherichia* microorganism mutant produced in Example 5, whereby an *Escherichia* mutant was produced.

The EcΔyjjPB/3HA was inoculated into 5 mL of an LB culture medium containing 25 μg/mL kanamycin, and incubated at 37° C. with shaking for 1 day. The culture fluid in an amount of 0.5 mL was inoculated into 5 mL of an LB culture medium containing 25 μg/ml, kanamycin, and incubated at 30° C. with shaking for 2 hours. The culture fluid was cooled on ice for 20 minutes, and the bacterial cell was washed with 10% (w/w) glycerol three times. The pellets washed were suspended in 100 μL of 10% (w/w) glycerol, and mixed with 1 μl, of pMW119::EH, and the resulting mixture was cooled on ice in an electroporation cuvette for 10 minutes. The resulting mixture was subjected to electroporation (at 3 kV, 200Ω, and 25 μF) using a “Gene pulser” (manufactured by Bio-Rad Laboratories, Inc.), and then immediately supplemented with 1 mL of an SOC culture medium, and the resulting mixture was incubated at 37° C. with shaking for 1 hour. The resulting mixture in an amount of 50 μL was applied to an LB agar medium containing 100 μg/mL ampicillin and 25 μg/mL kanamycin, and incubated at 37° C. for 1 day. The resulting strain was designated as EcΔyjjPB/HMA.

Reference Example 6

Production of an *Escherichia* Microorganism Mutant in which the YjjPB Function is not Deleted and in which a Plasmid that Expresses Enzymes that Catalyze the Reactions A, B, C, D, and E is Introduced The pMW119::EH was introduced into the Ec/3HA in the same manner as in Example 9. The resulting strain was designated as Ec/HMA.

Example 10

Production Test of 3-Hydroxyadipic Acid and α-Hydromuconic Acid by Using an *Escherichia* Microorganism Mutant in which the YjjPB Function is Deleted and in which a Plasmid that Expresses Enzymes that Catalyze the Reactions A, B, C, D, and E is Introduced The mutant produced in Example 9 was cultured in the same manner as in Example 6 except that a culture medium containing 25 μg/ml, kanamycin and 100 μg/mL ampicillin was used. Measurements were made of the concentrations of the following: the 3-hydroxyadipic acid, α-hydromuconic acid, and other products accumulated in the culture supernatant; and the sugars remaining unused in the culture medium. In this regard, α-hydromuconic acid was quantitated using an LC-MS/MS under the same conditions as 3-hydroxyadipic acid. On the basis of the values, the yields of 3-hydroxyadipic acid, α-hydromuconic acid, and succinic acid were calculated using the formula (2), and are shown in Table 4.

Comparative Example 4

Production Test of 3-Hydroxyadipic Acid and α-Hydromuconic Acid by Using an *Escherichia* Microorganism Mutant in which the YjjPB Function is not Deleted and in which a Plasmid that Expresses Enzymes that Catalyze the Reactions A, B, C, D, and E is Introduced The mutant produced in Reference Example 6 was cultured in the same manner as in Example 10. Measurements were made of the concentrations of the following: the 3-hydroxyadipic acid, α-hydromuconic acid, and other products accumulated in the culture supernatant; and the sugars remaining unused in the culture medium. On the basis of the values, the yields of 3-hydroxyadipic acid, α-hydromuconic acid, and succinic acid were calculated using the formula (2), and are shown in Table 4.

Comparison between the results of Comparative Example 4 and those of Example 10 has revealed that the deletion of the YjjPB function of an *Escherichia* microorganism enhances the yields of 3-hydroxyadipic acid and α-hydromuconic acid.

TABLE 4

| | Strain | Yield of succinic acid (%) | Yield of 3HA (%) | Yield of HMA (%) |
|---|---|---|---|---|
| Example 10 | EcΔyjjPB/HMA | 9.9 | 1.6 | 0.053 |
| Comparative Example 4 | Ec/HMA | 19 | 1.1 | 0.032 |

Example 11

Production of a *Serratia* Microorganism Mutant in which the YjjPB Homolog Function and the Pyruvate Kinase Function are Deleted and in which a Plasmid that Expresses Enzymes that Catalyze the Reactions A, B, C, D, and E is Introduced The pykF and pykA genes that encode pyruvate kinase in a *Serratia* microorganism were deleted to produce a *Serratia* microorganism mutant in which the pyruvate kinase function was deleted.

Production of a *Serratia* microorganism mutant in which pykF is deleted Genetic recombination was performed in the same manner as in Example 1 except that SgΔyjjPB was used as a subject from which pykF was to be deleted, that oligo DNAs of SEQ ID NOs: 61 and 62 were used as primers to obtain PCR fragments for deletion of pykF (SEQ ID NO: 29), that oligo DNAs of SEQ ID NO: 54 and 64 were used for colony direct PCR to verify the deletion of pykF and the insertion of a kanamycin-resistant gene, and that oligo DNAs of SEQ ID NOs: 63 and 64 were used for colony direct PCR to verify the dropout of the kanamycin-resistant gene. The resulting strain was designated as SgΔyjjPB,pykF.

Production of a *Serratia* Microorganism Mutant in which pykA is Deleted

Genetic recombination was performed in the same manner as in Example 1 except that SgΔjjPB,pykF was used as a subject from which pykA was to be deleted, that oligo DNAs of SEQ ID NOs: 66 and 67 were used as primers to obtain PCR fragments for deletion of pykA (SEQ ID NO: 65), that oligo DNAs of SEQ ID NO: 54 and 68 were used for colony direct PCR to verify the deletion of pykA and the insertion of a kanamycin-resistant gene, and that oligo DNAs of SEQ ID NOs: 68 and 69 were used for colony direct PCR to verify the dropout of the kanamycin-resistant gene. The resulting strain was designated as SgΔyjjPB, pykFA.

Production of a *Serratia* Microorganism Mutant in which a Plasmid that Expresses Enzymes that Catalyze the Reactions A, B, C, D, and E is Introduced The pBBR1MCS-2::ATCTOR generated in Reference Example 1 was introduced into the SgΔyjjPB,pykFA in the same manner as in Example 2. Next, the pMW119::EH was introduced into the resulting strain in the same manner as in Example 7. The resulting strain was designated as SgΔyjjPB,pykFA/HMA.

Reference Example 7

Production of a *Serratia* Microorganism Mutant in which the YjjPB Homolog Function is not Deleted, in which the Pyruvate Kinase Function is Deleted, and in which a Plasmid that Expresses Enzymes that Catalyze the Reactions A, B, C, D, and E is Introduced Genetic recombination was performed in the same manner as in Example 11 except that *Serratia grimesii* NBRC13537 was used as a subject from which pykF and pykA were to be deleted. The resulting strain was designated as SgΔpykFA/HMA.

Example 12

Production Test of 3-Hydroxyadipic Acid and α-Hydromuconic Acid by Using a *Serratia* Microorganism Mutant in which the YjjPB Homolog Function and the Pyruvate Kinase Function are Deleted and in which a Plasmid that Expresses Enzymes that Catalyze the Reactions A, B, C, D, and E is Introduced The mutant produced in Example 11 was cultured in the same manner as in Example 8. Measurements were made of the concentrations of the following: the 3-hydroxyadipic acid, α-hydromuconic acid, and other products accumulated in the culture supernatant; and the sugars remaining unused in the culture medium. On the basis of the values, the yields of 3-hydroxyadipic acid, α-hydromuconic acid, and succinic acid were calculated using the formula (2), and are shown in Table 5.

Comparative Example 5

Production Test of 3-Hydroxyadipic Acid and α-Hydromuconic Acid by Using a *Serratia* Microorganism Mutant in which the YjjPB Homolog Function is not Deleted, in which the Pyruvate Kinase Function is Deleted and, in which a Plasmid that Expresses Enzymes that Catalyze the Reactions A, B, C, D, and E is Introduced The mutant produced in Reference Example 7 was cultured in the same manner as in Example 12. Measurements were made of the concentrations of the following: the 3-hydroxyadipic acid, α-hydromuconic acid, and other products accumulated in the culture supernatant; and the sugars remaining unused in the culture medium. On the basis of the values, the yields of 3-hydroxyadipic acid, α-hydromuconic acid, and succinic acid were calculated using the formula (2), and are shown in Table 5.

Comparison between the results of Comparative Example 5 and those of Example 12 has revealed that the deletion of the YjjPB homolog function and pyruvate kinase function of a *Serratia* microorganism enhances the yields of 3-hydroxyadipic acid and α-hydromuconic acid.

TABLE 5

| | Strain | Yield of succinic acid (%) | Yield of 3HA (%) | Yield of HMA (%) |
|---|---|---|---|---|
| Example 12 | SgΔyjjPB, pykFA/HMA | 41 | 2.0 | 0.11 |
| Comparative Example 5 | SgΔpykFA/HMA | 43 | 1.8 | 0.10 |

Example 13

Production of an *Escherichia* Microorganism Mutant in which the YjjPB Function and the Pyruvate Kinase Function are Deleted The pykF and pykA genes that encode pyruvate kinase in an *Escherichia* microorganism were deleted to produce an *Escherichia* microorganism mutant in which the pyruvate kinase function was deleted.

Production of an *Escherichia* Microorganism Mutant in which pykF is Deleted

Genetic recombination was performed in the same manner as in Example 4 except that EcΔyjjPB was used as a subject from which pykF was to be deleted, that oligo DNAs of SEQ ID NOs: 70 and 71 were used as primers to obtain PCR fragments for deletion of pykF (NCBI Gene ID: 946179, SEQ ID NO: 26), that oligo DNAs of SEQ ID NOs: 54 and 73 were used for colony direct PCR to verify the deletion of pykF and the insertion of a kanamycin-resistant gene, and that oligo DNAs of SEQ ID NOs: 72 and 73 were used for colony direct PCR to verify the dropout of the kanamycin-resistant gene. The resulting strain was designated as EcΔyjjPB,pykF.

Production of an *Escherichia* Microorganism Mutant in which pykA is Deleted

Genetic recombination was performed in the same manner as in Example 4 except that EcΔyjjPB,pykF was used as a subject from which PykA was to be deleted, that oligo DNAs SEQ ID NOs: 75 and 76 were used as primers to obtain PCR fragments for deletion of pykA (NCBI Gene ID: 946527, SEQ ID NO: 74), that oligo DNAs of SEQ ID NOs: 54 and 78 were used for colony direct PCR to verify the deletion of pykA and the insertion of a kanamycin-resistant gene, and that oligo DNAs of 77 and 78 were used for colony direct PCR to verify the dropout of the kanamycin-resistant gene. The resulting strain was designated as EcΔyjjPB,pykFA.

Reference Example 8

Production of an *Escherichia* Microorganism Mutant in which the YjjPB Function is not Deleted, in which the Pyruvate Kinase Function is Deleted, and in which a Plasmid that Expresses Enzymes that Catalyze the Reactions A, B, C, D, and E is Introduced Genetic recombination was performed in the same manner as in Example 13 except that *Escherichia coli* str. K-12 substr. MG1655 was used as a subject from which pykF and pykA were to be deleted. The resulting strain was designated as EcΔpykFA/HMA.

Example 14

Production Test of 3-Hydroxyadipic Acid and α-Hydromuconic Acid by Using an *Escherichia* Microorganism Mutant in which the YjjPB Function and the Pyruvate Kinase Function are Deleted and in which a Plasmid that Expresses Enzymes that Catalyze the Reactions A, B, C, D, and E is Introduced The mutant produced in Example 13 was cultured in the same manner as in Example 10. Measurements were made of the concentrations of the following: the 3-hydroxyadipic acid, α-hydromuconic acid, and other products accumulated in the culture supernatant; and the sugars remaining unused in the culture medium. On the basis of the values, the yields of 3-hydroxyadipic acid, α-hydromuconic acid, and succinic acid were calculated using the formula (2), and are shown in Table 6.

Comparative Example 6

Production Test of 3-Hydroxyadipic Acid and α-Hydromuconic Acid by Using an *Escherichia* Microorganism Mutant in which the YjjPB Function is not Deleted, in which the Pyruvate Kinase Function is Deleted, and in which a Plasmid that Expresses Enzymes that Catalyze the Reactions A, B, C, D, and E is Introduced The mutant produced in Reference Example 8 was cultured in the same manner as in Example 14. Measurements were made of the concentrations of the following: the 3-hydroxyadipic acid, α-hydromuconic acid, and other products accumulated in the culture supernatant; and the sugars remaining unused in the culture medium. On the basis of the values, the yields of 3-hydroxyadipic acid, α-hydromuconic acid, and succinic acid were calculated using the formula (2), and are shown in Table 6.

Comparison between the results of Comparative Example 6 and those of Example 14 has revealed that the deletion of the YjjPB function and pyruvate kinase function of an *Escherichia* microorganism enhances the yields of 3-hydroxyadipic acid and α-hydromuconic acid.

TABLE 6

| | Strain | Yield of succinic acid (%) | Yield of 3HA (%) | Yield of HMA (%) |
|---|---|---|---|---|
| Example 14 | EcΔpykFA, yjjPB/HMA | 25 | 4.8 | 0.17 |
| Comparative Example 6 | EcΔpykFA/HMA | 45 | 3.7 | 0.10 |

Reference Example 9

Production of Plasmids to Enhance YjjPB Function

The pCDF-1b expression vector (manufactured by Merck Millipore), which is capable of autonomous replication in *E. coli*, was cleaved with HindIII and XbaI to obtain pCDF-1b/HindIII,XbaI. To integrate yjjP, yjjB, and promoter regions thereof, primers (SEQ ID NOs: 80 and 81) were designed for use in amplification of yjjP, yjjB, and promoter regions thereof (SEQ ID NO: 79) by PCR using the genomic DNA of *Escherichia coli* str. K-12 substr. MG1655 as a template, and a PCR reaction was performed in accordance with routine procedures. The resulting fragment and the pCDF-1b/HindIII,XbaI were ligated together using the In-Fusion HD Cloning Kit (manufactured by Takara Bio Inc.), and the resulting plasmid was introduced into *E. coli* strain DH5a. The nucleotide sequence on the plasmid isolated from the resulting recombinant *E. coli* strain was confirmed in accordance with routine procedures, and the plasmid was designated as pCDF::yjjPB.

Reference Example 10

Production of an *Escherichia* Microorganism Mutant in which the YjjPB Function is Enhanced and in which a Plasmid that Expresses Enzymes that Catalyze the Reactions A, B, C, D, and E is Introduced The plasmid pCDF::yjjPB produced in Reference Example 9 or pCDF-1b as a control was introduced into the *Escherichia* microorganism mutant produced in Reference Example 6, whereby an *Escherichia* mutant was produced.

The Ec/HMA was inoculated into 5 mL of an LB culture medium containing 25 μg/mL kanamycin and 100 μg/mL ampicillin, and incubated at 37° C. with shaking for 1 day. The culture fluid in amount of 0.5 mL was inoculated into 5 mL of an LB culture medium containing 25 μg/mL kanamycin and 100 μg/mL ampicillin, and incubated at 30° C. with shaking for 2 hours. The culture fluid was cooled on ice for 20 minutes, and the bacterial cell was washed with 10% (w/w) glycerol three times. The pellets washed were suspended in 100 μL of 10% (w/w) glycerol, and mixed with 1 μL of pCDF::yjjPB or pCDF-1b, and the resulting mixture was cooled on ice in an electroporation cuvette for 10 minutes. The resulting mixture was subjected to electroporation (at 3 kV, 200Ω, and 25 μF) using a "Gene pulser" (manufactured by Bio-Rad Laboratories, Inc.), and then immediately supplemented with 1 mL of an SOC culture medium, and the resulting mixture was incubated at 37° C. with shaking for 1 hour. The resulting mixture in an amount of 50 μL was applied to an LB agar medium containing 25 μg/mL kanamycin, 100 μg/mL ampicillin, and 50 μg/mL streptomycin, and incubated at 37° C. for 1 day. The resulting strains were designated as Ec/HMA,yjjPB and Ec/HMA,pCDF respectively.

Reference Example 11

Production Test of 3-Hydroxyadipic Acid and α-Hydromuconic Acid by Using an *Escherichia* Microorganism Mutant in which the YjjPB Function is Enhanced and in which a Plasmid that Expresses Enzymes that Catalyze the Reactions A, B, C, D, and E is Introduced The mutant produced in Reference Example 10 was cultured in the same manner as in Example 10 except that a culture medium containing 25 μg/mL kanamycin, 100 μg/mL ampicillin, and 50 μg/mL streptomycin was used. Measurements were made of the concentrations of the following: the 3-hydroxyadipic acid. α-hydromuconic acid, and other products accumulated in the culture supernatant; and the sugars remaining unused in the culture medium. On the basis of the values, the yields of 3-hydroxyadipic acid, α-hydromuconic acid, and succinic acid were calculated using the formula (2), and are shown in Table 7.

Comparison of the results of Reference Example 11 has revealed that the enhancement of the YjjPB function of an *Escherichia* microorganism increases the yield of succinic acid and decreases the yields of 3-hydroxyadipic acid and α-hydromuconic acid.

TABLE 7

| | Strain | Yield of succinic acid (%) | Yield of 3HA (%) | Yield of HMA (%) |
|---|---|---|---|---|
| Reference | Ec/HMA, yjjPB | 13 | 1.6 | 0.026 |
| Example 11 | Ec/HMA, PCDF | 16 | 0.38 | 0.0074 |

Example 15

Production of an *Escherichia* Microorganism Mutant in which the YeeA Function is Deleted To delete the YeeA function of an *Escherichia* microorganism, an *Escherichia* microorganism mutant in which the yeeA gene was deleted was produced.

The yeeA gene was deleted in the same manner as in Example 4 except that oligo DNAs of SEQ ID NOs: 82 and 83 were used as primers to amplify a kanamycin-resistant gene and the FRT sequence using pKD4 as a template, that oligo DNAs of SEQ TD NOs: 54 and 85 were used as primers to verify the introduction of a kanamycin-resistant gene, and that oligo DNAs of SEQ ID NOs: 84 and 85 were used as primers to verify the dropout of the kanamycin-resistant gene. The resulting strain was designated as EcΔyeeA.

Example 16

Production of an *Escherichia* Microorganism Mutant in which the YeeA Function is Deleted and in which a Plasmid that Expresses Enzymes that Catalyze the Reactions A, B, D, and E is Introduced In the same manner as in Example 5, the plasmid produced in Reference Example 1 was introduced into EcΔyeeA produced in Example 15, whereby an *Escherichia* microorganism mutant was produced. The resulting strain was designated as EcΔyeeA/3HA.

Example 17

Production Test of 3-Hydroxyadipic Acid by Using an *Escherichia* Microorganism Mutant in which the YeeA Function is Deleted and in which a Plasmid that Expresses Enzymes that Catalyze the Reactions A, B, D, and E is Introduced The mutant produced in Example 16 was cultured in the same manner as in Example 6. Measurements were made of the concentrations of the following: the 3-hydroxyadipic acid and other products accumulated in the culture supernatant; and the sugars remaining unused in the culture medium. On the basis of the values, the yields of 3-hydroxyadipic acid and succinic acid were calculated using the formula (2), and are shown in Table 8.

Comparison between the results of Comparative Example 2 and those of Example 17 has revealed that the deletion of the YeeA function of an *Escherichia* microorganism enhances the yield of 3-hydroxyadipic acid.

TABLE 8

| | Strain | Yield of succinic acid (%) | Yield of 3HA (%) |
|---|---|---|---|
| Example 17 | EcΔyeeA/3HA | 5.8 | 1.6 |
| Comparative Example 2 | Ec/3HA | 14 | 1.1 |

Example 18

Production of an *Escherichia* Microorganism Mutant in which the YnfM Function is Deleted To delete the YnfM function of an *Escherichia* microorganism, an *Escherichia* microorganism mutant in which the YnfM gene was deleted was produced.

The ynfM gene was deleted in the same manner as in Example 4 except that oligo DNAs of SEQ ID NOs: 86 and 87 were used as primers to amplify a kanamycin-resistant gene and the FRT sequence using pKD4 as a template, that oligo DNAs of SEQ ID NOs: 54 and 89 were used as primers to verify the introduction of a kanamycin-resistant gene, and that oligo DNAs of SEQ ID NOs: 88 and 89 were used as primers to verify the dropout of the kanamycin-resistant gene. The resulting strain was designated as EcΔynfM.

Example 19

Production of an *Escherichia* Microorganism Mutant in which the YnfM Function is Deleted and in which a Plasmid that Expresses Enzymes that Catalyze the Reactions A, B, D, and E is Introduced In the same manner as in Example 5, the plasmid produced in Reference Example 1 was introduced into EcΔynfM produced in Example 18, whereby an *Escherichia* microorganism mutant was produced. The resulting strain was designated as EcΔynfM/3HA.

Example 20

Production Test of 3-Hydroxyadipic Acid by Using an *Escherichia* Microorganism Mutant in which the YnfM Function is Deleted and in which a Plasmid that Expresses Enzymes that Catalyze the Reactions A, B, D, and E is Introduced The mutant produced in Example 19 was cultured in the same manner as in Example 6. Measurements were made of the concentrations of the following: the 3-hydroxyadipic acid and other products accumulated in the culture supernatant; and the sugars remaining unused in the culture medium. On the basis of the values, the yields of 3-hydroxyadipic acid and succinic acid were calculated using the formula (2), and are shown in Table 9.

Comparison between the results of Comparative Example 2 and those of Example 20 has revealed that the deletion of the YnfM function of an *Escherichia* microorganism enhances the yield of 3-hydroxyadipic acid.

TABLE 9

| | Strain | Yield of succinic acid (%) | Yield of 3HA (%) |
|---|---|---|---|
| Example 20 | EcΔynfM/3HA | 7.9 | 1.4 |
| Comparative Example 2 | Ec/3HA | 14 | 1.1 |

Sequence Listing

The invention claimed is:

1. A genetically modified microorganism having an ability to produce 3-hydroxyadipic acid and/or α-hydromuconic acid, and having an enhanced enzymatic activity to catalyze a reaction to reduce 3-oxoadipyl-CoA to 3-hydroxyadipyl-CoA, wherein, in the genetically modified microorganism, a dicarboxylic acid excretion carrier function is deleted or decreased.

2. The genetically modified microorganism according to claim 1, wherein the deletion or decrease of the dicarboxylic acid excretion carrier function is caused by the deletion or decrease of the function of YjjP or a homolog thereof and/or YjjB or a homolog thereof.

3. The genetically modified microorganism according to claim 2, wherein a yjjP gene or a homolog gene thereof and/or a yjjB gene or a homolog gene thereof is/are destroyed or deleted.

4. The genetically modified microorganism according to claim 1, wherein the deletion or decrease of the dicarboxylic acid excretion carrier function is caused by the deletion or decrease of the function of YeeA or a homolog thereof and/or YnfM or a homolog thereof.

5. The genetically modified microorganism according to claim 4, wherein a yeeA gene or a homolog gene thereof and/or a ynfM gene or a homolog gene thereof is/are destroyed or deleted.

6. The genetically modified microorganism according to claim 1, wherein the microorganism belongs to the genus *Escherichia* or *Serratia*.

7. The genetically modified microorganism according to claim 1, wherein, in the genetically modified microorganism, a gene encoding an enzyme that catalyzes a reaction to reduce 3-oxoadipyl-CoA to 3-hydroxyadipyl-CoA is introduced.

8. A method of producing 3-hydroxyadipic acid and/or α-hydromuconic acid, comprising culturing the genetically modified microorganism according to claim 1.

* * * * *